United States Patent
Mazzeo et al.

[11] Patent Number: 6,090,250
[45] Date of Patent: Jul. 18, 2000

[54] CHIRAL SURFACTANTS AND METHODS FOR THEIR USE IN CHIRAL SEPARATIONS

[75] Inventors: Jeffrey R. Mazzeo, Chelmsford; Edward R. Grover, Randolph; Michael E. Swartz, Uxbridge, all of Mass.; Michael Merion, Los Gatos, Calif.; John S. Petersen, Acton, Mass.

[73] Assignee: Waters Investments Limited, Wilmington, Del.

[21] Appl. No.: 08/617,916

[22] PCT Filed: Sep. 20, 1994

[86] PCT No.: PCT/US94/10655

§ 371 Date: Mar. 20, 1996

§ 102(e) Date: Mar. 20, 1996

[87] PCT Pub. No.: WO95/08529

PCT Pub. Date: Mar. 30, 1995

Related U.S. Application Data

[63] Continuation-in-part of application No. 08/124,681, Sep. 20, 1993.

[51] Int. Cl.[7] .......................... G01N 27/26; G01N 27/447
[52] U.S. Cl. .......................... 204/451; 204/601; 252/353; 252/355; 252/356
[58] Field of Search ...................................... 204/451, 452, 204/453, 454, 455, 601, 602, 603, 604, 605; 252/355, 356, 353

[56] References Cited

U.S. PATENT DOCUMENTS

| | | | |
|---|---|---|---|
| 2,871,225 | 1/1959 | Bortnick | 528/328 |
| 4,675,300 | 6/1987 | Zare et al. | 436/172 X |
| 5,084,150 | 1/1992 | Karger et al. | 204/451 |

FOREIGN PATENT DOCUMENTS

| | | |
|---|---|---|
| 208961 | 1/1987 | European Pat. Off. . |
| 0 300 448 | 1/1989 | European Pat. Off. . |

(List continued on next page.)

OTHER PUBLICATIONS

Akira Dobashi et al, Enantioselective hydrophobic entanglement of enantiomeric solutes with chiral functionalized micelles by electrokinetic chromatography 480 (1989) *no month available 413–420.

(List continued on next page.)

*Primary Examiner*—William H. Beisner
*Assistant Examiner*—John S. Starsiak, Jr.
*Attorney, Agent, or Firm*—Hamilton, Brook, Smith & Reynolds, P.C.

[57] ABSTRACT

Chiral surfactants, methods for their synthesis and use, and apparatus designed to facilitate chiral separations using nucellar capillary electrophoresis is disclosed. A chiral surfactant having the general formula:

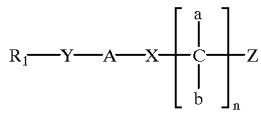

is described, R1 is the hydrophobic tail, Y-A-X is the linker, the brackets define a chiral center, and the hydrophilic head group is Z. All the various components may potentiate the enantioselectivity of the chiral surfactant. The capillary electrophoresis (CE) system includes a narrow diameter capillary, a high voltage power supply, an electrolyte reservoir at each end of the capillary, a means for injecting a sample, and a detector. Chiral surfactants are dissolved in the electrolyte above their critical micelle concentration (cmc), resulting in the formation of chiral micelles. The electrolyte reservoirs and capillary tube are filled with the electrolyte. A sample containing a mixture of enantiomers is then injected into the capillary, and a high voltage potential is applied across the capillary. The sample components migrate through the capillary due to the influence of the applied electric field. An example separation of the four sereoisomers of aspartame is shown.

52 Claims, 46 Drawing Sheets

FOREIGN PATENT DOCUMENTS

| | | |
|---|---|---|
| 0 408 448 | 1/1991 | European Pat. Off. . |
| 3-270724 | 12/1991 | Japan . |
| 3270724 | 12/1991 | Japan . |
| 3270725 | 12/1991 | Japan . |
| 90/14429 | 11/1990 | WIPO . |

OTHER PUBLICATIONS

Akira Dobashi et al, "Optical resolution of enantiomers with chiral mixed micelles by electrokinetic chromatography" Analytical Chemistry, vol. 61, No. 17 (Sep. 1, 1984) 1986–1988.

Koji Otsuka et al, "Enantiomeric resolution by micellar electrokinetic chromatography with chiral surfactants" Journal of Chromatography, 515 (1990) *no month available 221–226.

Koji Otsuka et al, "Chiral separations by micellar electrokinetic chromatography with sodium N–dodeconoyl–L–valinate", Journal of Chromatography, 559 (1991) *no month available (1–2), 209–14.

Hirotaka Ihara et al, "Enantioselective ester hydrolysis by hydroxamic acids of N–benzyloxycarbonyl–L–amino acids or optically active amines in cetyltrimethylammonium bromide micelles" Journal of Organic Chemistry 45(9), *no month available (1980) 1623–5.

Benjamin Weiss et al "Effects of amino acid amides and aminothiols on 3–mercaptopropionic acid–induced convulsions and phencylidine–induced hyperactivity in mice" Res. Commun. Psychol. Psychiatry Behav. 15(1–2), *no month available (1990) 53–58.

Pritpal K. Slaich et al, "The binding of amide substrate analogs to phospholipase A2. Studies by carbon–13 nuclear magnetic resonance and infrared spectroscopy." Biochem. J., 288 (2) *no month available (1992) 167–73.

Colin Bennion et al, "Design and synthesis of some substrate analog inhibitors of phospholipase A2 and investigations by NMR and molecular modeling into the binding interactions in the enzyme–inhibitor complex", J. Med. Chem., 35 (16), *no month available (1992) 2939–51.

Marco C. Cleij et al, "Mechanism of enantioselective ester cleavage by histidine containing dipeptides at a micellar interface" Journal of Organic Chemistry, 56(12), (1991) 3883–91.

D. Marr–Leisy et al, "The comparative spreading behavior of enantiomeric and racemic tyrosine amphiphiles" Colloid Polym. Sci, 283 (10) (1985) 791–8.

Gozel, P. et al., "Electrokinetic Resolution of Amino Acid Enantiomers with Copper (II)–Aspartame Support Electrolyte," Anal. Chem. 59:44–49 *no month available (1987).

Gassmann, E. et al., "Electrokinetic Separation of Chiral Compounds," Science 230:813–814 *no month available (1985).

Terabe, S. et al., "Electrokinetic Chromatography with Micellar Solution and Open–Tubular Capillary," Anal. Chem. 57:834–841 *no month available (1985).

Terabe, S. et al., "Electrokinetic Separations with Micellar Solutions and Open–Tubular Capillaries," Anal. Chem. 56:111–113 *no month available (1984).

Dobashi, Akira et al., "Enantioselective Hydrophobic Entanglement of Enantiomeric Solutes with Chiral Functionalized Micelles by Electrokinetic Chromatography," Journal of Chromatography 480:413–420 *no month available (1989).

Dobashi, Akira et al., "Optical Resolution of enantiomers with Chiral Mixed Micelles by Electrokinetic Chromatography," Anal. Chem. 61:1984–1986 *no month available (1989).

Otsuka, Koji and Terabe, Shigeru, "Effects of methanol and urea on optical resolution of phenylthiohydantoin–D–L–amino acids by micellar electrokinetic chromatography with sodium N–dodecanoyl–L–valinate," Electrophoresis 11:982–984 *no month available (1990).

Kuhn, R. et al., "Chiral Separations by Host–Guest Complexation with Cyclodextrin and Crown Ether in Capillary Zone electrophoresis," Chromatographia 33, No. 1/2:32–36 *no month available (1992).

Barker, Geoffrey E. et al., "Chiral Separation of Leucovorin with Bovine Serum Albumin Using Affinity Capillary Electrophoresis," Anal. Chem. 64:3024–3028 *no month available (1992).

D'Hulst, A. and Verbeke, N. "Chiral separation by capillary electrophoresis with oligosaccharides," Journal of Chromatography, 608:275–287 *no month available (1992).

Soini, Helena et al., "Chiral separations of basic drugs and quantitation of bupivacaine enantiomers in serum by capillary electrophoresis with modified cyclodextrin buffers," Journal of Chromatography, 608:265–274 *no month available (1992).

Nishi, Hiroyuiki et al., "Chiral separation of diltiazem, trimetoquinol and related compounds by micellar electrokinetic chromatography with bile salts," Journal of Chromatography, 515:233–243 *no month available (1990).

Shinozuka, Kazuo, et al., "Enantiomeric Bleomycin Model compounds Bearing Long Alkyl–Chain," Tetrahedron Letters, 32(47):6869–6872 *no month available (1991).

Guttman, A. et al., "Use of Complexing Agents for Selective Separation in High–Performance Capillary Electrophoresis—Chiral Resolution via Cyclodextrins Incorporated Within Polyacrylamide Gel Columns," Journal of Chromatography 448:41–53 *no month available (1988).

Liesen, Gregory P. and Sukenik, Chaim N., "Activated Anhydrides of Tartaric and Malic Acids," J. Org. Chem. 52:455–457 *no month available (1987).

Lindner, Wolfgang, F., "Chromatographic resolution of amino acids using tartaric acid mono–n–octylamide as mobile phase additive," Chemical Abstracts, 106(21):774, Abstract No. 176818u *no month available **no date available.

Fuhrhop, Jürgen–Hinrich et al., "Cloth–like Aggregates of Micellar Fibers Made of N–Dodecyltartaric Acid Monoamides," J. Am. Chem. Soc. 112:2827–2829 *no month available (1990).

Reig. F. et al., "Lipoenkephalins: a study of the surface–active and pharmacological properties of these new morphine–like peptides," Chemical Abstracts, 98 (3):68, Abstract No.: 11624f *no month available (1983).

Weiss, Benjamin et al., "Effects of amino acid amides and aminothiols on 3–mercaptopropionic acid–induced convulsions and phencyclidine–induced hyperactivity in mice," Chemical Abstracts, 114(11):55, Abstract No.: 94966s *no month available (1991).

Lentini, Aldo et al., "Synthetic inhibitors of human leukocyte elastase. Part 3. Peptides with alkyl groups at the N–or C–terminus. Non–toxic competitive inhibitors of human leukocyte elastase." Chemical Abstracts, 107(13):32, Abstract No.: 108984r *no month available (1987).

Sumitomo Chemical Co., Ltd. "NMR shift reagent," *Chemical Abstracts,* 102(26):674, Abstract No.: 203766h *no month available (1985).

Tamura, Masahiro et al., "Structural correlation between some amides and a taste receptor model," *Chemical Abstracts,* 110(23):490, Abstract No.: 209946x *no month available (1989).

Clement, Mark A. et al., "Cytotoxic effects of methionine alkyl esters and amides in normal and neoplastic cell lines," *Chemical Abstracts,* 111(13):14, Abstract No.: 108490j *no month available (1989).

Pongracz, Krisztina et al., "Quinoline–and naphthyridine–3–carboxylic acid amides," *Chemical Abstracts,* 106(5):681, Abstract No.: 120225f *no month available (1987).

Slaich, Pritpal K., et al., "The binding of amide substrate analogs pholipase $A_2$ Studies by carbon–13 nuclear magnetic and infrared spectroscopy," *Chemical Abstracts,* 118(3):291, Abstract No.: 18380p *no month available (1993).

Uemura, Keiichi et al., "Effect of an inhibitor of glucosylceramide synthesis of cultured rabbit skin fibroblasts," *Chemical Abstracts,* 114(1):401, Abstract No.: 3972B *no month available (1991).

George, Edwin E. and Polya, John D., Acyl sphingoids and related oxazolines, *Chemical Abstracts,* 93(15):709, Abstract No.: 150152k *no month available (1980).

Bielawska, Alicja et al., "Ceramide–mediated Biology," *Journal of Biological Chemistry,* 267(26):18493–18497 *no month available (1992).

Oi, Naobumi et al., "Enantiomer separation by HPLC on reversed phase silica gel coated with copper (II) complexes of (R,R)–tartaric acid mono–amide derivatives," *Chemical Abstracts* 118(20):913, Abstract No.: 204438p *no month available (1993).

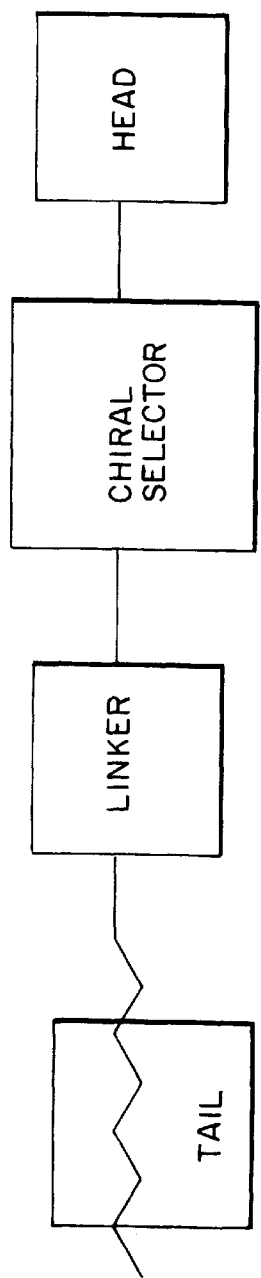
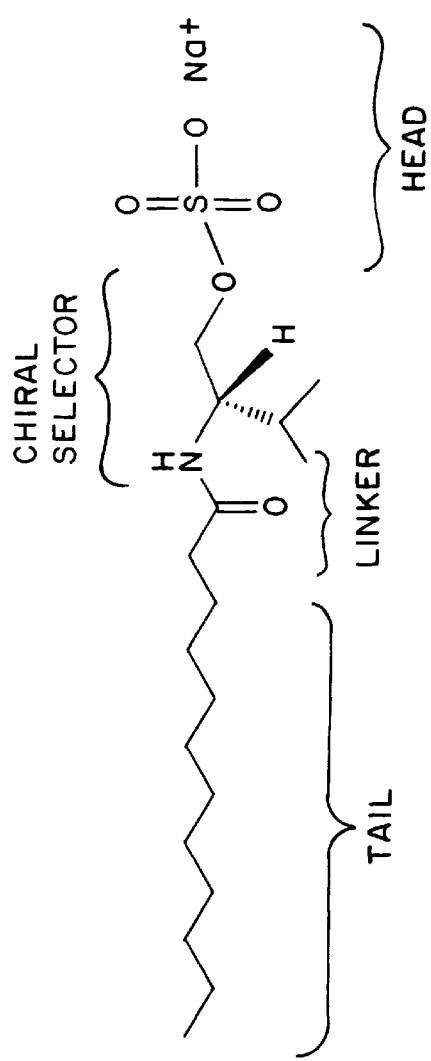
FIG. 2A
FIG. 2B (S)-N-DODECOXYCARBONYLVALINE (R)-N-DODECOXYCARBONYLVALINE (S)-N-DODECOXYCARBONYL-TERT-LEUCINE (S)-N-TETRADECOXYCARBONYLVALINE (S)-N-DODECOXYCARBONYLPHENYL GLYCINE (S)-N-DODECYLPOLYOXYETHYLENE(4)OXYCARBONYLVALINE (S)-N-DODECYLAMINOCARBONYLVALINE (S)-N-DODECYLSULFONYLVALINE (S)-N-DODECOXYCARBONYLVALINOL (S)-N-CHOLESTEROXYCARBONYLVALINOL (S)-N-DODECYLAMINOCARBONYLVALINOL (S)-2-[(1-OXODODECOXY)AMINO]-3-METHYL-1-SULFOOXYBUTANE (S)-2-[(1-OXODODECYL)AMINO]-3-METHYL-1-SULFOOXYBUTANE (S)-2-[(1-OXODODECYLAMINO)AMINO]-3-METHYL-1-SULFOOXYBUTANE (S)-[(1-OXOCHOLESTEROXY)AMINO]-3-METHYL-1-SULFOOXYBUTANE (S)-2-[(1-OXO-N-DODECANOYLVALINE)AMINOETHANESULFONIC ACID (S)-N-DODECANOYLVALINE (R)-N-DODECANOYLVALINE (S)-N-DODECANOYLPHENYLGLYCINE (S)-N-DODECANOYLSERINE (S)-N-DODECANOYLPROLINE (S)-N-DODECANOYLASPARTIC ACID

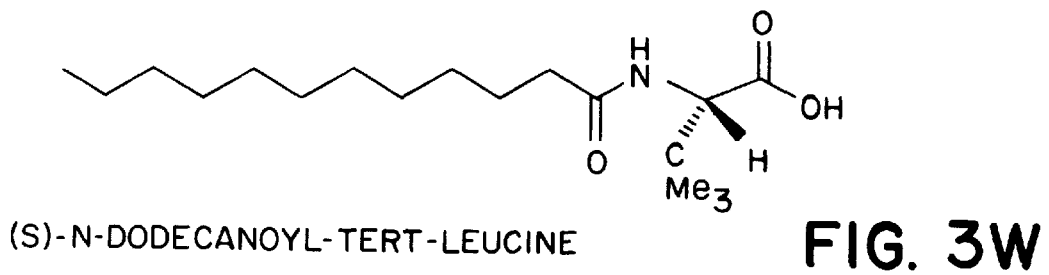
(S)-N-DODECANOYL-TERT-LEUCINE  FIG. 3W
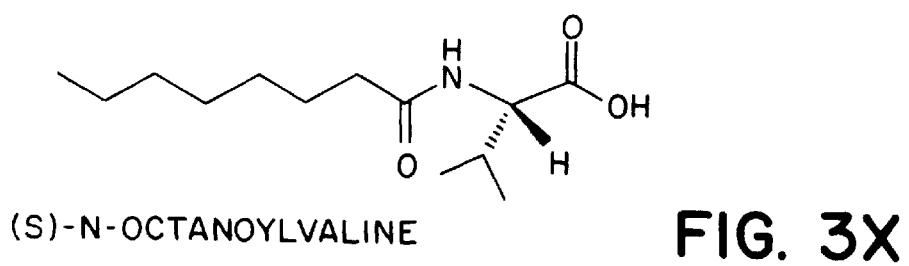
(S)-N-OCTANOYLVALINE  FIG. 3X
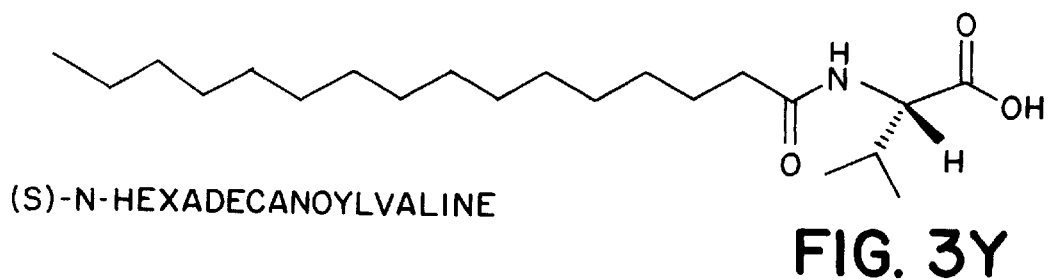
(S)-N-HEXADECANOYLVALINE
FIG. 3Y
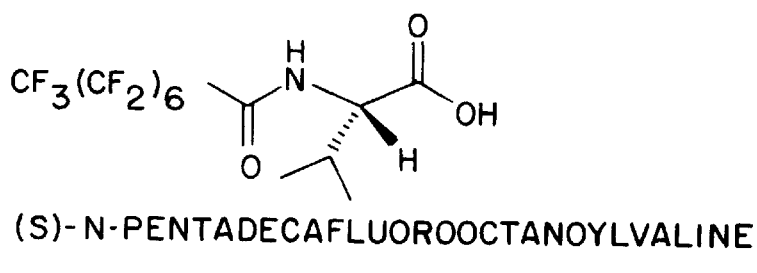
(S)-N-PENTADECAFLUOROOCTANOYLVALINE  FIG. 3Z
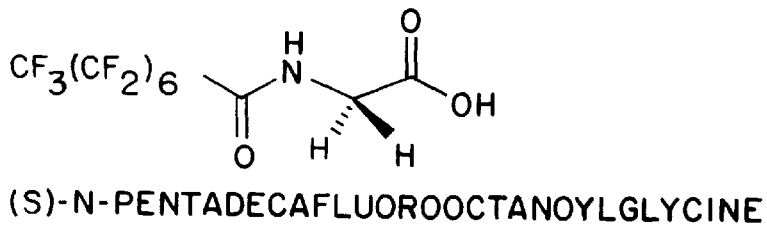
(S)-N-PENTADECAFLUOROOCTANOYLGLYCINE
FIG. 3AI

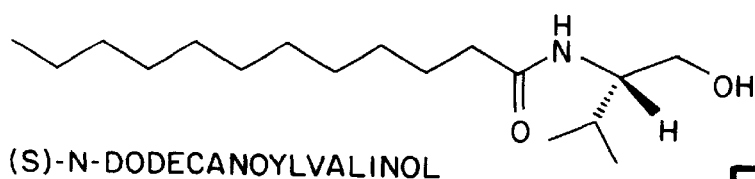
(S)-N-DODECANOYLVALINOL FIG. 3A2
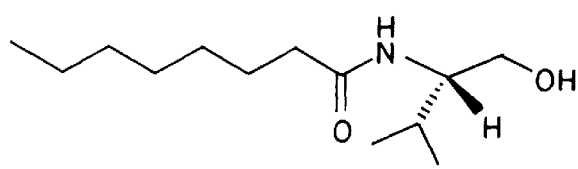
(S)-N-OCTANOYLVALINOL FIG. 3A3
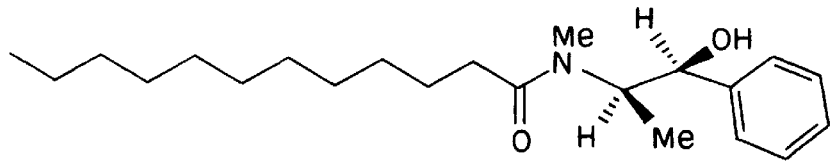
(1S,2R)-N-DODECANOYLEPHEDRINE FIG. 3A4
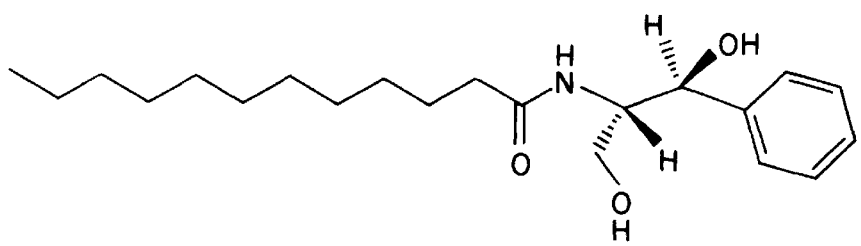
(1S,2R)-N-AMINO-1-PHENYL-1,3-PROPANEDIOLDODECANAMIDE
FIG. 3A5

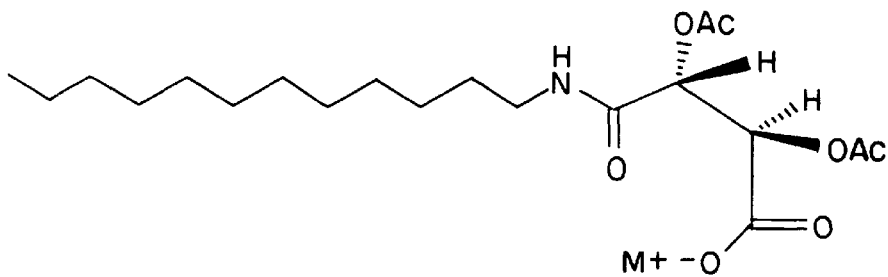
(R,R)-N-DODECYL-O,O'-DIACETYLTARTARIC ACID MONOAMIDE
(M=H, Et3NH+ OR GROUP 1 METAL)
FIG. 3A6
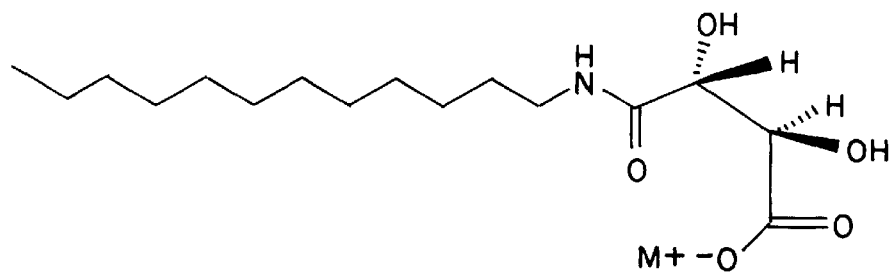
(R,R)-N-DODECYLTARTARIC ACID MONOAMIDE (M=H, Et3NH+ OR GROUP 1 METAL)
FIG. 3A7
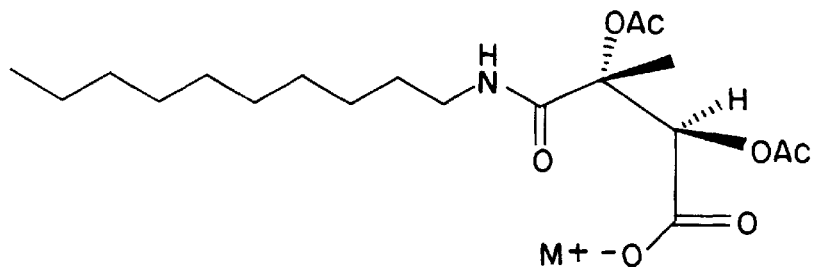
(R,R)-N-DECYL-O,O'-DIACETYLTARTARIC ACID MONOAMIDE
(M=H, Et3NH+ OR GROUP 1 METAL)
FIG. 3A8
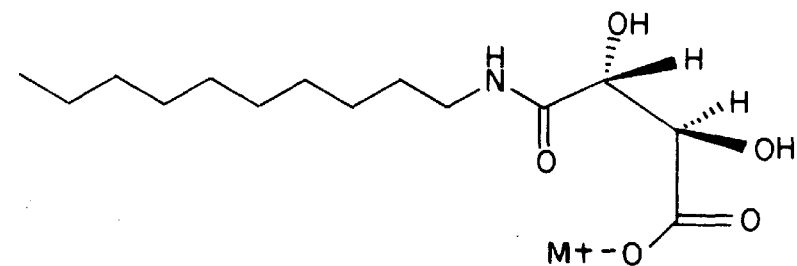
(R,R)-N-DECYLTARTARIC ACID MONOAMIDE
(M=H, Et3NH+ OR GROUP 1 METAL)
FIG. 3A9

(S)-N-DODECOXYCARBONYLALANINE
FIG. 3A10
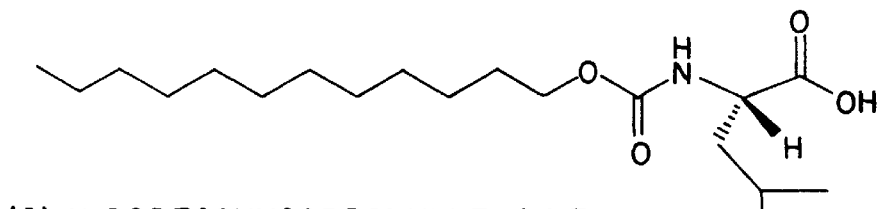
(S)-N-DODECOXYCARBONYLLEUCINE
FIG. 3A11
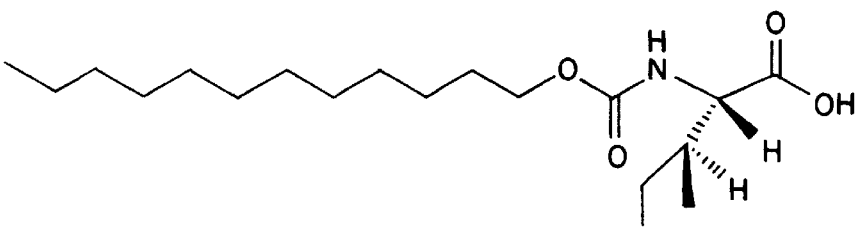
(2S,3S)-N-DODECOXYCARBONYLISOLEUCINE
FIG. 3A12
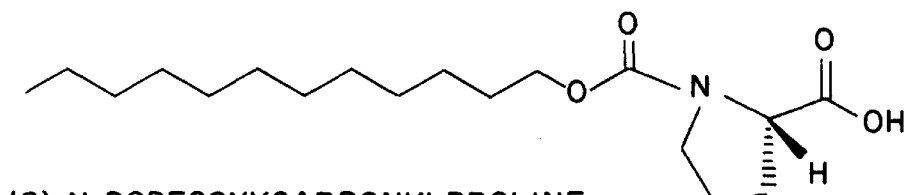
(S)-N-DODECOXYCARBONYLPROLINE
FIG. 3A13

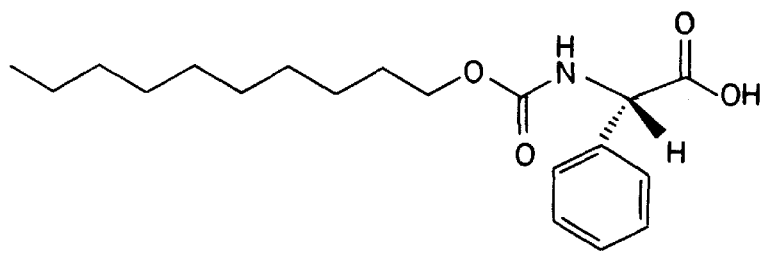
(S)-N-DECOXYCARBONYLPHENYLGLYCINE
FIG. 3A14
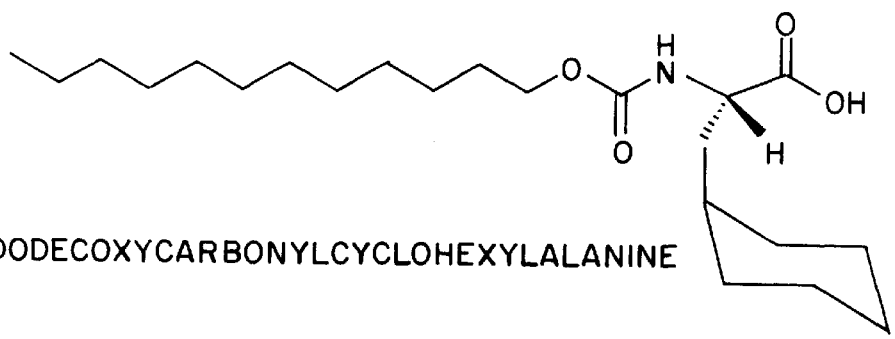
(S)-N-DODECOXYCARBONYLCYCLOHEXYLALANINE
FIG. 3A15
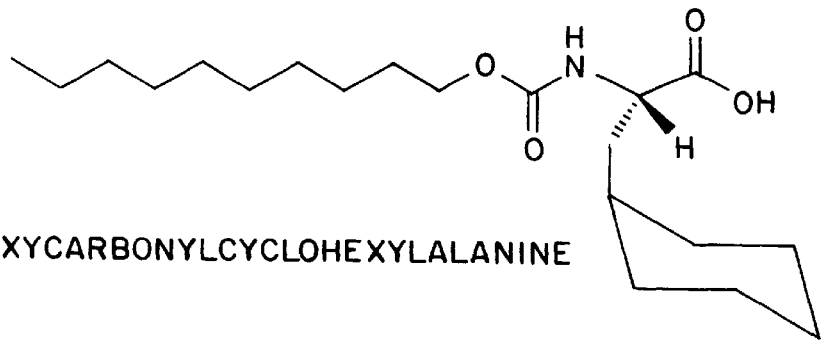
(S)-N-DECOXYCARBONYLCYCLOHEXYLALANINE
FIG. 3A16
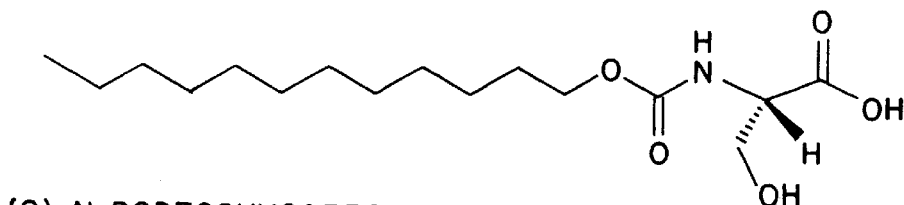
(S)-N-DODECOXYCARBONYLSERINE
FIG. 3A17

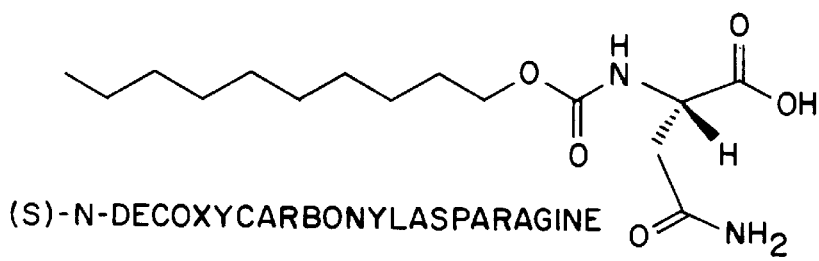
(S)-N-DECOXYCARBONYLASPARAGINE
FIG. 3A18
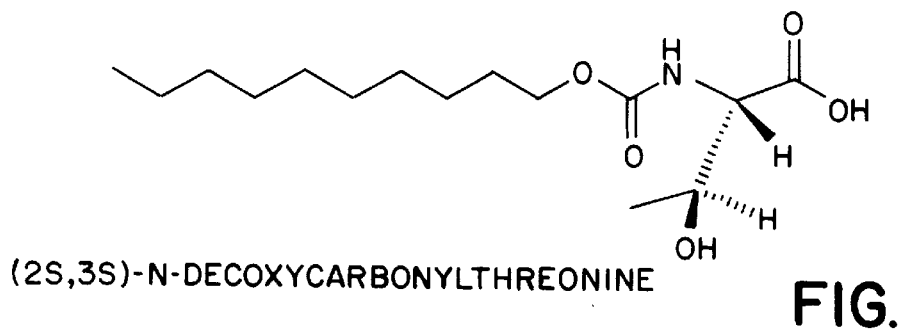
(2S,3S)-N-DECOXYCARBONYLTHREONINE
FIG. 3A19
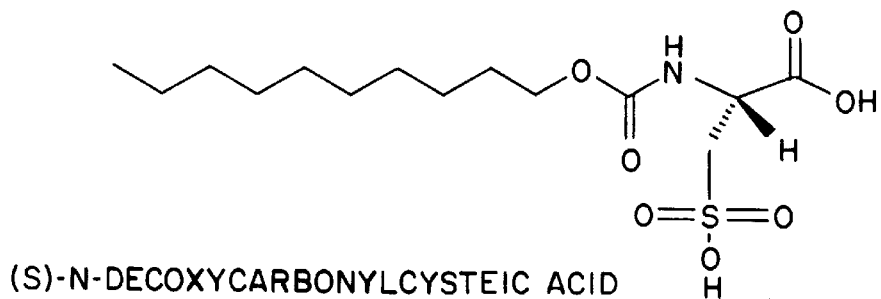
(S)-N-DECOXYCARBONYLCYSTEIC ACID
FIG. 3A20
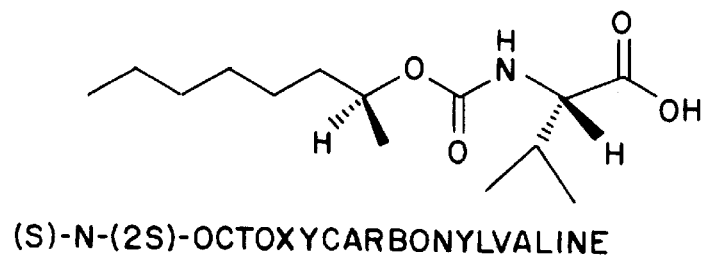
(S)-N-(2S)-OCTOXYCARBONYLVALINE
FIG. 3A21

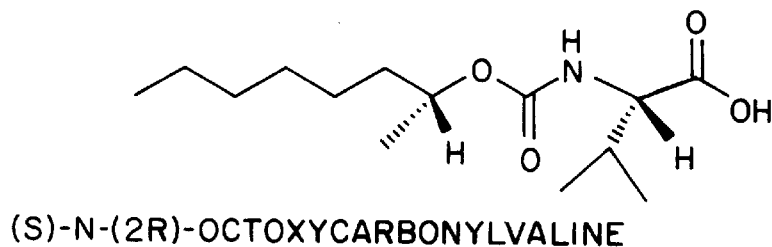
(S)-N-(2R)-OCTOXYCARBONYLVALINE
FIG. 3A22
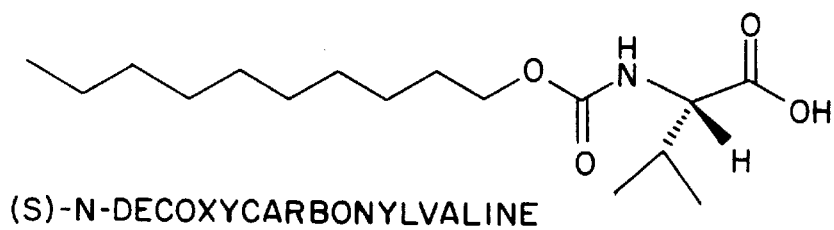
(S)-N-DECOXYCARBONYLVALINE
FIG. 3A23
(S)-N-OCTOXYCARBONYLVALINE
FIG. 3A24
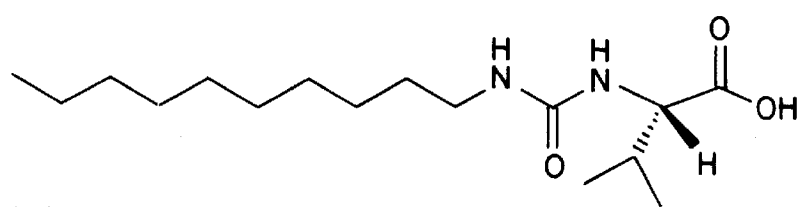
(S)-N-DECYLAMINOCARBONYLVALINE
FIG. 3A25

(S)-N-DODECANOYLLEUCINOL
FIG. 3A26
(S)-N-DODECANOYLISOLEUCINOL
FIG. 3B1
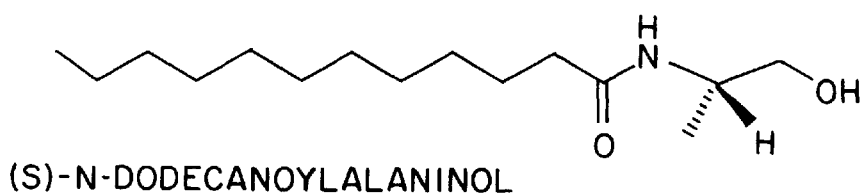
(S)-N-DODECANOYLALANINOL
FIG. 3B2
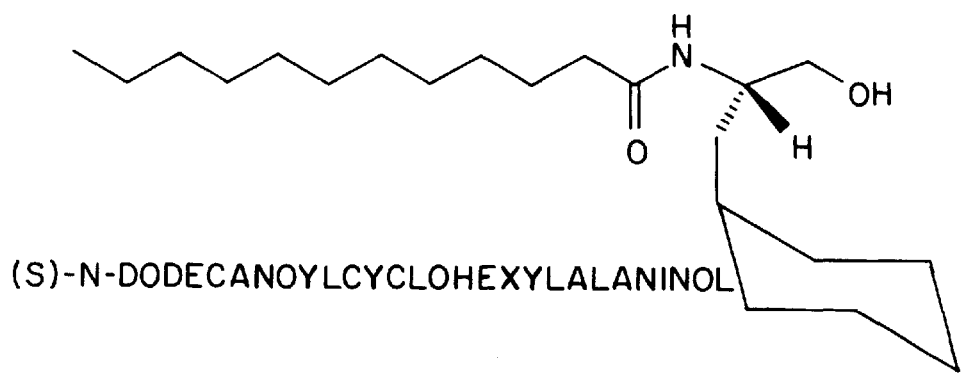
(S)-N-DODECANOYLCYCLOHEXYLALANINOL
FIG. 3B3

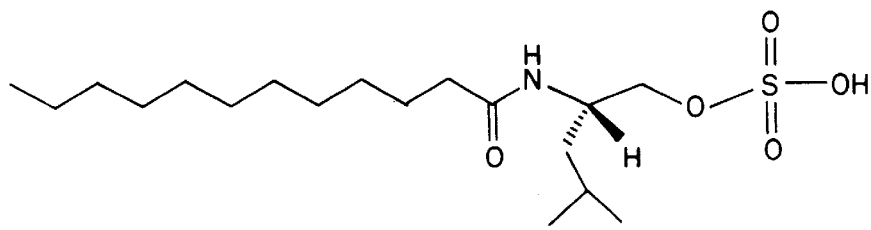
(S)-2-[(1-OXODODECYL)AMINO]-4-METHYL-1-SULFOOXYPENTANE
FIG. 3B4
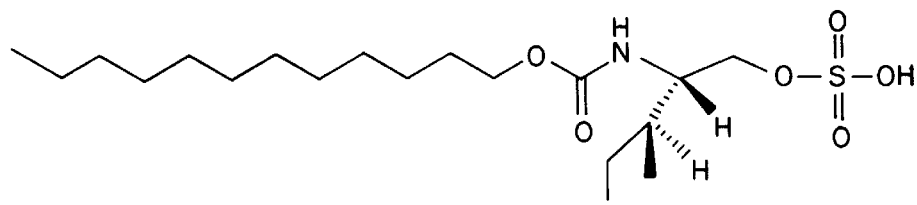
(S)-2-[(1-OXODODECYL)AMINO]-(3S)-METHYL-1-SULFOOXYPENTANE
FIG. 3B5
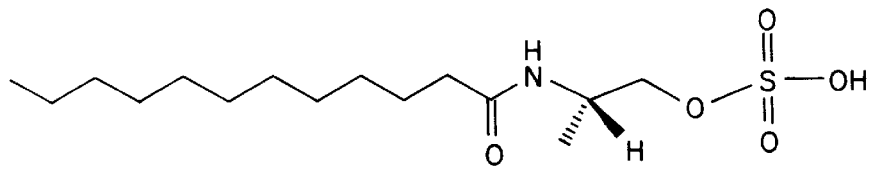
(S)-2-[(1-OXODODECYL)AMINO]-1-SULFOOXYPROPANE
FIG. 3B6
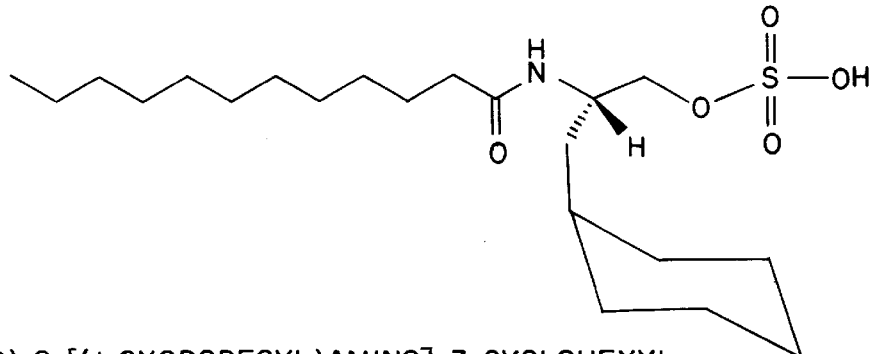
(S)-2-[(1-OXODODECYL)AMINO]-3-CYCLOHEXYL-
1-SULFOOXYPROPANE
FIG. 3B7

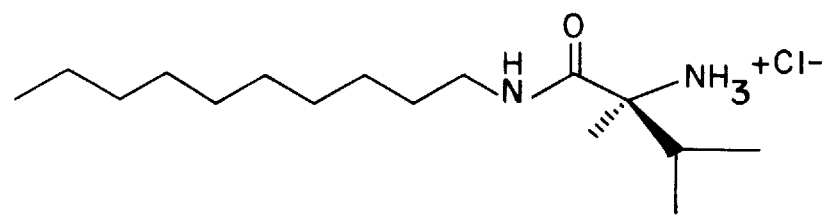
N-DECYL-(S)-VALINAMIDE HYDROCHLORIDE
FIG. 3B8
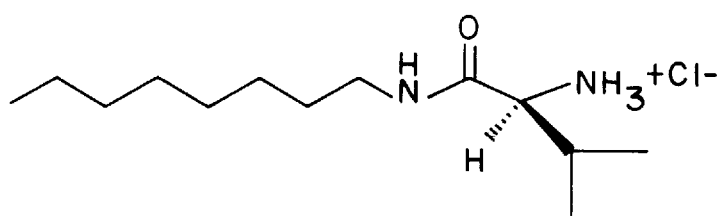
N-OCTYL-(S)-VALINAMIDE HYDROCHLORIDE
FIG. 3B9
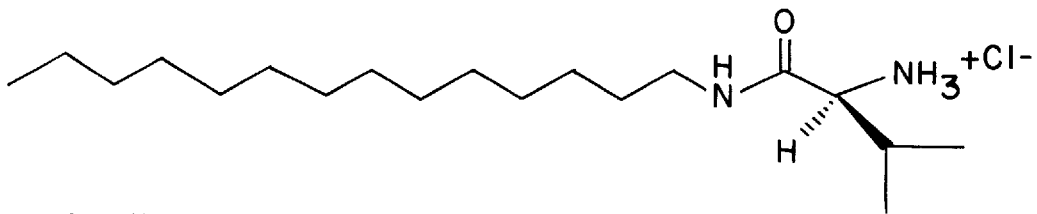
N-TETRADECYL-(S)-VALINAMIDE HYDROCHLORIDE
FIG. 3B10
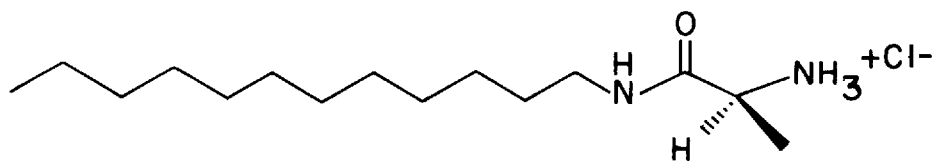
N-DODECYL-(S)-ALANINAMIDE HYDROCHLORIDE
FIG. 3B11

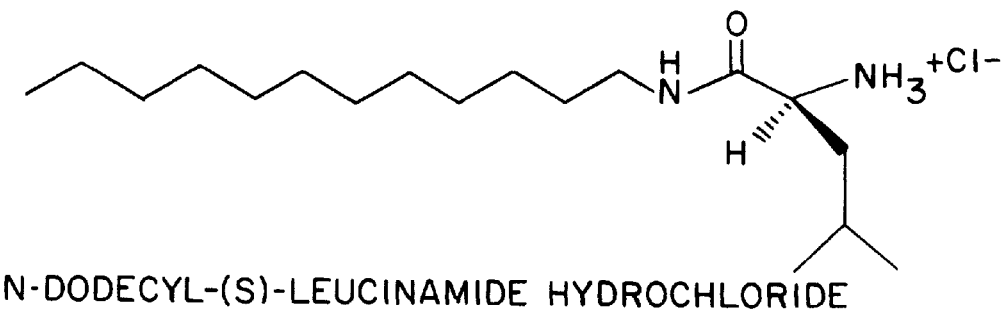
N-DODECYL-(S)-LEUCINAMIDE HYDROCHLORIDE
FIG. 3B12
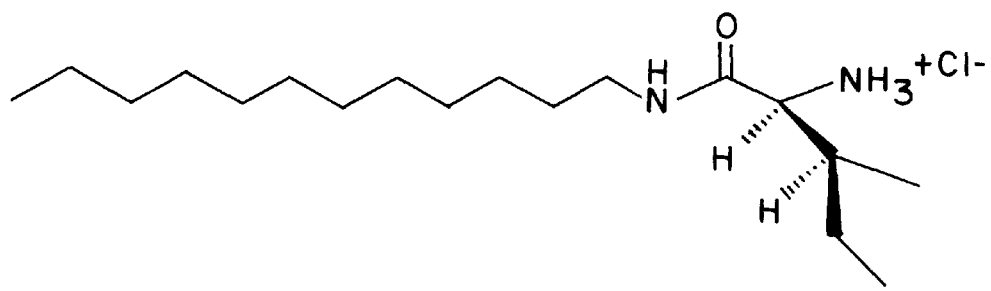
N-DODECYL-(S)-ISOLEUCINAMIDE HYDROCHLORIDE
FIG. 3B13
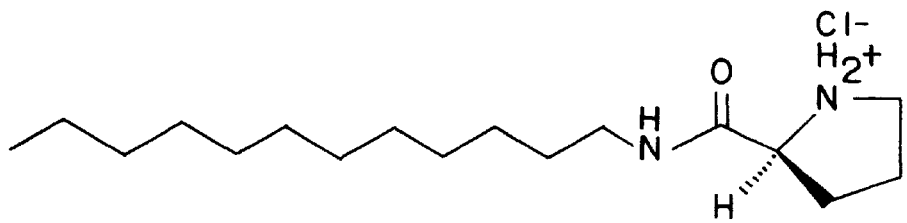
N-DODECYL-(S)-PROLINAMIDE HYDROCHLORIDE
FIG. 3B14

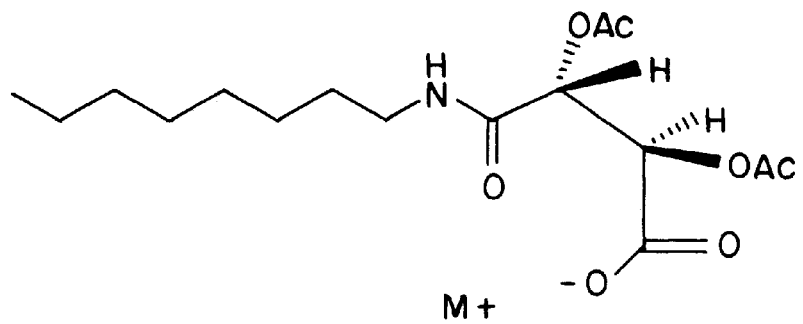
(R,R)-N-OCTYL-O,O-DIACETYLTARTARIC ACID MONOAMIDE
(M=H, Et3NH+, OR GROUP 1 METAL)
FIG. 3B15
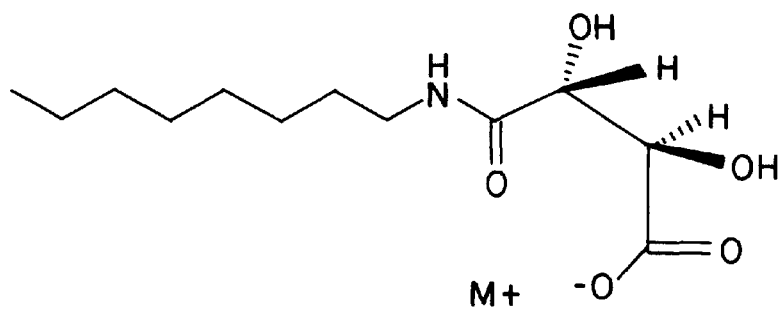
(R,R)-N-OCTYLTARTARIC ACID MONOAMIDE
(M=H, Et3NH+, OR GROUP 1 METAL)
FIG. 3B16

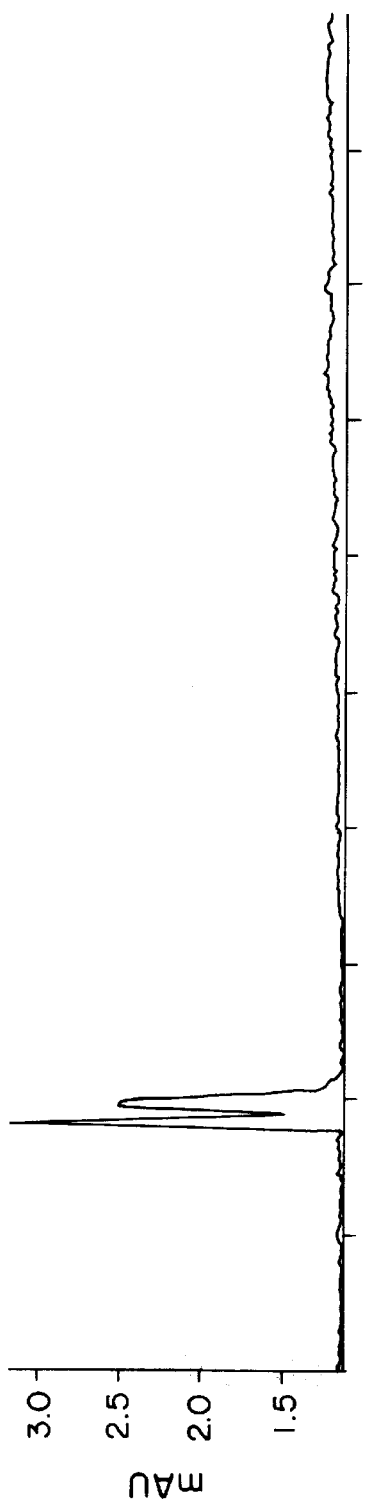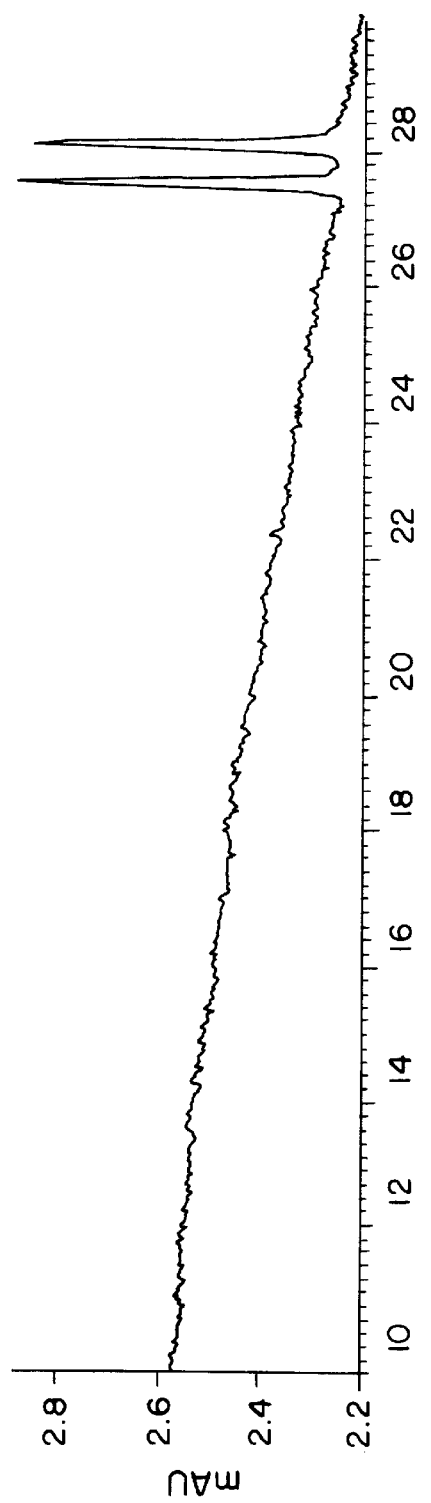

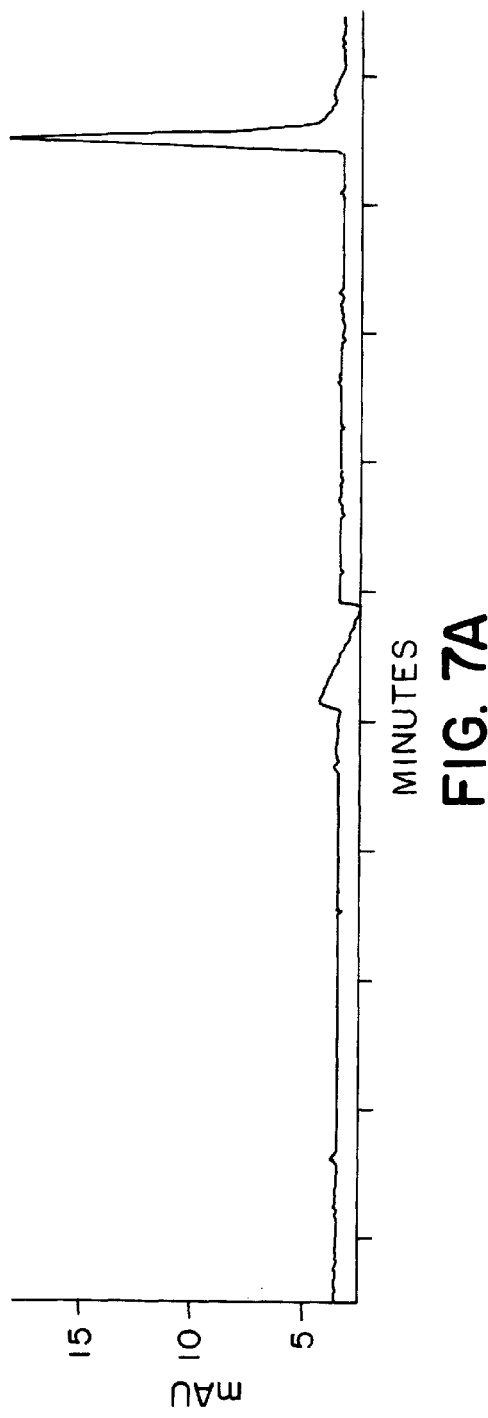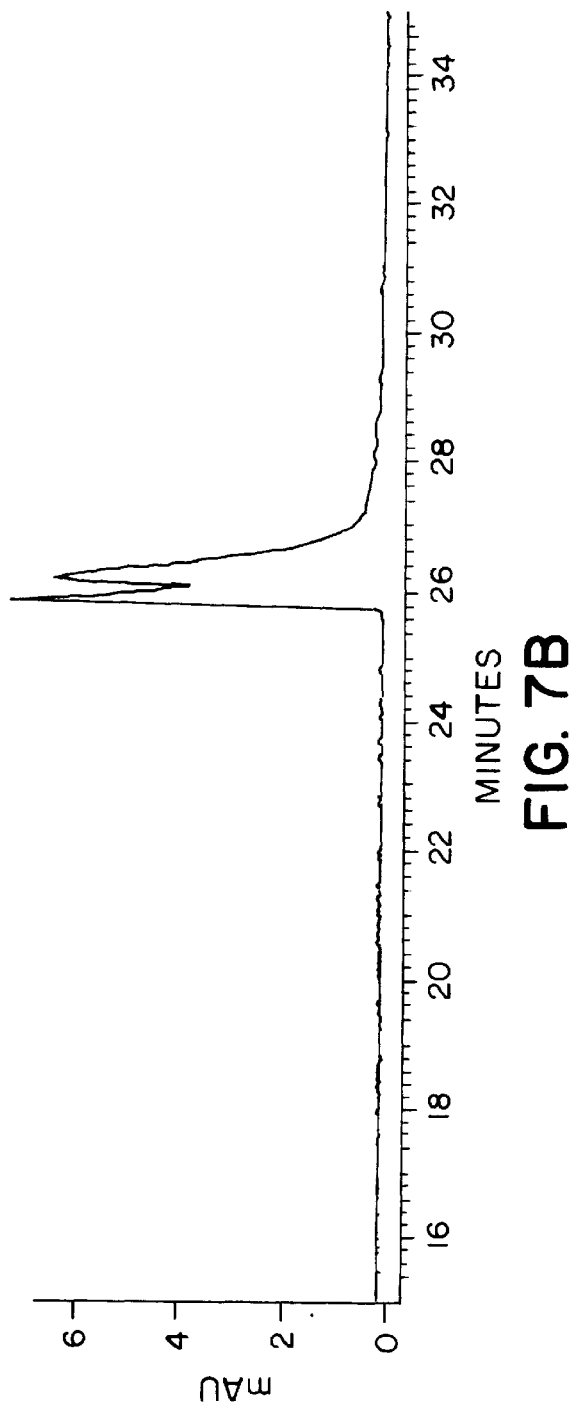
FIG. 7A
FIG. 7B

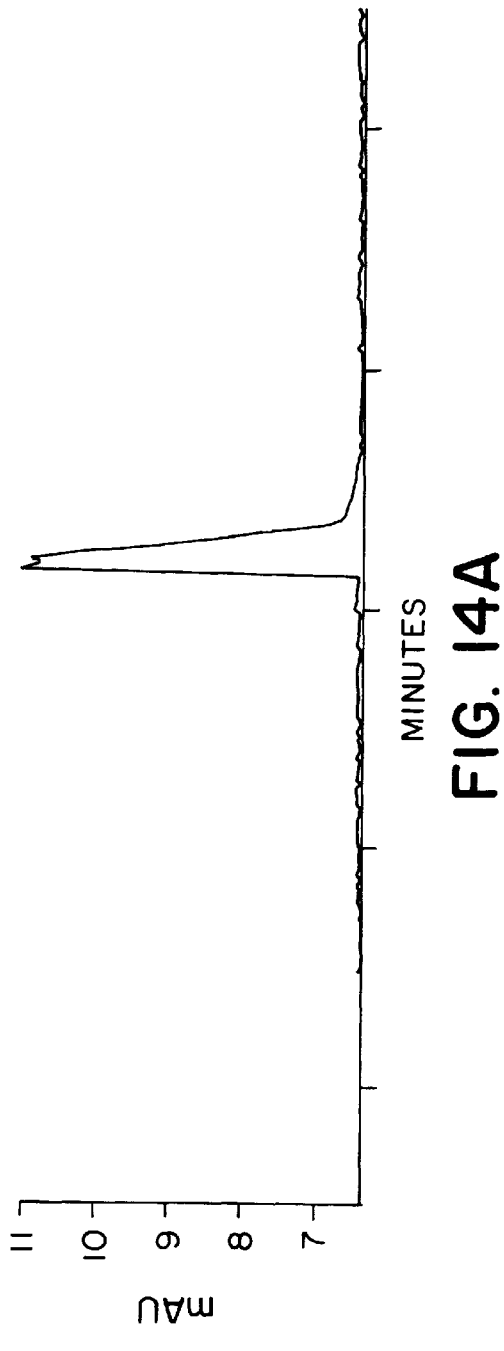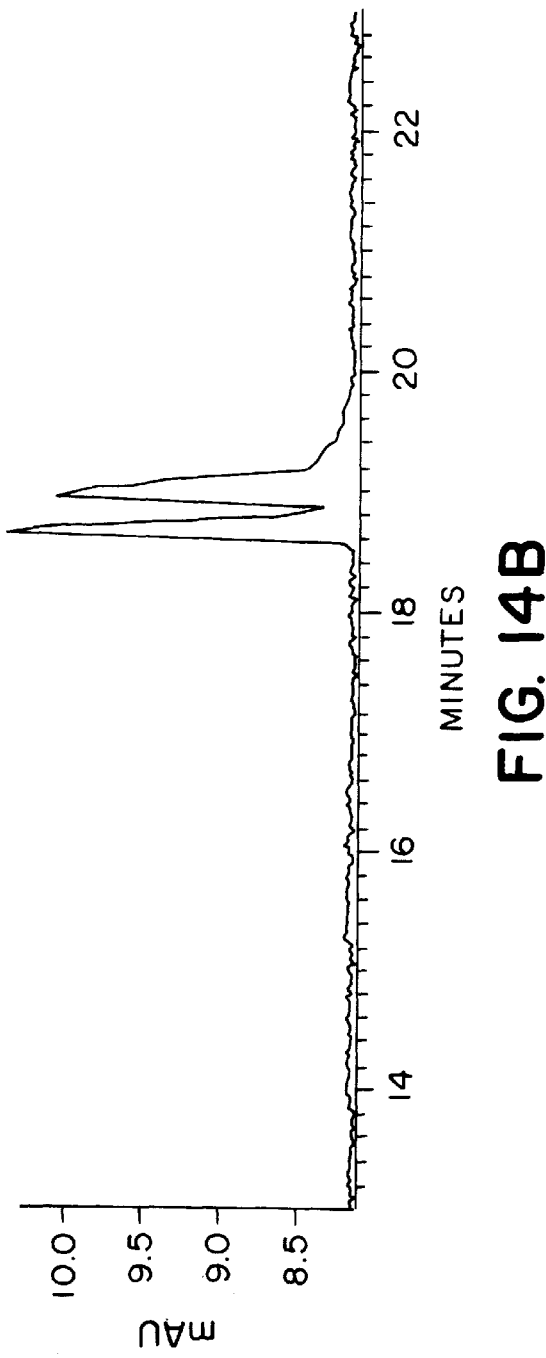

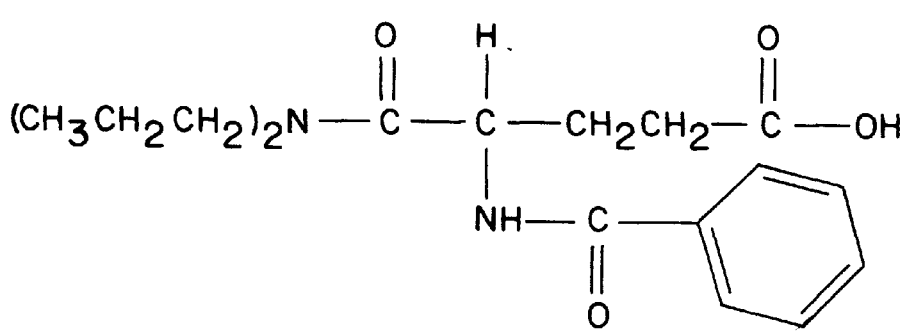
PROGLUMIDE
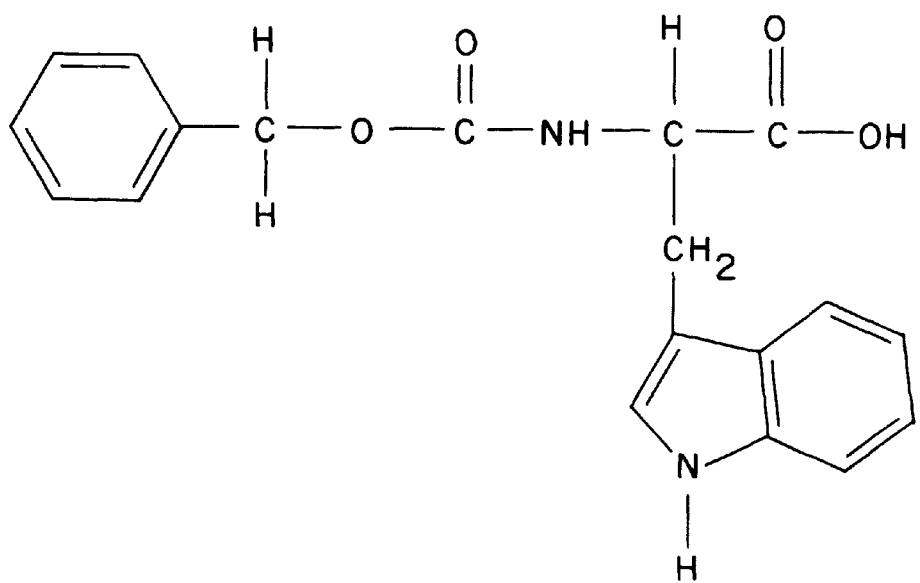
BENZYLOXYCARBONYLTRYPTOPHAN
FIG. 15

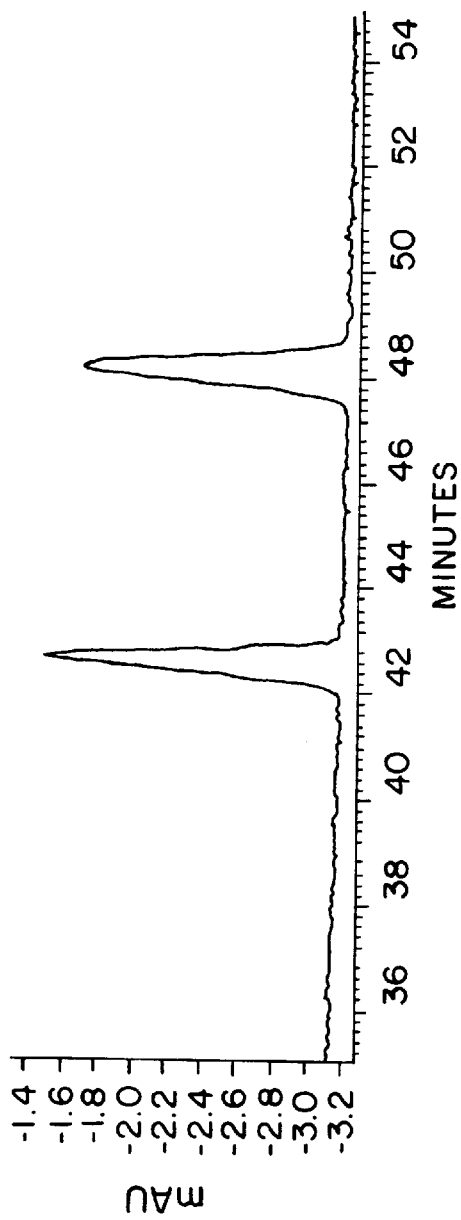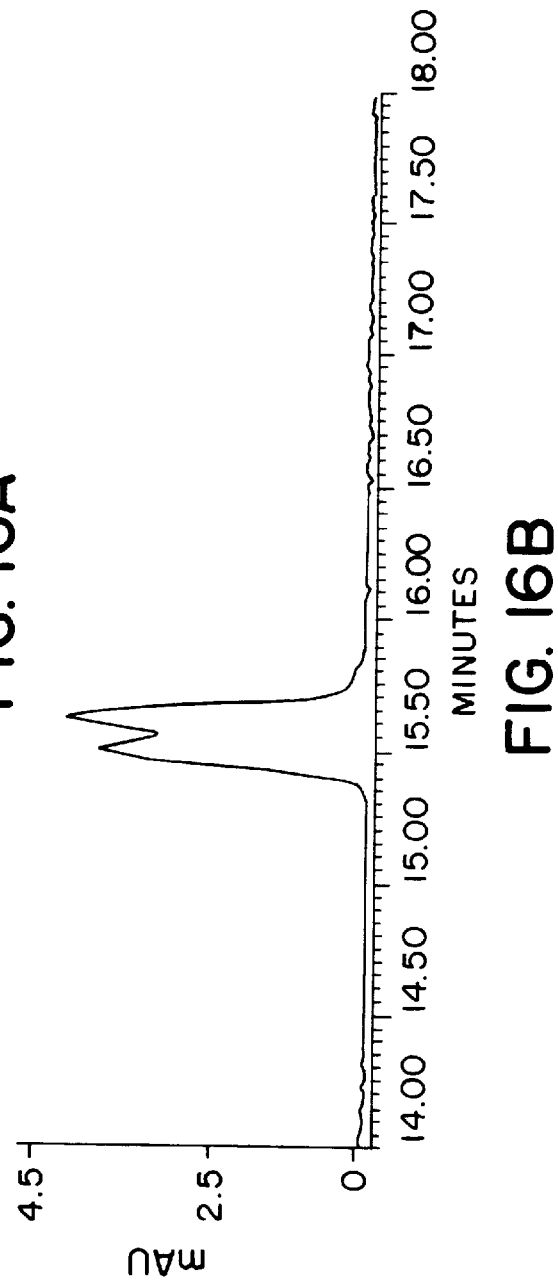

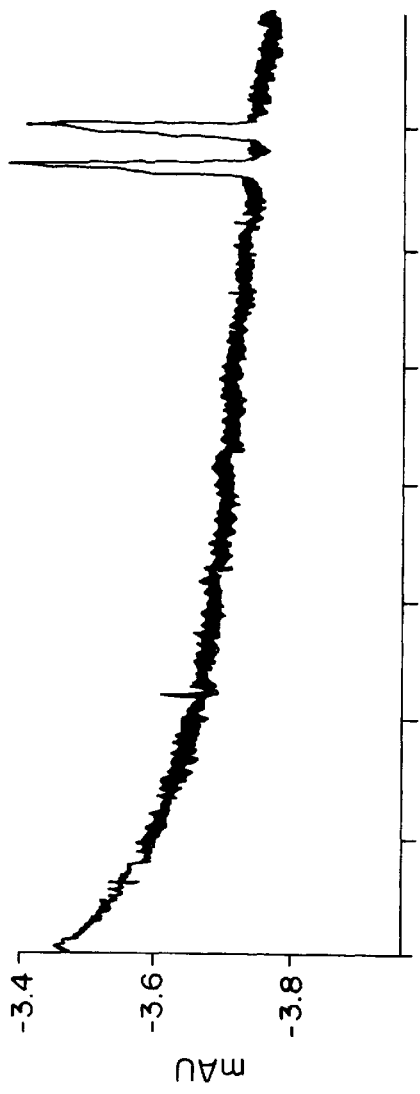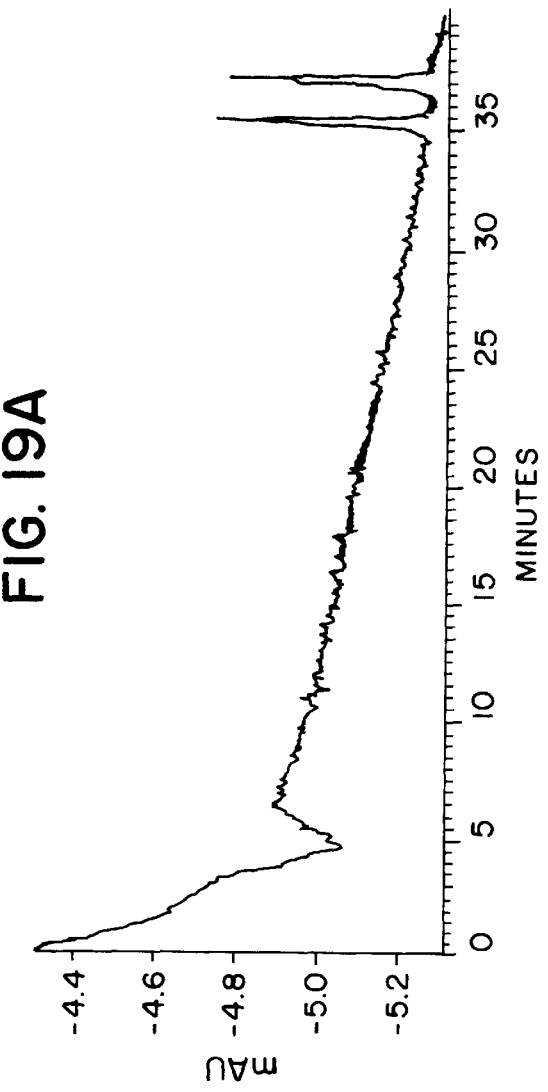
FIG. 19A
FIG. 19B

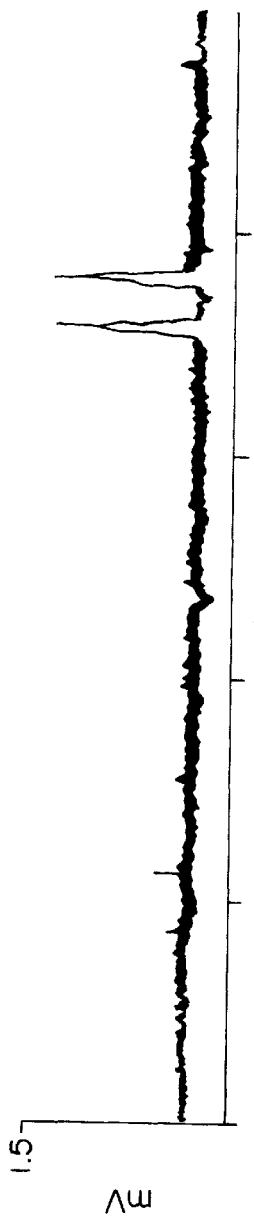
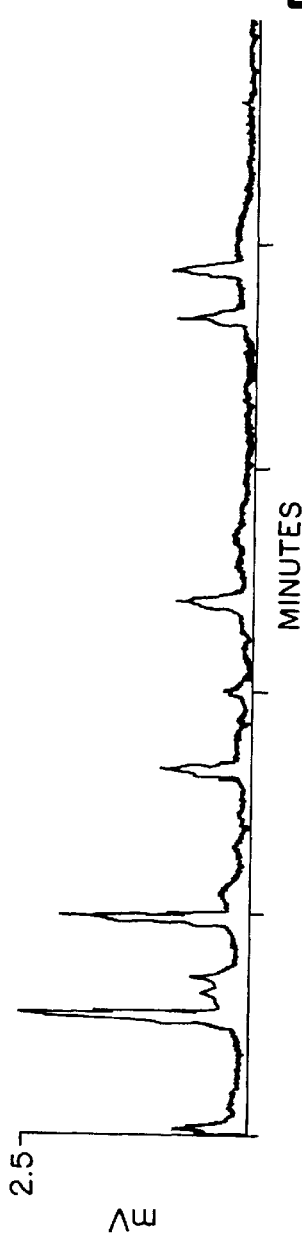
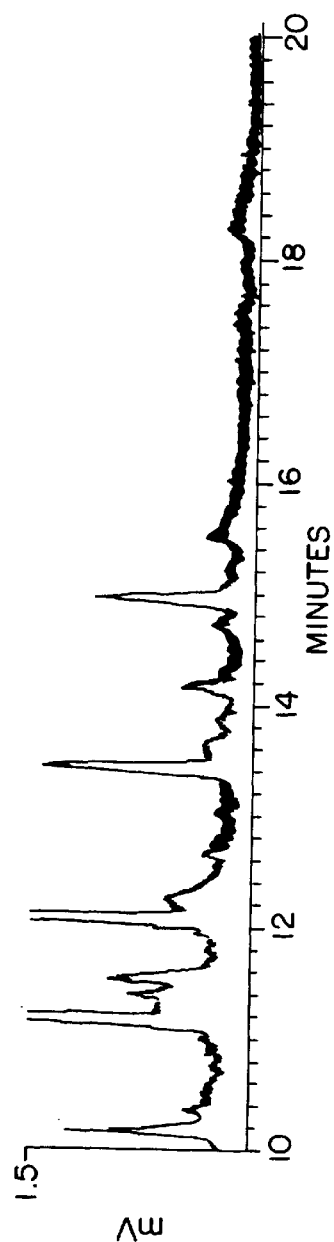
FIG. 21A
FIG. 21B
FIG. 21C

CHIRAL SURFACTANTS AND METHODS FOR THEIR USE IN CHIRAL SEPARATIONS

RELATED APPLICATION

This application is the U.S. National Phase of International Application No. PCT/US94/10644, filed on 20 Sep. 1994, which is a continuation-in-part application of U.S. Ser. No. 08/124,681 filed Sep. 20, 1993, the teachings of which are herein incorporated in their entirety by reference.

TECHNICAL FIELD

The invention is in the field of chromatography. In particular, the invention relates to improvements in the separation of chiral compounds by micellar electrokinetic capillary chromatography.

BACKGROUND ART

Capillary electrophoresis ("CE") is a well known separation technique that is of increasing interest to those concerned with separations. It is a modification of electrophoresis, typically practiced in a thin glass capillary instead of on a 2-dimensional surface such as paper or in a gel. This technique offers the benefits of high efficiency and resolution, rapid separations, the ability to analyze small sample amounts, and a desirable simplicity from the point of view of the apparatus required when compared to competing analytical techniques such as gel electrophoresis, gas chromatography, and liquid chromatography. As in all separation systems high resolution is the end objective and as in other systems resolution is a function of efficiency (theoretical plates) and selectivity (Weinberger, R. "Practical Capillary Electrophoresis", Academic Press, San Diego, Calif. 1993).

The benefits of capillary electrophoresis derive to a large extent from the use of narrow diameter capillary tubes, which permit efficient removal of the heat generated in the separation process. This heat removal prevents convective mixing which would degrade the separating power. The narrow diameter tubes also allow high voltages to be used to generate the electric field in the capillary while limiting current flow and hence heat generation.

A CE separation begins by filling the capillary with a supporting electrolyte. Next, a small amount of sample is injected into one end of the capillary. Typical sample injection volumes range from 1–20 nanoliters. After sample injection, a high voltage is applied to the capillary and the sample components are separated on the basis of different charge/mass ratios. A capillary electrophoretic separation can also be augmented with a bulk fluid flow, called electroosmotic flow. If present, it moves all components through the capillary tube at the same rate, and generally does not contribute to the resolution of different sample components. Eventually, the sample components move through an appropriate detector, such as a UV detector. This can provide detection and quantitation of each separated sample zone.

A micelle is a colloidal particle formed from surfactant molecules. The practice of capillary electrophoresis in the presence of micelles is commonly referred to as micellar electrokinetic chromatography (Terabe, S., Otsuka, K., Ichikawa, K., Tsuchiya, A. and Ando, T. Analytical Chemistry, 1984, (56) 111–113; Terabe, S., Otsuka, K., and Ando, T. Analytical Chemistry, 1985, (57)834–841). This term will be used to refer to both micellar electrophoretic separations, (separations where the electroosmotic flow is negligible), and micellar electrokinetic separation (separations where the electroosmotic flow impacts the separation time). The equations for retention and resolution in MEKC are shown as equations 1 and 2 (Terabe, S., et al. supra).

$$k = \frac{t_r - t_0}{t_0\left(1 - \frac{t_r}{t_{mc}}\right)} \qquad \text{equation 1}$$

where $t_r$=retention time of the solute
$t_o$=retention time of solute in the absence of micelles
$t_{mc}$=micelle retention time
and k is the solute's capacity factor.

$$Rs = \left(\frac{N^{\frac{1}{2}}}{4}\right)\left(\frac{\alpha - 1}{\alpha}\right)\left(\frac{k_2}{k_2 + 1}\right)\left(\frac{k_2}{k_2 + 1}\right)\left(\frac{1 - \frac{t_0}{t_{mc}}}{1 + \frac{t_0}{t_{mc}}k_1}\right) \qquad \text{equation 2}$$

where N=efficiency (theoretical plates)
$\alpha$=selectivity.

Equation 3 is the resolution equation for HPLC, with all terms as previously defined.

$$Rs = \left(\frac{N^{\frac{1}{2}}}{4}\right)\left(\frac{\alpha - 1}{\alpha}\right)\left(\frac{k_2}{k_2 + 1}\right) \qquad \text{equation 3}$$

The resolution equation for MEKC is very similar to the resolution equation for HPLC. In fact, as $t_{mc}$ approaches infinity, the equations become identical (equation 3). Considering the case where $t_{mc}$ or $t_o$ equals infinity, one can easily se the difference between HPLC and MEKC. The practical difference between HPLC and MEKC is related to the efficiency term of the resolution equation. In HPLC a typical value of N (theoretical plates) is 5000 while a typical value of N for MEKC is 100,000. In quantitative terms a widely accepted goal for resolution of two peaks is a value of 1.5. Assuming k'=1, then the resolution requirement of 1.5 requires an alpha value of 1.20 for the HPLC case. However, the much higher efficiency of MKC determines that a much smaller alpha of 1.04 achieves the same resolution of 1.5. Thus, if the small alphas associated with many partial HPLC separations could be achieved in an MEKC system, useful resolutions would result. (Note that because resolution depends on the term $((\alpha-1)/\alpha)$, an alpha of 1.04 provides twice the resolution of an alpha of 1.02).

Chiral separations have been accomplished using a variety of techniques. Over the last thirty years investigators have shown that chiral separations are possible using gas chromatography (GC) and liquid chromatography (LC) (Zief, M. and Crane, L. J., Editors, "Chromatographic Chiral Separations" Marcel Dekker, Inc., New York. Basel, 1988), gel electrophoresis (Barton, J. K., J. Biomolecular Structure and Dynamics, 1983, (1) 621–632), paper electrophoresis (Fanali, S., Cardaci V., Ossicini, L., J. Chromatogr. 1983, (165) 131–135) and capillary electrophoresis (CE) (Snopek, J., Jelinek, I. and Smolkova-Keulemansova, E. Journal of Chromatography, 1992, (609) 1–17). These separations are based on the ability of the enantiomers of the sample to differentially interact with a chiral phase that is part of the separation system.

The chiral phase can be embodied in a variety of ways. In chromatography, the chiral phase is conventionally part of the stationary phase, or column. In both GC and LC, a wide variety of chiral columns are available. The adsorption of the enantiomers by the stationary phase is the sum of both achiral and chiral interactions. The achiral interactions might include ionic, hydrogen bonding, and hydrophobic adsorption. The chiral interactions are derived from the spatial relationship of the achiral interactions. The energy difference contributed by this chiral interaction is the basis for the chiral separation.

The efficiency of the current generation of chiral chromatographic systems is generally low, thus the difference in the free energy of the interaction between the chiral modifier and the enantiomers must be relatively large in order to gain adequate resolution. This large energy difference requirement contributes to the low efficiency of many chiral HPLC systems (5000 to 10000 plates), and the tailing peaks observed on many chiral columns. This large energy difference requirement also prevents chiral HPLC columns from being of general use. Currently, chiral HPLC columns are selective for small classes of compounds, so more than fifty chiral phases have been commercialized. In this environment, method development is highly empirical and very tedious. Chiral separations per se have little novelty today, the challenge being to create systems which separate larger classes of enantiomers or provide easier method development.

In conventional gel electrophoresis, a chiral phase may be created by adding a chiral modifier to the gel buffer, or by covalent attachment of the modifier to the gel matrix (Barton, J. K., J. Biomolecular Structure and Dynamics, 1983, (1) 621–632). The separation occurs, as in chromatography, through a differential interaction of the individual enantiomers with the chiral phase. In gel electrophoresis, this results in a change in the overall electrophoretic mobilities of the two chiral molecules. As the two enantiomers move through the gel at different velocities, the separation is effected. Because the presence of the gel severely reduces bulk fluid movement, the osmotic flow that is commonly found in electrophoretic separations is minimized. Therefore, the final chiral separation is due largely to the change in electrophoretic mobility of the two enantiomers.

One of the major potential advantages of CE for chiral separations is the relatively high efficiency of the technique. This high efficiency permits the use of chiral modifiers that create only a small difference in free energies between the two enantiomers and the modifier. In CE the chiral phase is generally added to the supporting electrolyte. As in conventional gel electrophoresis, the two enantiomers bind differentially to the chiral modifier, resulting in a change in the electrophoretic mobilities. The resulting difference between the mobilities of the two enantiomers results in their separation. Although electroosmotic flow may sometimes be present in CE separations, it generally does not contribute significantly to the quality of the chiral separation.

Chiral CE separations were first disclosed in 1985 (Zare, R. N. and Gassmann, E. U.S. Pat. No. 4,675,300 Jun. 23, 1987), and a few samples have now been analyzed. However, the present art does not allow useful separations of a wise variety of compounds—it suffers from the same limitations as chiral HPLC separations; tedious method development and narrow selectivity. All separation shave been accomplished through the addition of a chiral modifier to the supporting electrolyte. The kind of chiral modifiers used fall into three categories. The first if the use of amino acid/metal complexes (Zare, R. N. and Gassmann, E. U.S. Pat. No. 4,675,300, Jun. 23, 1987; Gassmann, E., Kuo, J. E. and Zare, R. N. Science, 1985, (230) 813–814; Gozel, P., Gassmann, E., Michelsen, H and Zare, R. N. Analytical Chemistry, 1987, (59) 44–49). This type of complex is highly water soluble, and works well for chiral amino acid separations. This system has previously been shown to work using LC as well as gel electrophoresis for the same sample set. The second category of chiral modifiers is a class of carbohydrates called cyclodextrins (Guttmann, A., Paulus, A., Cohen, A. S., Grinberg, N. and Karger, B. L. Journal of Chromatography, 1988, (448) 41–53; Fanali, S. Journal of Chromatography, 1989, (474) 441–446). These modifiers are also highly water soluble, and are also employed extensively in LC. The third category of chiral modifiers are chiral detergents (Cohen, A. S., Paulus, A. and Karger, B. L. Chromatographia, 1987, (24) 15–24; Dobashi, A., Ono, T., Hara, S. and Yamaguchi, J. Analytical Chemistry, 1989, (61) 1984–1986; Terabe, S., Shibata, M. and Miyashita, Y. Journal of Chromatography, 1989, (480) 403–411).

The chiral detergent (S)-N,N-didecylalanine has been used with sodium dodecyl sulfate micelles and copper complexation to effect chiral separations (Cohen, A. S., Paulus, A. and Karger, B. L. Chromatographia, 1987, (24) 15–24). The chiral separation mechanism is based on ligand exchange as in the system reported by Zare, supra. The use of chiral detergents in the supporting electrolyte above their critical micelle concentration is art that has been practiced both with the use of sodium dodecanoylvaline (Dobashi, A., Ono, T., Hara, S. and Yamaguchi, J. Analytical Chemistry, 1989, (61) 1984–1986; Dobashi, A., Ono, T., Hara, S. and Yamaguchi, J. Journal of Chromatography, 1989, (480) 413–420), as well as with the use of bile salts (Terabe, S., Shibata, M. and Miyashita, Y. Journal of Chromatography, 1989, (48) 403–411). The micelle formed from these detergents is a structure composed of many individual detergent molecules. The inside of the micelle is generally a hydrophobic environment, much like the hydrophobic layer of a reversed phase chromatographic packing. The outside of the micelle presents hydrophilic groups that are often ionic, resulting in water solubility of the micelle particle. Somewhere in the surfactant there is a chiral center or centers which confer chirality to the micellar environment.

The present art of CE and in particular MEKC is similar to the HPLC art in that none of the systems have been shown to have broad applicability. Zare et al. have shown amino acid separations based on copper complexes which are well known from both chiral electrophoretic separations and chiral HPLC separations and are not useful for most other types of compounds. Cyclodextrin separations are restricted to molecules that can interact with the cyclodextrin cavity. Chiral MEKC separations have not been shown for acidic compounds nor for a range of compounds of a given class. Sodium dodecanoylvaline, as reported by Hara, has allowed chiral separations of neutral amino acid derivatives as well as a few other neutral compounds. Successful separation of organic bases or acids has not been demonstrated with this chiral surfactant. Bile salts have only been able to show chiral separation of analytes with very rigid structures containing fused ring systems.

DISCLOSURE OF THE INVENTION

The invention provides a set of chiral surfactants and methods for their use, that are used in conjunction with capillary electrophoresis hardware for the purpose of effecting chiral separations. This invention provides a simple, efficient, and high speed methodology with good resolution, high sensitivity, and easy methods development for effectively separating a wide variety of chiral compounds. As such, this invention may, for the first time, provide a universal method of separating any chiral compound without having to resort to specialized stationary phase columns for difficult separations.

In accordance with the preferred embodiment of this invention, chiral surfactants are defined as being composed of the following parts. First, a chiral selector. This may be any amino acid, or derivative thereof, or an amino alcohol or tartaric acid derivative. It functions to interact with chiral molecules. Second, a hydrophilic head group that is linked to the chiral selector that confers overall solubility to the micelle, and may also potentiate (increase) enantioselectivity. Third, a "linker" group that links the tail to the chiral selector. This "linker" group is also used to potentiate the chiral selectivity of the chiral selector. Fourth, a hydrophobic carbon chain or tail. The chain length may vary, and may exist in linear, branched, substituted, or other forms, so long as is exhibits hydrophobicity and/or functions to partition the analyte into the chiral surfactant molecule. The tail may also potentiate the chiral selectivity of the chiral selector.

The invention is directed to a chiral surfactant having the general formula:

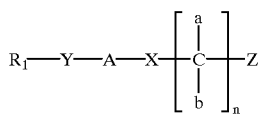

wherein
$R_1 = C_4-C_{18}$ linear alkyls, $C_4-C_{18}$ branched alkyls, $C_4-C_{18}$ halogen-substituted linear alkyls, $C_4-C_{18}$ polyether hydrocarbons, $C_4-C_{18}$ alkyls having a chiral center, all alkyls optionally being unsaturated, and cholesterolic hydrocarbons.

$A=NH, CO, SO$ or $SO_2$; $Y=O, NH$ or $CH_2$; $X=CO, O$ or $NH$; $C=$carbon, $a \neq b$, and n may be from 1 to 5.

$Z=COO^-, SO_4^-, SO_3^-, PO_3^-, PO_4^-, NR'_3{}^+, PR'_3{}^+, —OH$ polyethers, zwitterions, polyalcohols;

$R'=H$ or $C_1-C_4$ linear or branched hydrocarbon, optionally halogenated, optionally unsaturated; and when $R_1$ is a linear hydrocarbon, and $Y=CH_2$, $A=CO$, $X=NH$, $Z=COO^-$ and a or $b=H$ but$\neq b$, then a or $b \neq$methyl or isopropyl.

The invention is also directed to a chiral surfactant having the general formula:

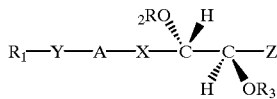

wherein
$R_1 = C_4-C_{18}$ linear alkyls, $C_4-C_{18}$ branched alkyls, $C_4-C_{18}$ halogen-substituted linear alkyls, $C_4-C_{18}$ polyether hydrocarbons, $C_4-C_{18}$ alkyls having a chiral center, all alkyls optionally being unsaturated, and cholesterolic hydrocarbons;

R2, R3=H or C1–C8 linear or branched alkyl or alkenyl hydrocarbons;

$Y=CH_2$; $A=NH$; $X=CO$; $C=$carbon;

$Z=COO^-, SO_4^-, SO_3^-, PO_3^-, PO_4^-, NR'_3{}^+, PR'_3{}^+, —OH$, polyethers, zwitterions, polyalcohols; and $R'=H$ or $C_1-C_4$ linear or branched hydrocarbon, optionally halogenated, optionally unsaturated.

Also included in the invention is a chiral surfactant having the general formula:

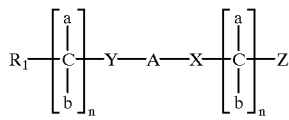

wherein
$R_1 = C_4-C_{18}$ linear alkyls, $C_4-C_{18}$ branched alkyls, $C_4-C_{18}$ halogen-substituted linear alkyls, $C_4-C_{18}$ polyether hydrocarbons, $C_4-C_{18}$ alkyls having a chiral center, all alkyls optionally being unsaturated, and cholesterolic hydrocarbons.

$R'=H$ or $C_1-C_4$ linear or branched hydrocarbon, optionally halogenated, optionally unsaturated;

$Y=O, NH$ or $CH_2$; $A=CO, So$ or $SO_2$; $X=O, HN$; $a \neq b$, and n may be from 1 to 5; and $Z=COO^-, SO_4^-, SO_3^-, PO_3^-, PO_4^-, NR'_3{}^+, PR'_3{}^+, —OH$, polyethers, zwitterions, or polyalcohols.

The invention is also directed to a chiral surfactant comprising:

a chiral selector, said chiral selector having at least one chiral center;

a hydrophilic head group bonded to said chiral selector, which in combination with said chiral selector potentiates the chiral selectivity of said chiral surfactant sufficiently to effect substantial separation of a chiral compound;

a linker bonded to said chiral selector which in combination with said chiral selector potentiates the chiral selectivity of said chiral surfactant sufficiently to effect substantial separation of a chiral compound; and a hydrophobic tail bonded to said linker, which in combination with said chiral selector potentiates the chiral selectivity of said chiral surfactant sufficiently to effect substantial separation of a chiral compound.

The head group is selected from the group consisting of quaternary ammoniums, ammomium salts, carboxylates, alcohols, sulfates, sulfonic acids, polyalcohols, zwitterions, and the respective salts thereof. Representative sulfate head groups are included in: (S)-2-[(1-oxododecoxy)amino]-3-methyl-1-sulfooxybutane. Carboxylate head groups are included in: (S)-N-dodecoxycarbonylvaline; (R)-N-dodecoxycarbonylvaline; (S)-N-dodecoxycarbonyl-tert-leucine; (S)-N-tetradecoxycarbonylvaline; and (S)-N-dodecoxycarbonylphenylglycine. Alcohol head groups are included in: (S)-N-dodecanoylvalinol; (S)-N-dodecylaminocarbonylvalinol; and (S)-N-dodecoxycarbonylvalinol.

Chiral selectors are selected from the group consisting of amino acids, amino alcohols, and tartrates, and the salts thereof. Some representative compounds of this invention that demonstrate amino acids as chiral selectors are: (S)-N-Dodecoxycarbonylserine, (S)-N-Dodecoxycarbonylalanine, (S)-N-Dodecoxycarbonylleucine, and (S)-N-Dodecosycarbonylproline. Some representative compounds of this invention that demonstrate amino alcohols as chiral selectors are: (S)-N-dodecanoylvalinol; (1S,2R)-N-dodecanoylephedrine; (1S,2R)-N-amino-1-phenyl-1,3-propanedioldodecanamide; and (S)-2-[(Oxododecyl)amino]-3-methyl-1-sulfooxybutane. Some representative compounds of this invention that demonstrate tartaric acid derivatives as chiral selectors are: (R,R)-N-dodecyl-O,O'-diacetyltartaric acid monoamide; (R,R)-N-dodecyltartaric acid monoamide; (R,R)-N-decyl-O,O'-diacetyltartaric acid monoamide; and (R,R)-N-decyltartaric acid monoamide.

This invention is also directed to chiral surfactants wherein the linker is selected from the group consisting of amides, carbamates, sulphonamides, and ureas. Carbamate-containing linkers include: (S)-N-dodecoxycarbonylvaline; (R)-N-dodecoxycarbonylvaline; (S)-N-dodecoxycarbonyl-tert-leucine; (S)-N-tetradecoxycarbonylvaline; and (S)-N-dodecoxycarbonylphenylglycine. Sulphonamide-containing linkers include: (S)-N-dodecylsulfonylvaline. Urea-containing linkers include: (S)-N-dodecylaminocarbonylvaline; and (S)-N-dodecylaminocarbonylvalinol. Amide-containing linkers include (R,R)-N-Decyltartaric acid monoamide, (S)-2-[(1-oxododecyl)amino]-3-methyl-1-sulfoxybutane, and N-Dodecyl-(S)-leucinamide hydrochloride.

This invention also includes chiral surfactants wherein the tail is selected from the group consisting of linear alkyls, substituted linear alkyls, linear alkenyls, substituted linear alkenyls, cholesterolic, and polyether hydrocarbons, including $C_4$–$C_{18}$ linear alkyls, $C_4$–$C_{18}$ branched alkyls, $C_4$–$C_{18}$ halogen-substituted linear alkyls, $C_4$–$C_{18}$ polyether hydrocarbons, $C_4$–$C_{18}$ alkyls having a chiral center, all alkyls optionally being unsaturated, and cholesterolic hydrocarbons. Tails having different lengths are demonstrated by (S)-N-octanoylvalinol, (S)-N-octoxycarbonylvaline; (S)-N-dodecoxycarbonylvaline; and (S)-N-pentadecafluorooctanoylvaline, and (S)-N-Tetradecoxycarbonylvaline. Halogen-substituted tails are demonstrated by fluorocarbon tails, particularly (S)-N-Pentadecafluorooctanoylvaline. Polyether hydrocarbon tails are also demonstrated herein, and include (S)-N-dodecylpolyoxyethylene(4)oxycarbonylvaline. Cholesterolic tails are also demonstrated herein and include (S)-N-cholesteroxycarbonylvalinol.

The invention also includes a kit for separating chiral compounds into their constituent enantiomers comprising, alone or in combination, a chiral surfactant of the present invention in combination with: an electrolyte effective for chiral capillary electrophoresis; a channel capable of containing the electrolyte; a power supply capable of generating a field strength of at least about 10 V/cm to about 1 kV/cm; at least one anode and cathode electrically connected to the opposite ends of the channel; and a detector for sensing the presence of the separated enantiomers.

The invention also includes a kit for separating chiral compounds into their constituent enantiomers, compartmentalized to receive in close confinement one or more containers, which comprises in combination a first container comprising any chiral surfactant of this invention. The kit may also comprise at least a second container comprising a different chiral surfactant of this invention, whereby said differing chiral surfactants are admixed to form a mixed chiral surfactant formulation. The kit may also comprise at least an additional container containing an achiral surfactant.

The invention is also directed to a method for separating a chiral compound into its constituent enantiomers, comprising the step of contacting said chiral compound with an effective amount of a micellar chiral surfactant under electrophoretic capillary chromatographic conditions, said chiral surfactant comprising:

a chiral selector, said chiral selector having at least one chiral center;

a hydrophilic head group bonded to said chiral selector, which in combination with said chiral selector potentiates the chiral selectivity of said chiral surfactant sufficiently to effect substantial separation of a chiral compound;

a linker bonded to said chiral selector which in combination with said chiral selector potentiates the chiral selectivity of said chiral surfactant sufficiently to effect substantial separation of a chiral compound; and a hydrophobic tail bonded to said linker, which in combination with said chiral selector potentiates the chiral selectivity of said chiral surfactant sufficiently to effect substantial separation of a chiral compound. This method also applies where chiral surfactant is present at or above its critical micellar concentration n substantially aqueous solution, and wherein the electrophoretic conditions include substantial electroosmotic flow.

The invention is also directed to a novel method for analyzing the dipeptide Aspartame, comprising the steps of injecting a sample of aspartame into a micellar electrokinetic capillary electrophoresis apparatus, said apparatus having an electrolyte containing a chiral surfactant of this invention, separating the enantiomers of aspartame, and then detecting the separated enantiomers. This invention provides a high-speed method for process testing in the food and beverage market.

It is an object of this invention to provide a broad chiral surfactant selectivity which confers the ability to do separations of a wise variety of compounds with a single or small number of chiral surfactants.

It is another object to provide increased chiral surfactant types having solubility over a wide pH and concentration range, which further allows flexibility and broader selectivity in developing chiral separations.

Is as yet another object to provide the ability to modulate enantioselectivity by altering the linking group, the hydrophilic head group, and the hydrophobic tail group.

It is still another object to provide better UV transmissibility, which allows better sensitivity and linearity of quantitation.

Other aspects, advantages and objectives of the present invention will become apparent from the following detailed description taken in conjunction with the accompanying drawings.

BRIEF DESCRIPTION OF THE DRAWINGS

FIG. 2(A) shows the key elements in block diagram format of the chiral surfactants described in this invention, which include the tail, linker, chiral selector and head.

FIG. 2(B) is a chemical structure of a typical chiral surfactant corresponding to the block diagram of FIG. 2(A).

FIG. 6 shows the effect that increasing the concentration of (S)-N-dodecoxycarbonylvaline from 25 mM to 100 mM has on the chiral separation of atenolol.

FIG. 7 shows how the concentration of (S)-N-dodecoxycarbonylvaline can be lowered from 25 mM to 5 mM in order to effect chiral separation of the hydrophobic analyte propranolol.

FIG. 14(A) shows chiral separation of ketamine with an alpha of 1.01 using 25 mM (S)-N-dodecoxycarbonylvaline (carbamate linker).

FIG. 14(B) shows chiral separation of ketamine with an alpha of 1.04 using 25 mM (S)-N-dodecylaminocarbonylvaline (urea linker).

FIG. 15 provides structures of proglumide and CBZ-tryptophan.

FIG. 16(A) shows chiral separation of proglumide obtained at pH 3.0 with 25 mM (S)-2-[(1-oxododecyl)amino]-3-methyl-1-sulfooxybutaine.

FIG. 16(B) shows chiral separation of CBZ-tryptophan obtained at pH 3.0 with 25 mM (S)-2-[(1-oxododecyl)amino]-3-methyl-1-sulfooxybutane.

FIG. 19(A) shows the chiral separation of benzoin obtained at an electroosmotic mobility of 1.4×10−4 cm2/Vs (pH 4.0) with 20 mM (S)-2-[(1-oxododecyl)amino]-3-methyl-1-sulfooxybutane.

FIG. 19(B) shows the chiral separation of benzoin obtained at an electroosmotic mobility of 3.19×10−4 cm2/Vs (pH 6.0) with 20 mM (S)-2-[(1-oxododecyl)amino]-3-methyl-1-sulfooxybutane

FIGS. 21(A)–(C) are chromatographs of the separation of ephedrine in urine.

FIG. 22(B) shows the separation of the same compound on N-dodecyl-(S)-leucinamide hydrochloride (FIG. 3b1, C12-amide-leucine-ammonium salt).

MODES FOR CARRYING OUT THE INVENTION

The invention is directed to chiral surfactants, methods of making and using them, apparatus and kits for performing chiral separations using the novel compounds of this invention. In addition to the ability to form micelles, the chiral surfactants of this invention also possess several other characteristics. First, they show enantioselectivity, or alpha, toward enantiomeric mixtures. Second, they show the ability to partition compounds of interest. Third, they show high efficiency, or plates, when used in an MEKC system. Fourth, they have desirable properties with regard to the detection mode. Finally, their contribution to the conductivity of the MEKC buffer should be minimized. The figures and examples described below further illustrate these characteristics.

Figure 1:
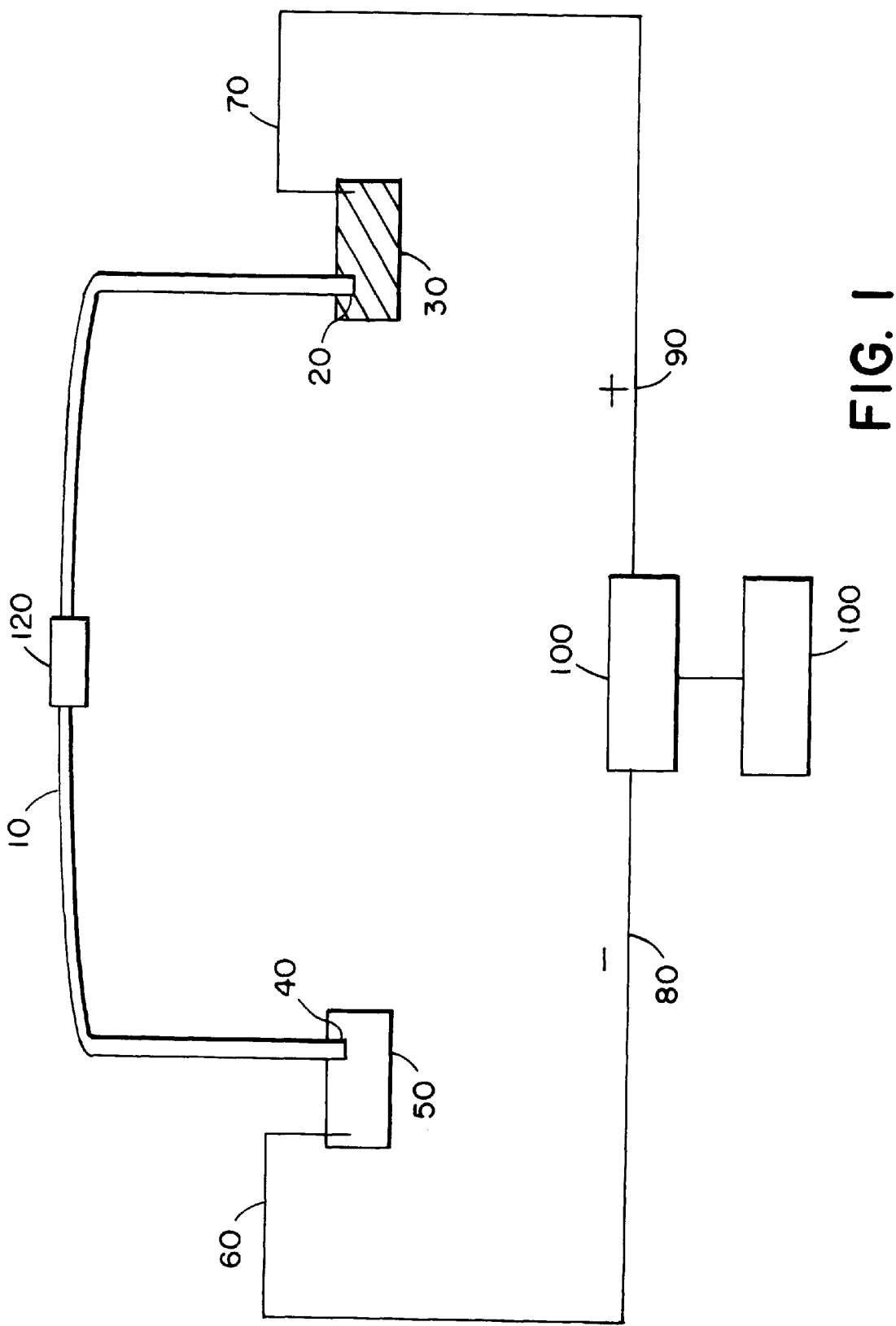
FIG. 1 is a block diagram of a typical capillary electrophoresis system.

FIG. 1 shows a block diagram of a CE system. The system includes a fused silica capillary 10 with an inside diameter having a range of about 5 $\mu$m to 500 $\mu$m, and an outside diameter having a range of about 100 $\mu$m to 100 $\mu$m and a length having a range of about 5 cm to 200 cm. The capillary includes an inlet end 20 immersed in an reservoir 30 containing electrolyte and an outlet end 40 immersed in an electrolyte 50. Both inlet and outlet electrolyte reservoirs as well as the capillary are filed with electrolyte which is composed of a supporting buffer that contains a chiral surfactant. The capillary is also filled with the electrolyte. Contacting the reservoirs are separate electrodes 60 and 70 that are connected to the output terminals 80 and 90 of a high voltage power supply 100. The electrical circuit is completed from the input electrode through the filled capillary to the outlet end of the capillary and to the high voltage electrode that is immersed in the outlet reservoir. The high voltage power supply output is set by a controller 110, and the separation monitored by a UV/V is detector 120.

The structural components of the chiral surfactants of the present invention are shown in FIG. 2. These surfactants can be divided into four structural units. Starting at the left, the first is the hydrophobic tail, which helps determine the ability of the surfactant to form micelles. The tail provides the hydrophobic portion of the micelle that allows the partitioning of the analyte molecule between the aqueous phase and the micelle s hydrophobic environment. The tail can vary in chain length from 4 to 20 carbons, although in the preferred embodiment it is from 6 to 18 carbons, and may be either linear or branched in structure. Changing the tail length also changes the critical micellar concentration (cmc). Different surfactant concentration allows one to modulate partitioning. The tail may also contain an ether or polyether portion in addition to its hydrophobic portion. Halogens may also be substituted for hydrogen on the carbon backbone. In particular, halogens such as chlorine, fluorine, bromine and iodine are preferred. Most preferred are chlorine and fluorine. In Example 21 it is demonstrated that the tail's length may influence enantioselectivity. It is shown that the placement of a chiral center within the tail affects the alpha values obtainable, as does the degree of branching.

The second portion of the chiral surfactant is the linkage between the hydrophobic tail portion of the molecule and the chiral center. Variation of this linkage results in significant changes in enantioselectivity, possibly because the linker is physically next to the chiral selector. Four types of linkers have been studied and are presented herein. They are amides, carbamates, sulphonamides, and ureas. The amide linkers are demonstrated in FIG. 2(B) by the R—CO—NH—R' subunit. A carbamate linker is demonstrated in FIG. 3(A) by the R—OCO—NH—R' subunit. A sulphonamide linker is shown in FIG. 3(H) by the R—SO$_2$—NH—R' subunit. The urea linker is shown in FIG. 3(G) by the R—NH—CO—NH—R' subunit. One of the surprizing results of this invention is the fact that the linkers have such a strong influence on the separation. As will be shown by the Examples the substitution of one linker type for another can transform a marginal separation into one that works. Although not wishing to be bound by any theory of the invention, it is believed that selection of the correct linker potentiates, or increases the chiral selectivity of the chiral selector. Other linkers not disclosed herein may also come within the scope of this invention if they potentiate the chiral selector.

The third portion of the molecule is the chiral center. The chiral center can be derived from any chiral compound. A chiral molecule is one that rotates the plane of polarized light. A chiral molecule is defined as not being superimposable on its mirror image. (March, J., *Advanced Organic Chemistry, Third ed.*, John Wiley & Sons, New York, 1985, p. 82) This invention demonstrates chiral compounds including amino acids, amino alcohols, and tartaric acid derivatives. Amino acids and their derivatives are particularly preferred chiral selectors because both enantiomers are available. Not only are the 20 essential amino acids included herein, but all other amino acids that contain at least one chiral center come within the scope of this invention. Examples are provided for the synthesis of at least 8 different amino acid-containing selectors, including phenylglycine, serine, valine, proline, aspartic acid, leucine, isoleucine, and tertiary-leucine. Amino alcohols are also demonstrated as chiral selectors. Representative of amino alcohols are valinol-, ephedrine-, and aminopropanediol-based chiral surfactants. Tartaric acid derivative contain two chiral centers in the center of the molecule, and two carboxyl groups at each end (See FIGS. 3A5–A9). Linkage of the tartaric acid to the surfactant is through formation of a carboxamide group. Tartaric acid derivatives demonstrate the incorporation of two functionalities (head group and chiral selector) into one precursor molecule, reducing the number of synthetic steps required. Other bifunctional molecules can be made that also incorporate two or more of the four functions of the chiral surfactants of this invention.

The final portion of the molecule is the head group. This portion of the structure strongly influences the size, aggregation number, and solubility of the micelle. In a micelle, the head group is located on the periphery, oriented outwards towards the aqueous phase. The head group should contain an ionizable moiety so that solubility with the aqueous phase is enhanced. Moietys that are not ionized at neutral pH may become charged when the pH is raised or lowered, thus enhancing solubility. The invention discloses three types of head groups, carboxylates, sulfates, and alcohols. Carboxylates (R—COOH) are the most numerous, and an example is demonstrated in FIG. 3(a). Sulfates (SO$_3$O$^-$M$^+$) are also useful as head groups, as demonstrated in FIG. 3(p). Alcohols, —OH, are also used to enhance solubility, as shown in FIG. 3(i). Alcoholic head groups are examples of compounds that are ionizable. Alcohols may become protonated at lower pH's, and become deprotonated at higher pH's, resulting in a net charge and enhanced solubility in aqueous media. Other ionizable groups come within the scope of this invention, such as amines (HN), particularly quaternary amines (NR$_4^+$) and ammonium salts NH$_3^+$, sulfhydrals (SH), sulfonates (SO$_3^-$), amides (CONH), amidines, and guanidines.

Table 1 summarizes the different types of the four strucural units which have been prepared.

TABLE 1

Summary of Different Head Groups, Chiral Selectors, Linkers and Tails Which Have Been Investigated

| Head Groups | Chiral Selectors | Linkers | Hydrophobic Tails |
| --- | --- | --- | --- |
| alcohol | tartrate | urea | polyether-hydrocarbons |
| sulfate | amino acids | carbamate | cholesterolic |
| carboxylate | amino alcohols | sulfonamide | fluorohydrocarbon substituted |
| ammonium salts | | amide | C8—C18 linear hydrocarbon, chiral branched tail |

FIG. 3 summarizes the variety of chiral surfactants that have been synthesized and tested for enantioselectivity using capillary electrophoresis. The surfactants consist of a group of carbamate linked surfactants, a group of urea linked surfactants, a sulfonamide linked surfactant, a polyetherhydrocarbon tail surfactant, a group of fluorohydrocarbon tail surfactants, a group of cholesteric tail surfactants, a group of chiral surfactants of varied tail length, a group of alcohol head group surfactants, a group of sulfate head group surfactants, a group of carboxylate head group surfactants, a group of amide linked surfactants, a group of tartrate-derived chiral selector-containing surfactants, a group of amino acid-derived chiral selector-containing surfactants, and a group of amino alcohol-derived chiral selector-containing surfactants. In some cases both enantiomers of a chiral surfactant have been used to show the reversal of enantiomer migration order. To date, a total of 68 surfactants have been synthesized and examined.

EXAMPLES

Unless otherwise noted chemicals were obtained from Aldrich Chemical or Sigma.

Example 1

Figure 3A:
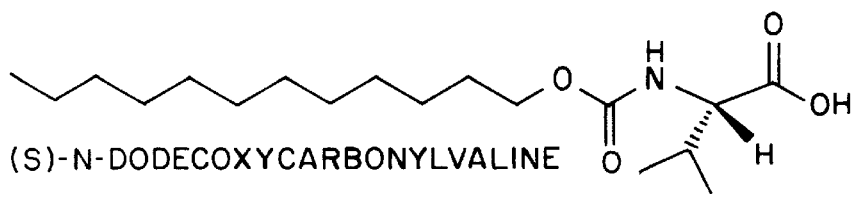
FIGS. 3(A)–3(BP) lists the structures of the surfactants which have been prepared and evaluated for enantioselectivity for this invention.
Figure 3B:
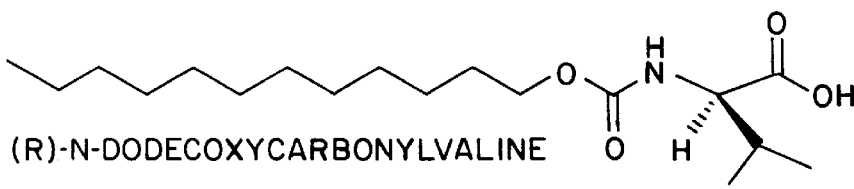
Figure 3C:
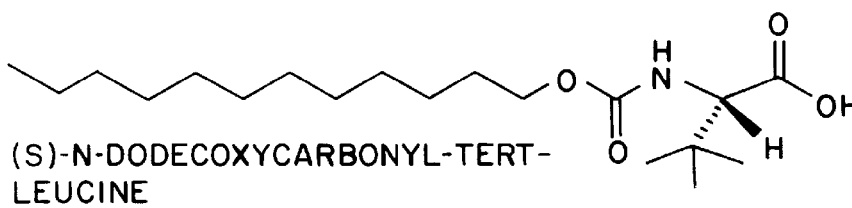
Figure 3D:
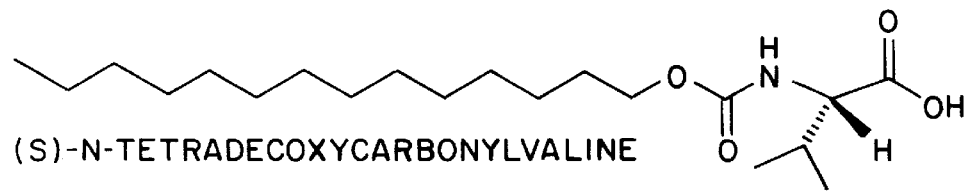
Figure 3E:
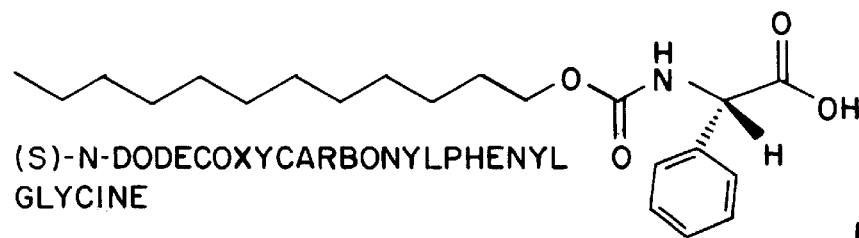
Figure 3F:
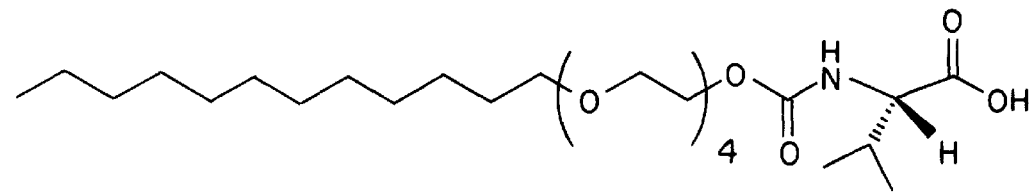
Figure 3G:
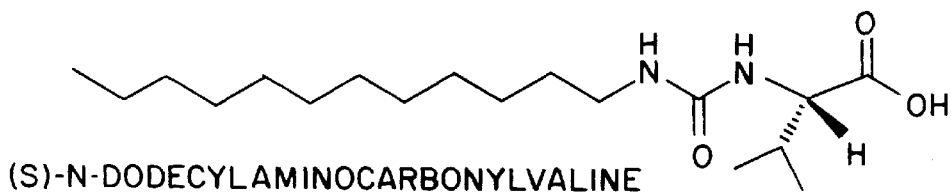
Figure 3H:
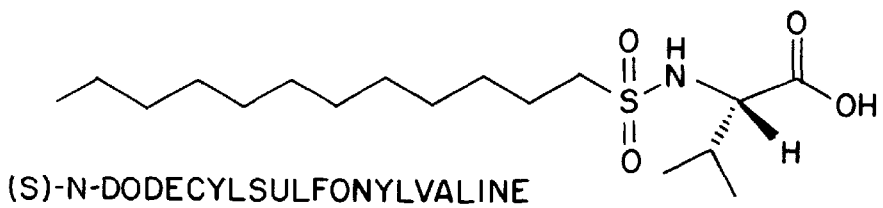

Synthesis Of (S)-N-dodecoxycarbonylvaline (FIG. 3a)

To a three neck round bottom flask equipped with a thermometer, an addition funnel, and a mechanical stirring apparatus was added (S)-valine [Aldrich Chemical Company] (34.17 grams, 291 mmol), water (180 milliliters), and acetone (120 milliliters). The slurry was cooled to 0–5°

C. Sodium hydroxide pellets (21.25 grams, 531 mmol) were added slowly to the slurry to maintain the temperature between 5–10° C. Dodecyl chloroformate (48.21 grams, 207 mmol), prepared by the method of Richter and Tucker (Richter, R. and Tucker, B., Journal of Organic Chemistry, 1983, (48) 2625–2627), was added dropwise over 1 hour to the reaction mixture so that the temperature was maintained between 5—10° C. during the addition. The reaction mixture was stirred at 0–5° C. for 1 hour, warmed to ambient temperature, and stirred for 16 hours. The reaction mixture was a clear, slightly yellow solution. The solution was concentrated on a rotary evaporator, and the resulting aqueous phase was diluted with water (700 mL) and extracted with ethyl acetate (6×250 mL). The aqueous phase was cooled to 5–10° C. and concentrated hydrochloric acid was added to reduce the pH to 1. The aqueous phase and oily precipitate was extracted with ethyl acetate (4×250 mL). The organic phase was evaporated to yield a white solid (47.6 g, 73%) which was the desired product by 1H-NMR and pure by HPLC (C18 reverse phase, methanol/water/acetic acid mobile phase).

Example 2

Synthesis of Compounds of FIGS. 3b–3f, FIGS. 3A10–3A24

(R)-N-dodecoxycarbonylvaline (FIG. 3b), (S)-N-dodecoxycarbonyl-tert-leucine (FIG. 3c), (S)-N-tetradecoxycarbonylvaline (FIG. 3d), (S)-N-dodecoxycarbonylphenylglycine (FIG. 3e), and (S)-N-dodecylpolyoxyethylene(4)-oxycarbonylvaline (FIG. 3f) were also synthesized by this procedure. The starting material for the synthesis of (S)-N-dodecylpolyoxyethylene(4)-oxycarbonylvaline was Brij 30 [Aldrich Chemical Company], a mixture of polyoxyethylene(4 to 12)lauryl and myristyl ethers. The product chiral surfactant was thus also a mixture.

The compounds of FIGS. 3aj–3ax were also prepared according to the synthetic procedure outlined above, with the exceptions that the chloroformate used was based on the tail structure of the corresponding surfactant being synthesized.

Example 3

Figure 25:
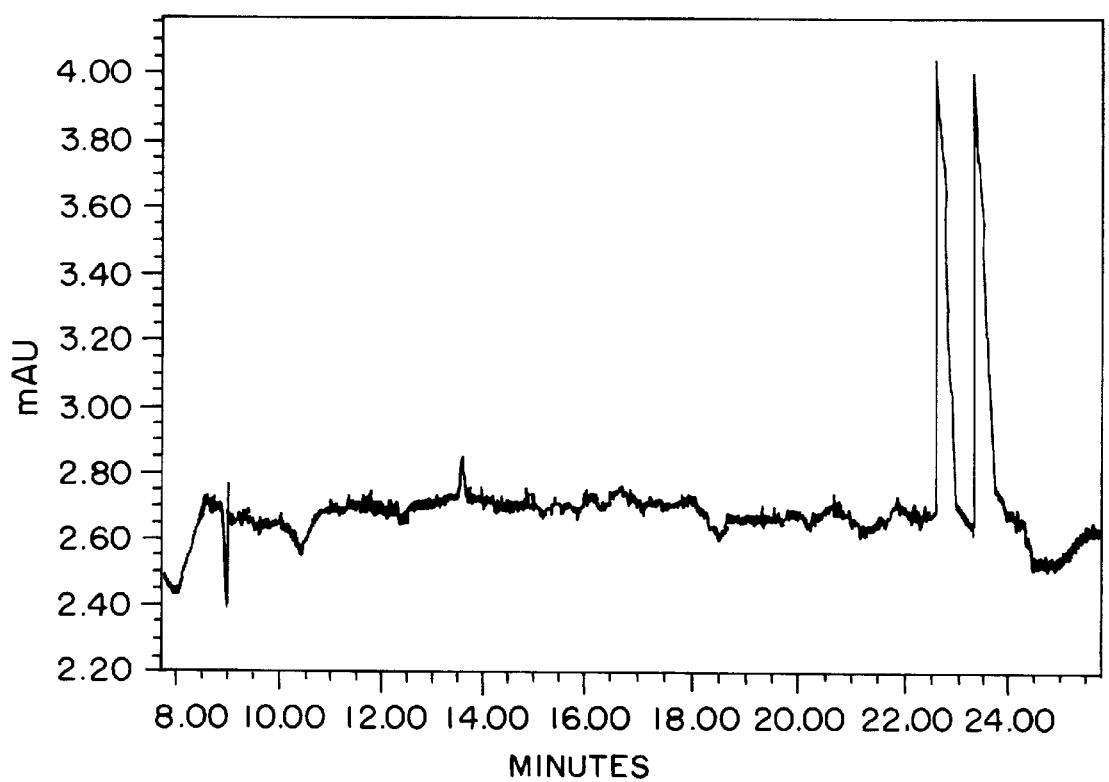
FIG. 25 is a chromatogram showing the separation of the anionic compound carboxybenzoyl-DL-alanine using 25 mM N-dodecyl-(S)-prolinamide hydrochloride (FIG. 3bn) at pH 3.0.

Synthesis Of the Compounds of FIGS. 3g, 3A25

This urea linker compound was synthesized using the same procedure as Example 1, except that dodecylisocyante [Kodak] was used in place of dodecylchloroformate. The product was obtained in 73% yield and was pure by $^1$H-NMR and HPLC.

The compound of FIG. 3A25 was also prepared according to the synthetic procedure outlined above, with the exception that decylisocyante was used in place of dodecylisocyante.

Example 4

Synthesis Of Compounds of FIGS. 3h

This sufonamide was synthesized using the same procedure as in Example 1 except that dodecylsulfonyl chloride [Lancaster labs] was used in place of dodecylchloroformate. A precipitate consisting of the desired product and dodecanesulfonic acid formed during the reaction. The desired product was isolated by preparative HPLC (C18 reverse phase, methanol/water/acetic acid, 50% yield) and was pure by 1H-NMR and HPLC.

Example 5

Synthesis Of Compunds of FIGS. 3s–3y

This amide-linker, FIG. 3w, was synthesized using the same procedure as in Example 1 except that dodecanoyl chloride was used in place of dodecylchloroformate. The product was isolated via methylene chloride extraction in 97% yield. The product was used for subsequent CE experiments as is (containing 3% lauric acid); or pure product was isolated by preparative HPLC (C18 reverse phase, methanol/water/acetic acid)

(S)-N-dodecanoylphenylglycine (FIG. 3s), (S)-N-dodecanoylserine (FIG. 3t), (S)-N-dodecanoylproline (FIG. 3u), (S)-N-dodecanoylaspartic acid (FIG. 3v), (S)-N-octanoylvaline (FIG. 3x), and (S)-N-hexadecanoylvaline (FIG. 3y) were synthesized similarly.

Example 6

Synthesis of the Compounds of FIG. 3A2–3A5 and FIGS. 3A26–3B3

To a three neck round bottom flask equipped with a thermometer, an addition funnel, and a mechanical stirring apparatus was added (S)-valinol (25.9 grams, 251 mmol) and dichloromethane (180 mL). The solution was cooled to 0–5° C. under nitrogen. Dodecanoyl chloride (27.3 grams, 125 mmol) in dichloromethane (120 mL) was added dropwise over 1.5 hour to the reaction mixture while maintaining the temperature between 5–10° C. The reaction mixture was stirred at 0–5° C. for 1 hour, warmed to ambient temperature, and stirred for 17 hours. A white precipitate was observed. To remove ammonium salts, the reaction mixture was extracted with water (1×250 mL), aqueous 0.1 molar hydrochloric acid (1×250 mL), and water (1×250 mL). The organic solution was concentrated on the rotary evaporator, and the resulting white solid was dried in vacuo overnight to afford the desired product (35.0 g, 98% yield). The product, (S)-N-dodecanoylvalinol (FIG. 3ab), was pure by HPLC and 1H NMR.

(S)-N-octanoylvalinol (FIG. 3A3), (1S,2R)-N-docecanoylephedrine (FIG. 3A4), and (1S,2S)-N-amino-1-phenyl-1,3-propanediol dodecanamide (FIG. 3A5) were synthesized similarly.

The compounds of FIGS. 3A26–3B3 were also prepared according to the synthetic procedure outlined above.

Example 7

Figure 3I:
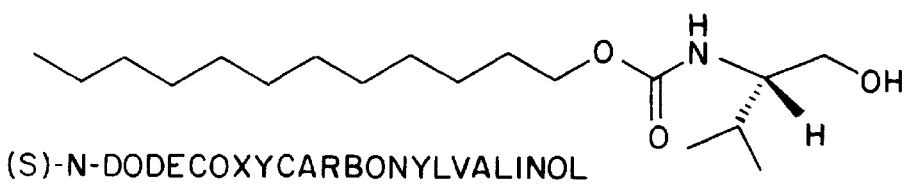
Figure 3J:
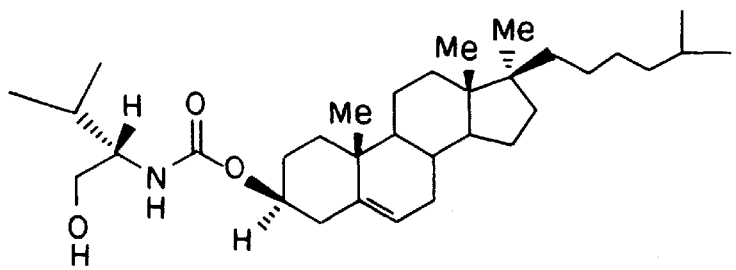
Figure 3K:
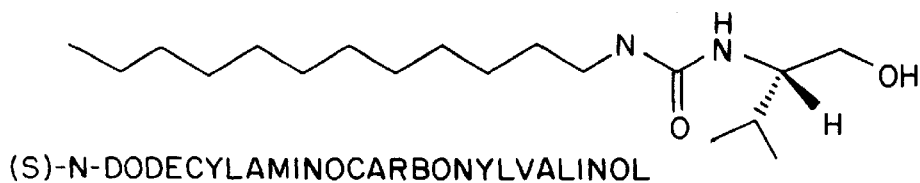
Figure 3L:
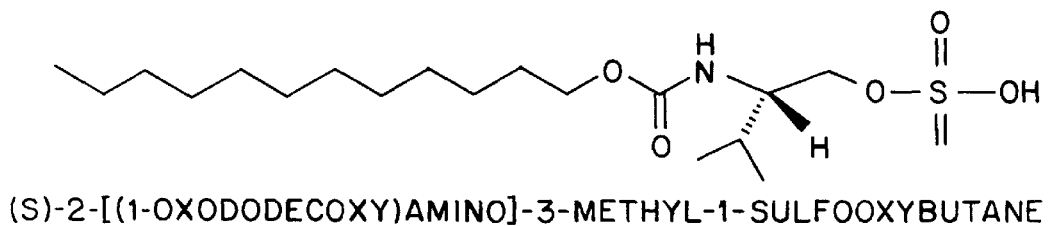

Synthesis of the Compounds of FIGS. 3i–k

This carbamate-linker, (S)-N-dodecoxycarbonylvalinol, was synthesized suing the same procedure as the amide, (S)-N-dodecanoylvalinol, (Ex. 6) except that dodecylchloroformate was used in place of the acid chloride.

(S)-N-Cholesteroxycarbonylvalinol (FIG. 3j) was synthesized similarly from valinol and cholesteryl chloroformate.

(S)-N-dodecylaminocarbonylvalinol (FIG. 3k) was synthesized similarly from valinol and dodecylisocyante.

Example 8

Synthesis Of the Compounds of FIGS. 3l–o, FIGS. 3B4–3B7

To a three neck round bottom flask equipped with a thermometer, an addition funnel, and a mechanical stirring apparatus was added (S)-N-dodecanoylvalinol (5.00 grams, 17.5 mmol) and dichloromethane (120 mL). The solution was cooled to 0–5° C. under nitrogen. Chlorosulfonic acid (2.04 grams, 17.5 mmol) in dichloromethane (30 mL) was added dropwise over 0.5 hour to the reaction mixture while maintaining the temperature between 5–10° C. The reaction mixture was stirred at 0–5° C. for 2 hours. The solution was concentrated on the rotary evaporator, and the remaining white solid was dried in vacuo. To the solid was added methanol (100 mL), R. O. water (10 mL), and sodium hydroxide pellets (0.700 grams, 175. mmol). When dissolution of the pellets was complete, the solution was concentrated on the rotary evaporator, and the remaining white solid was dried in vacuo for 17 hours at 25° C. The identity of the product, (S)-2-[(1-oxododecyl)amino]-3-methyl-1-sulfooxy-butane (FIG. 3m), (6.64 g, 98% yield) was confirmed by 1H-NMR.

(S)-2-[(1-oxododecoxy)amino]-3-methyl-1-sulfooxybutane (FIG. 3l), (S)-2-[(1-oxododecylamino) amino]-3-methyl-1-sulfooxybutane (FIG. 3n), and (S)-[Oxocholesteroxylamino]-3-methyl-1-sulfoxybutane (FIG. 3o) were synthesized by similar procedures.

Figure 4:
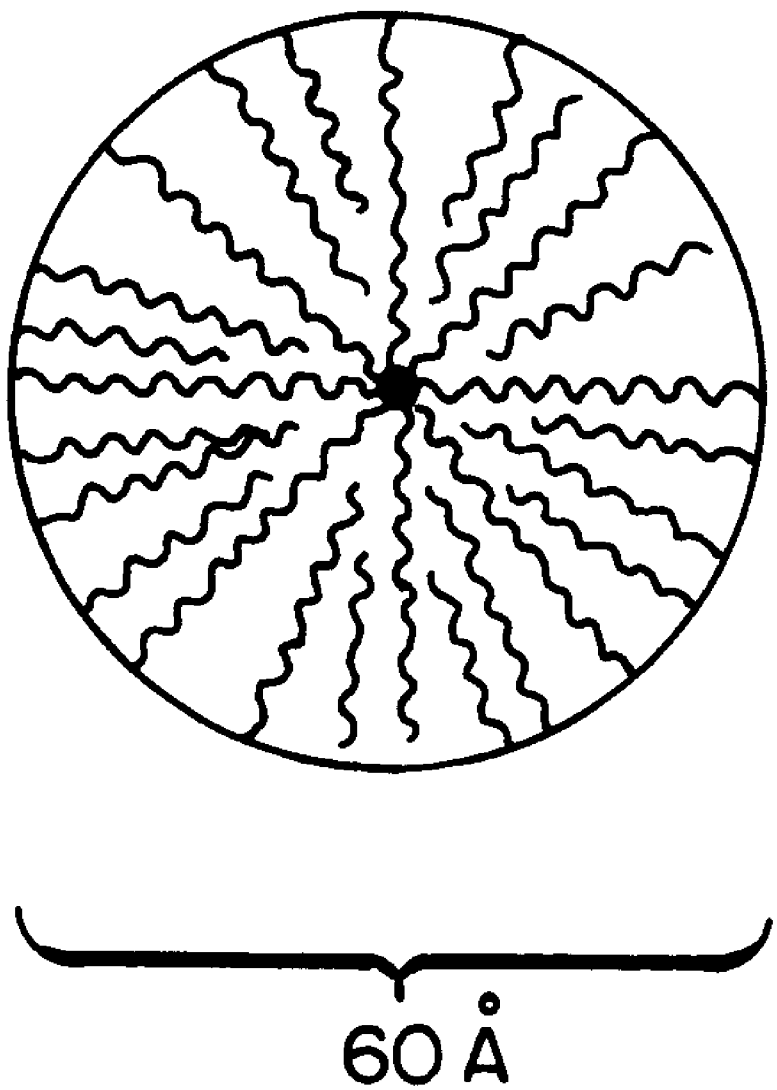
FIG. 4 shows the idealized structure of a micelle, with sodium dodecyl sulfate used as an example.

The compounds of FIGS. 3B4–3B7 were also prepared according to the synthetic procedure outlined above.

Example 9

Synthesis Of Compounds of FIGS. 3z ((S)-N-pentadecafluorooctanoylvaline) via (S)-N-pentadecafluorooctanoylvaline methyl ester.

To a three neck round bottom flask equipped with a thermometer, an addition funnel, and a mechanical stirring apparatus was added (S)-valine methyl ester hydrochloride (5.81 g, 34.7 mmol), dichloromethane (350 mL), and triethylamine (8.53 g, 84.3 mmol). The solution was cooled to 0–5° C. under nitrogen. Pentadecafluorooctanoyl chloride (15.0 grams, 34.7 mmol) in dichloromethane (50 mL) was added dropwise over 0.5 hour while maintaining the temperature between 5–10° C. The reaction mixture was stirred at 0–5° C. for 1 hour, warmed to ambient temperature, and stirred for 2 hours. A white precipitate was observed. The reaction mixture was extracted with water (1×250 mL), aqueous 0.1 molar hydrochloric acid (1×250 mL), and water (1×250 mL). The solution was concentrated on a rotary evaporator, and the resulting white solid was dried in vacuo overnight to afford the desired product (18.2 g, 99% yield). The product was shown to be pure by HPLC and 13C-NMR.

To a three neck round bottom flask equipped with a thermometer, a stopper, and a mechanical stirring apparatus was added (S)-N-pentadecafluorooctanoylvaline methyl ester (2.00 g, 3.8 mmol), tetrahydrofuran (100 mL), and water (22 mL). The solution was cooled to 0–5° C. Potassium hydroxide pellets (0.70 grams, 12.5 mmol) were slowly added. After 12 hours, the reaction vessel was stoppered and placed in the refrigerator for another 12 hours. The solution was concentrated on a rotary evaporator, and the remaining solution was diluted with water (150 mL) and cooled to 5–10° C. The solution was acidified with concentrated hydrochloric acid to pH 1. The temperature was maintained between 5–15° C. during the addition. A white precipitate was formed. The aqueous phase and precipitate were extracted with ethyl acetate (3×150 mL). The organic solution was concentrated on a rotary evaporator to afford a white solid which was dried in vacuo overnight to afford the desired product (2.02 g, 97% yield). 13C NMR spectroscopic and HPLC analysis showed the product to be pure.

Example 10

Figure 5:
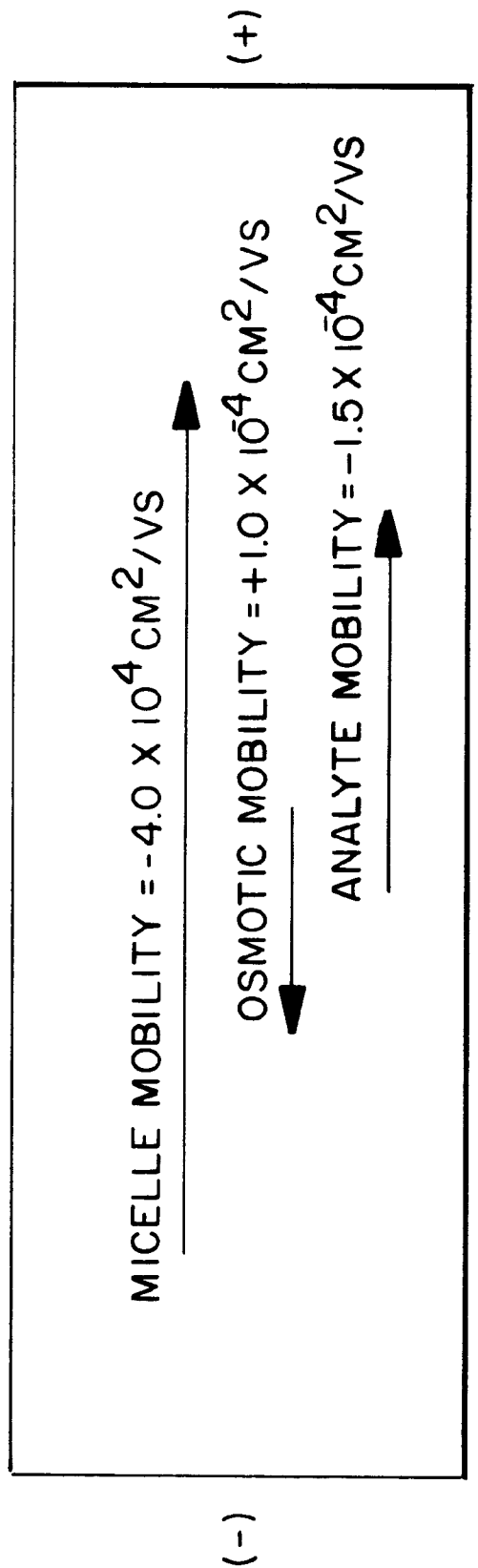
FIG. 5 is a vector diagram of micelle, electroosmotic and analyte mobilities in a typical low electroosmotic flow chiral MEKC separation.
Figure 9:
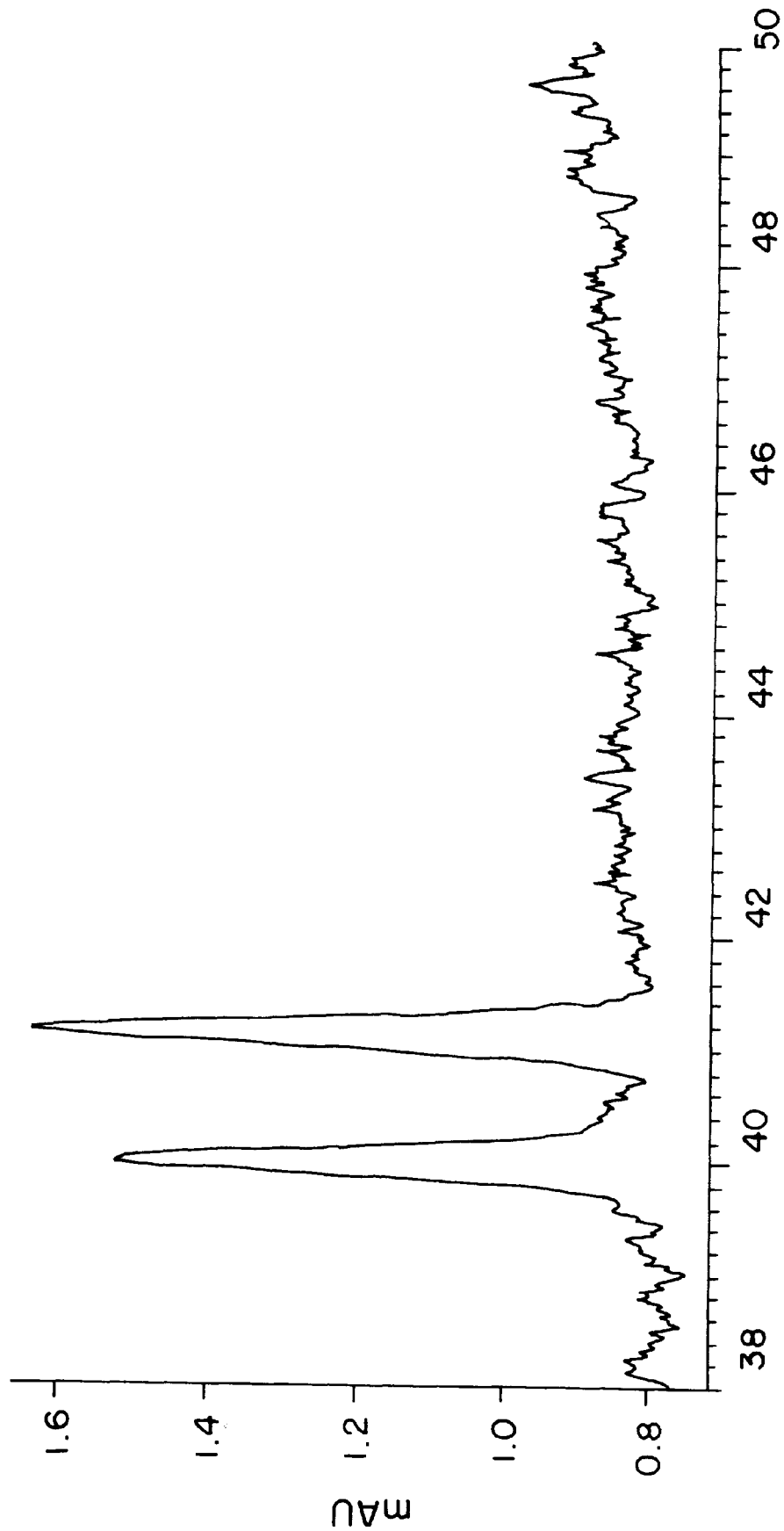
FIG. 9 is a chiral separation of bupivacaine obtained with 50 mM (S)-N-pentadecafluorooctanoylvaline.

Synthesis Of Compounds of FIG. 3A7 ((R,R)-N-dodecyltartaric acid monoamide via (R,R)-N-dodecyl-O,O-diacetyltartaric acid monoamide, FIG. 3A9, (R,R)-N-decyltartaric acid monoamide, and FIG. 3B5, (R,R)-N-Octyltartaric acid monoamide To a three neck round bottom flask equipped with a thermometer, an addition funnel, and a mechanical stirring apparatus was added 1-dodecylamine (17.14 g, 92.5 mmol), tetrahydrofuran (350 mL), and triethylamine (9.36 grams, 92.5 mmol). The solution was cooled to 0–5° C. under nitrogen. (R,R)-O,O-diacetyltartaric anhydride (20.0 g, 92.5 mmol) in tetrahydrofuran (150 mL) was added dropwise over 1 hour to the reaction mixture while maintaining the temperature between 5–10° C. The reaction mixture was stirred at 0–5° C. for 1 hour, warmed to ambient temperature, and stirred for 4 hours. The solution was concentrated on a rotary evaporator, and the resulting brown, viscous oil was dried in vacuo overnight to afford crude product (46.1 grams) in 99% yield.

To a three neck round bottom flask equipped with a thermometer, a stopper, and a mechanical stirring apparatus was added (R,R)-N-dodecyl-O,O-diacetyltartaric acid monoamide (triethylamine form; 6.18 g, 12.3 mmol), methanol (150 mL), and water (15 mL). Sodium hydroxide (1.62 grams, 41.0 mmol) was added to the reaction mixture. After 0.5 hours, a white precipitate formed. The reaction mixture was heated to 55° C., and stirred for 18 hours. The solid was filtered off and dried in vacuo to afford product (3.96 g, 95% yield) which was shown to be pure by 1H NMR.

(R,R)-N-decyltartaric acid monoamide (FIG. 3A9) (sodium form) and FIG. 3B6, (R,R)-N-Octyltartaric acid monoamide, were synthesized via a similar two step procedure.

Example 11

Figure 8:
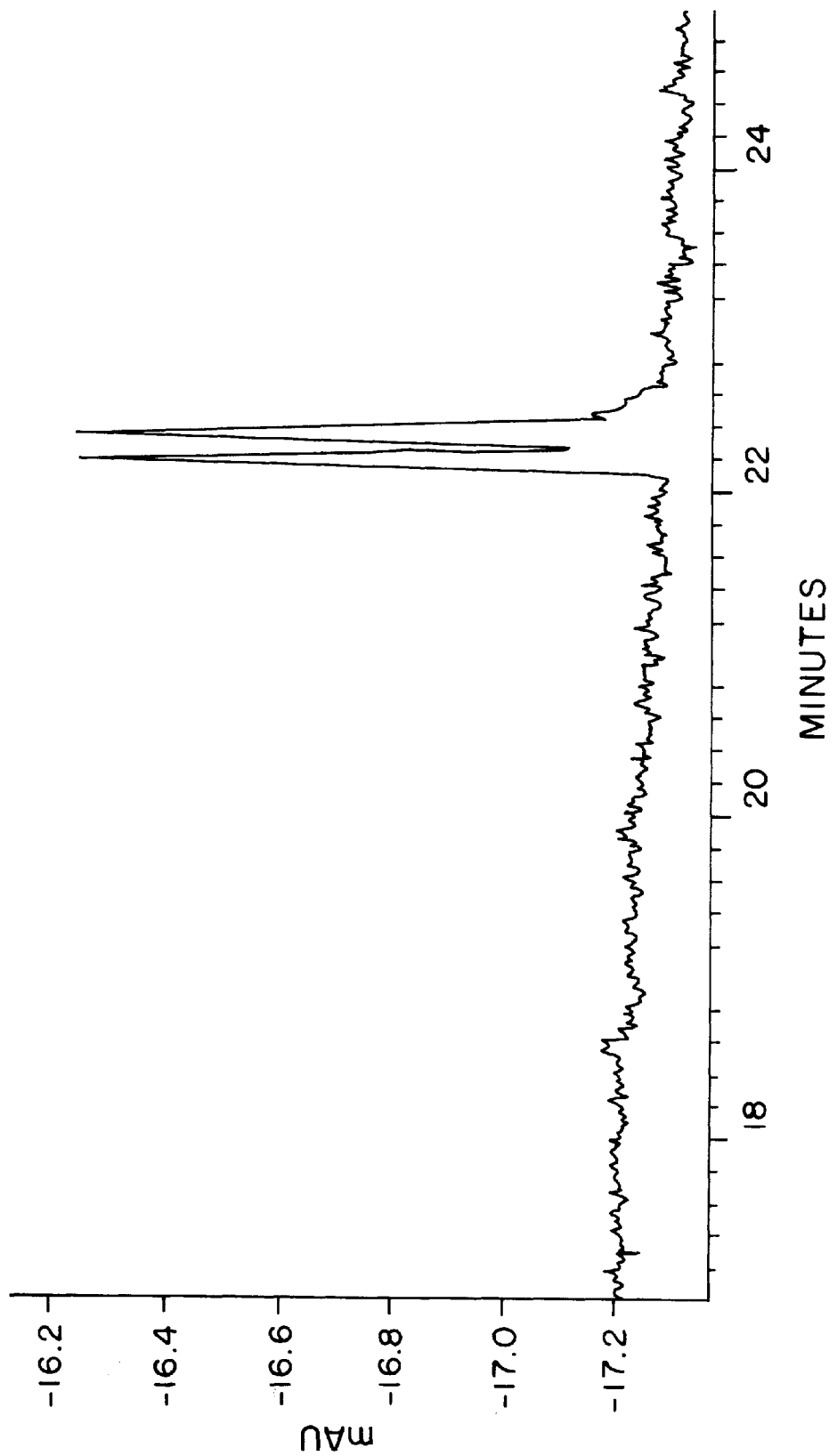
FIG. 8 is a chiral separation of the hydrophobic analyte oxprenolol obtained with 25 mM (S)-N-dodecylpolyoxyethylene(4)oxycarbonylvaline.

Synthesis of the Compounds of FIGS. 3B8–3B14

To a 500 milliliter three neck round bottom flask equipped with a thermometer, an addition funnel, and a mechanical stir apparatus was added N-t-BOC-(S)-proline (Sigma Chemical Company, 13.69 g, 63.6 mmol), triethylamine (6.44 g, 63.6 mmol), and dichloromethane (250 mL). The solution was cooled to 0–5° C. under nitrogen. Isobutyl chloroformate (Aldrich Chemical Company, 8.69 g, 63.6 mmol) in dichloromethane (50 mL) was slowly added dropwise over 0.5 hour to the reaction mixture while maintaining the temperature between 0–5° C. After the addition was complete, the reaction mixture was stirred at 0–5° C. for 15 min. 1-Dodecylamine (11.79 g, 63.6 mmol) in dichloromethane (50 mL) was then slowly added dropwise over 0.5 hour to the reaction mixture while maintaining the temperature between 0–5° C. The reaction mixture was stirred at 0–5° C. for 2 hours, warmed up to ambient temperature, and then stirred for 16 hours. The reaction mixture was extracted with aqueous hydrochloric acid (0.1 N; 2×100 mL), aqueous sodium hydroxide (0.1 N; 2×100 mL), and R.O. water (2×100 mL). Solvent was evaporated off on the rotary evaporator, and the remaining white solid was dried in vacuo overnight to afford crude product (24.02 g) in 99% yield. $^1$H NMR spectroscopic and HPLC analysis (C18 reverse phase, methanol/water/acetic acid mobile phase) showed that the desired product was obtained and was pure.

N-Dodecyl-(S)-prolinamide hydrochloride was obtained by reacting the crude product (24.0 g, 62.7 mmol) described above with concentrated aqueous hydrochloric acid (12 N, 480 mmol) in methanol (160 mL) at 25° C. for 16 hours. Solvent was evaporated off on the rotary evaporator, and the remaining white solid was dried in vacuo overnight to afford crude product (19.68 g) in 98% yield. $^1$H NMR spectroscopic and HPLC analysis (C18 reverse phase, methanol/water/acetic acid mobile phase) showed that the desired product was obtained and was pure.

Figure 12A:
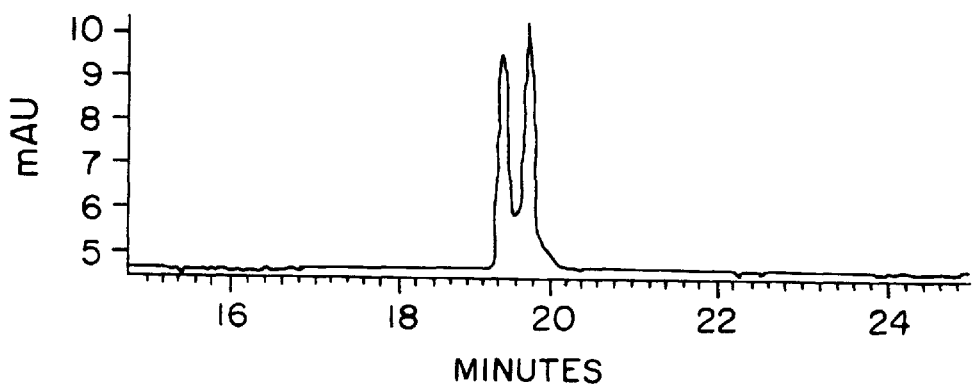
FIG. 12(A) shows chiral separation of PTH-tryptophan obtained with 25 mM (S)-N-dodecanoylvalinol/25 mM sodium dodecyl sulfate.
Figure 12B:
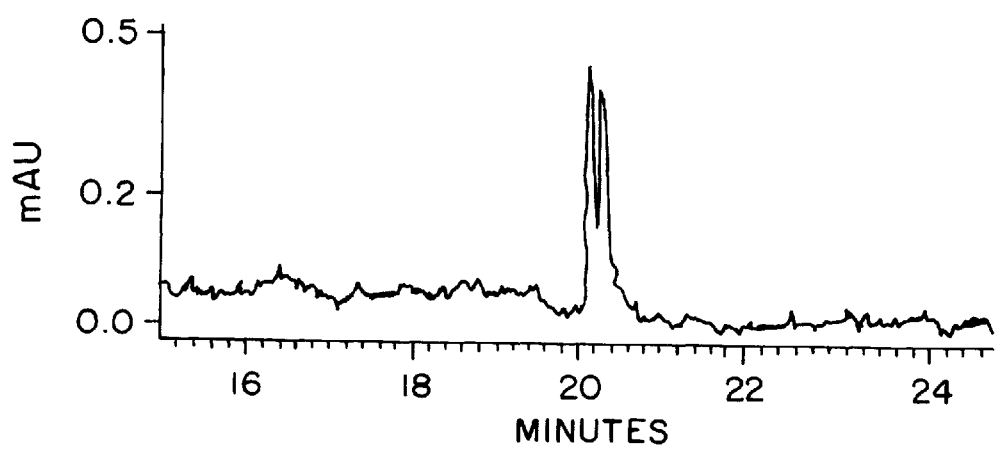
FIG. 12(B) shows chiral separation of terbutaline obtained with 25 mM (R,R)-N-dodecyltartaric acid monoamide, sodium salt/25 mM sodium dodecyl sulfate.
Figure 12C:
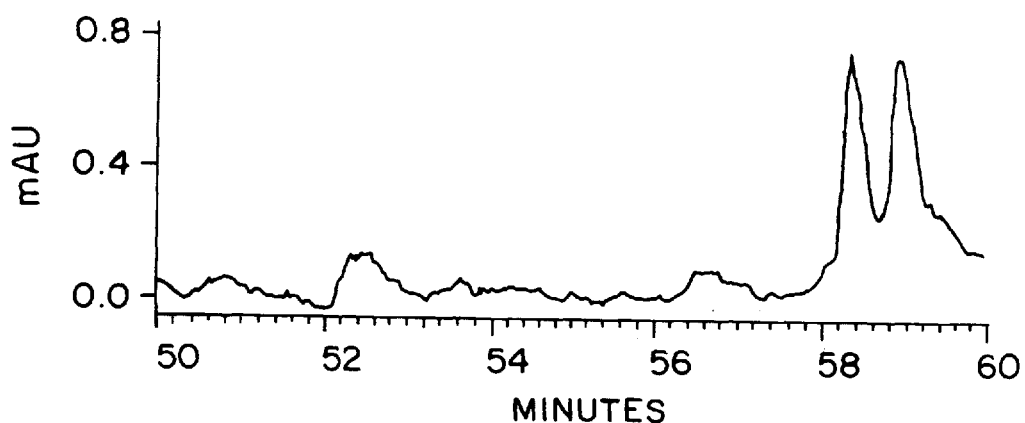
FIG. 12(C) shows chiral separation of bupivacaine obtained with 15 mM (1S, 2S)-N-amino-1-phenyl-1,3-propanediol dodecanamide/15 mM sodium dodecyl sulfate.
Figure 13A:
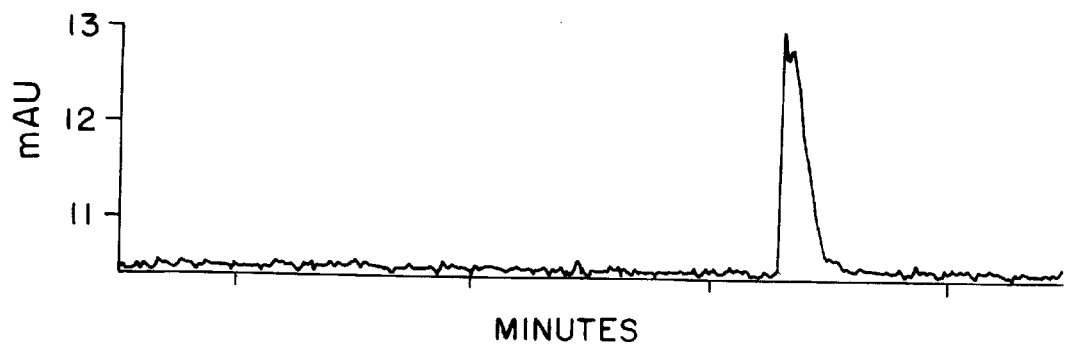
FIG. 13(A) shows chiral separation of metoprolol obtained with 25 mM (S)-N-dodecylsulfonylvaline (sulfonamide linker).
Figure 13B:
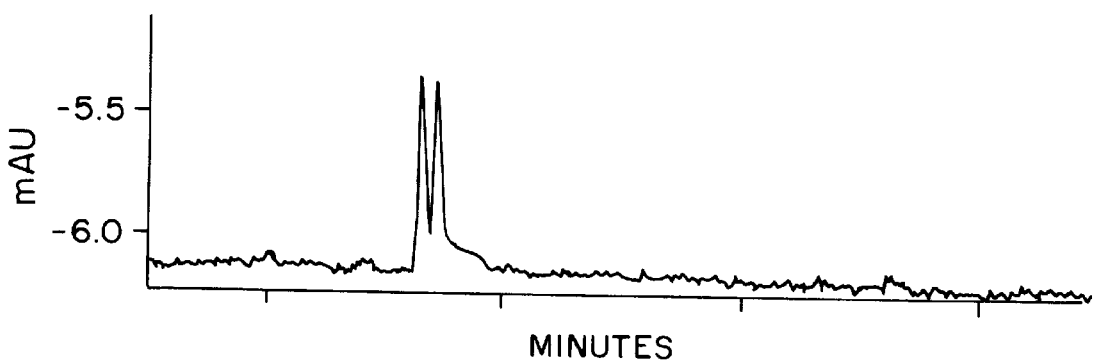
FIG. 13(B) shows chiral separation of metoprolol obtained with 25 mM (S)-N-dodecylaminocarbonylvaline (urea linker).
Figure 13C:
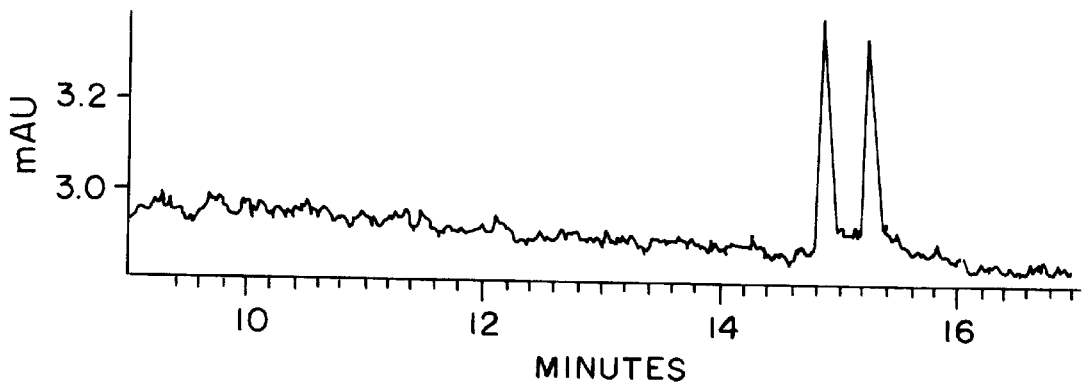
FIG. 13(C) shows chiral separation of metoprolol obtained with 25 mM (S)-N-dodecoxycarbonylvaline (carbamate linker).

This same procedure was used for the synthesis of N-octyl-(S)-valinamide hydrochloride (FIG. 3B9), N-decyl-(S)-valinamide hydrochloride (FIG. 3B8), N-tetradecyl-(S)-valinamide hydrochloride (FIG. 3bj), N-dodecyl-(S)-alaninamide hydrochloride (FIG. 3B11), N-dodecyl-(S)-leucinamide hydrochloride (FIG. 3B12), and N-dodecyl-(S)-isoleucinamide hydrochloride (FIG. 3B13).

Examples 12–17

Separation of Enantiomers

When a surfactant is added to an aqueous environment above its critical micelle concentration (cmc), individual surfactant molecules aggregate to form a structure called a micelle. A model of this structure is seen in FIG. 4 (the surfactant sodium dodecyl sulfate is shown as an example). The long hydrophobic tails of the surfactant become buried together within the structure, while the polar head group is hydrated with the water of the electrolyte. Once the sample is injected into the capillary, it has the opportunity to interact with the chiral micelles formed in the electrolyte. If the compound or a portion of it is hydrophobic, it will partition within the hydrophobic environment of the micelle.

The micelle has a characteristic charge/mass ratio which confers electrophoretic mobility to the micelle. Mobilities for the surfactants of this invention vary from about 1 to 5×10-4 cm2/V-sec. As the result of its electrophoretic mobility the micelle will migrate through the capillary with a characteristic migration time, $t_{mc}$, which depends on the capillary length and field strength. When an analyte is partitioned within the micelle, it will also display the apparent mobility of the micelle. If a molecule partitions totally within the aqueous phase, then it will have its own characteristic electrophoretic mobility defined by its charge/mass ratio. In FIG. 5, a vector diagram of micelle (-4×10-4 cm2/Vs) and electroosmotic (+1×10-4 cm2/Vs) mobilities is shown, as well as the apparent mobility of a neutral analyte (-1.5×10-4 cm2/Vs) which spends 50% of the time n the micelle and 50% of the time in bulk solution. Once partitioned within the micelle, the sample analyte has the opportunity to interact with the chiral center. If the sample molecules partition within the micelle only a portion of the time and the sample enantiomers differentially interact with the chiral center, the two enantiomers will have slightly different apparent mobilities, and can then be separated. Optimum levels of partitioning, or k, that result in maximum resolution are determined by the efficiency and selectivity of the separation system as shown in equation 2.

Experimental Apparatus and Conditions for Examples 12–17

Capillary electrophoretic separations were performed with a Waters Quanta® 4000 CE unit. Separations were performed in a 50 μm i.d.×60 cm uncoated or polyethylene glycol coated (J&W Scientific) fused silica capillary, 52.5 cm injection to detection. Applied voltage was 12 kV, generating currents ranging from 20 –60 μAmps. Injection was achieved by raising the inlet end of the capillary immersed in the sample solution to a height of 10 cm above the outlet end for 2–5 seconds. On-column UV detection was performed at 214 nm. Buffers were prepared from phosphate or phosphate/borate stock, and adjusted to the desired pH after solubilization of the surfactant. Data collection was achieved with Water ExpertEase™ or Millenium™ software (Waters Corporation, Milford, Mass.).

Example 12

Separation of Atenolol and Effect of Surfactant Concentration on Partitioning

The ability to modulate partitioning is an important element of the present invention. This was demonstrated in the separation of atenolol using a C12-carbamate-linked valine surfactant (FIG. 3a) seen in FIG. 6. At a surfactant concentration of 25 mM (FIG. 6A), k=0.8, alpha=1.04 and resolution Rs=1.0. As the surfactant concentration was increased to 100 mM (FIG. 6B), k increased to 2.2, and the resolution to 2.5, with alpha remaining constant. In this manner, partitioning was optimized by changing the surfactant concentration. In order to optimize the system for samples with large k's, a much lower surfactant concentration can be employed. As seen in FIG. 7, propranolol was almost totally partitioned within the micelle at 25 mM (FIG. 7A), with no enantiomeric resolution. However, by lowering the concentration to 5 mM (FIG. 7B) and decreasing k, resolution emerges. However, as the detergent concentration is lowered to the range of the cmc, plates rapidly decrease.

Example 13

Effect of a Change in Hydrophobicity

Another way to modulate partitioning is to change the hydrophobic character of the surfactant. FIG. 8 shows a chiral separation of the hydrophobic racemate oxprenolol using a valine modified Brij-30 detergent (FIG. 3f). Because the Brij surfactant is more hydrophilic than the previously used hydrocarbons, hydrophobic analytes which partition too strongly into the micelles of the previous example show the desired reduction in partitioning and improved separations. Other chain compositions such as polyethers and glycols are also possible.

Example 14

Effect of Halogenated Tail Hydrocarbons

It is also possible to modulate the partitioning through halogenation of the hydrocarbon chain of the surfactant. FIG. 9 shows a separation of bupivacaine employing a valine modified fluorinated hydrocarbon (FIG. 3z). The corresponding hydrocarbon surfactant does not even form micelles under these conditions.

Example 15

Effect of Changing Hydrophobicity of the Electrolyte

Figure 10:
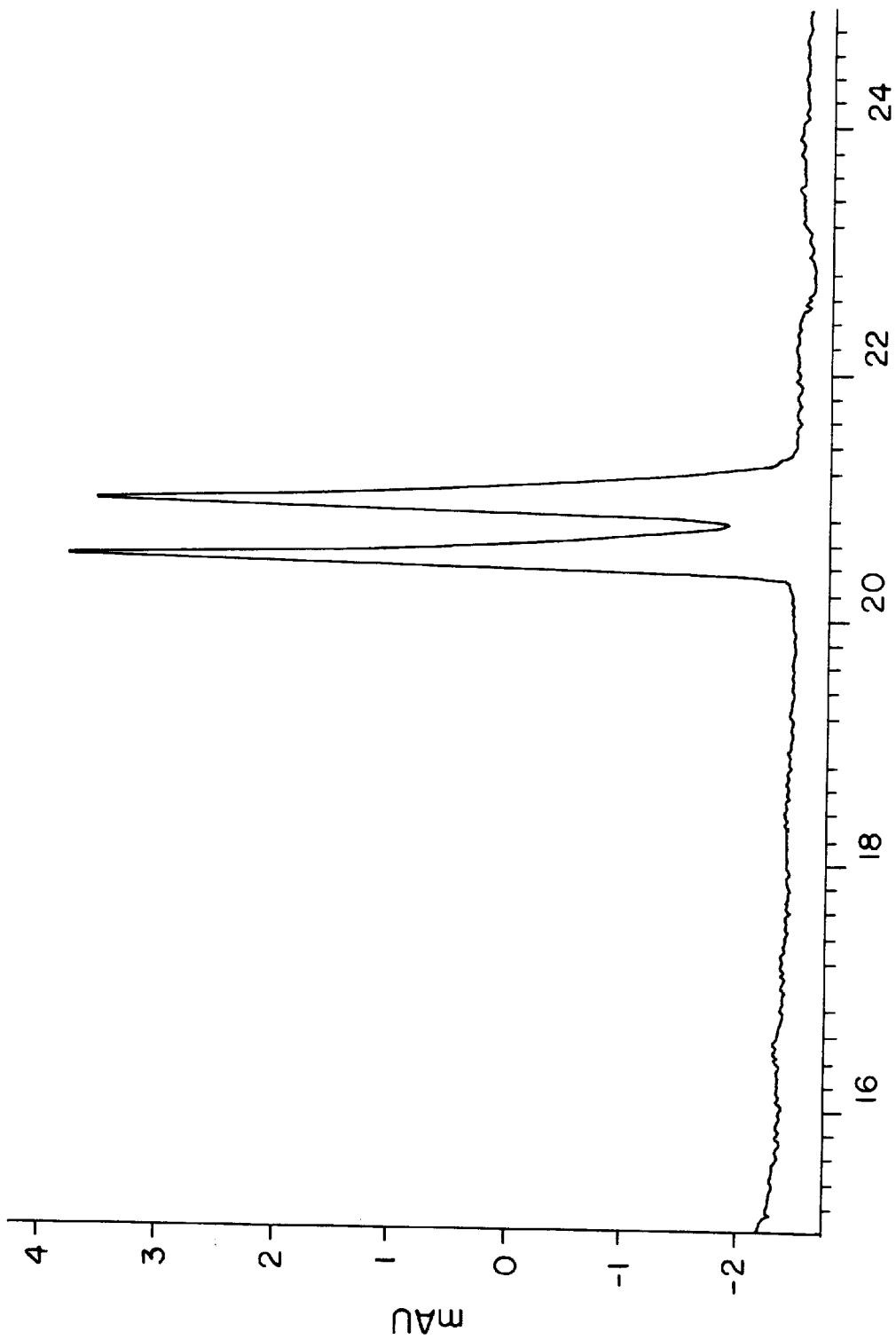
FIG. 10 is a chiral separation of the hydrophobic analyte propranolol with 25 mM (S)-N-dodecoxycarbonylvaline and 30% acetonitrile.

Partitioning can also be altered by adding organic solvent to the MEKC buffer. This is shown in FIG. 10, where propranolol is separated with 25 mM (S)-N-Dodecoxycarbonylvaline (FIG. 3a) and 30% acetonitrile. Recall that in FIG. 7A, propranolol was completely partitioned into the micelle at 25 mM in the absence of organic solvent.

Example 16

Effect of Changing Chiral Selector on Selectivity

Figure 11A:
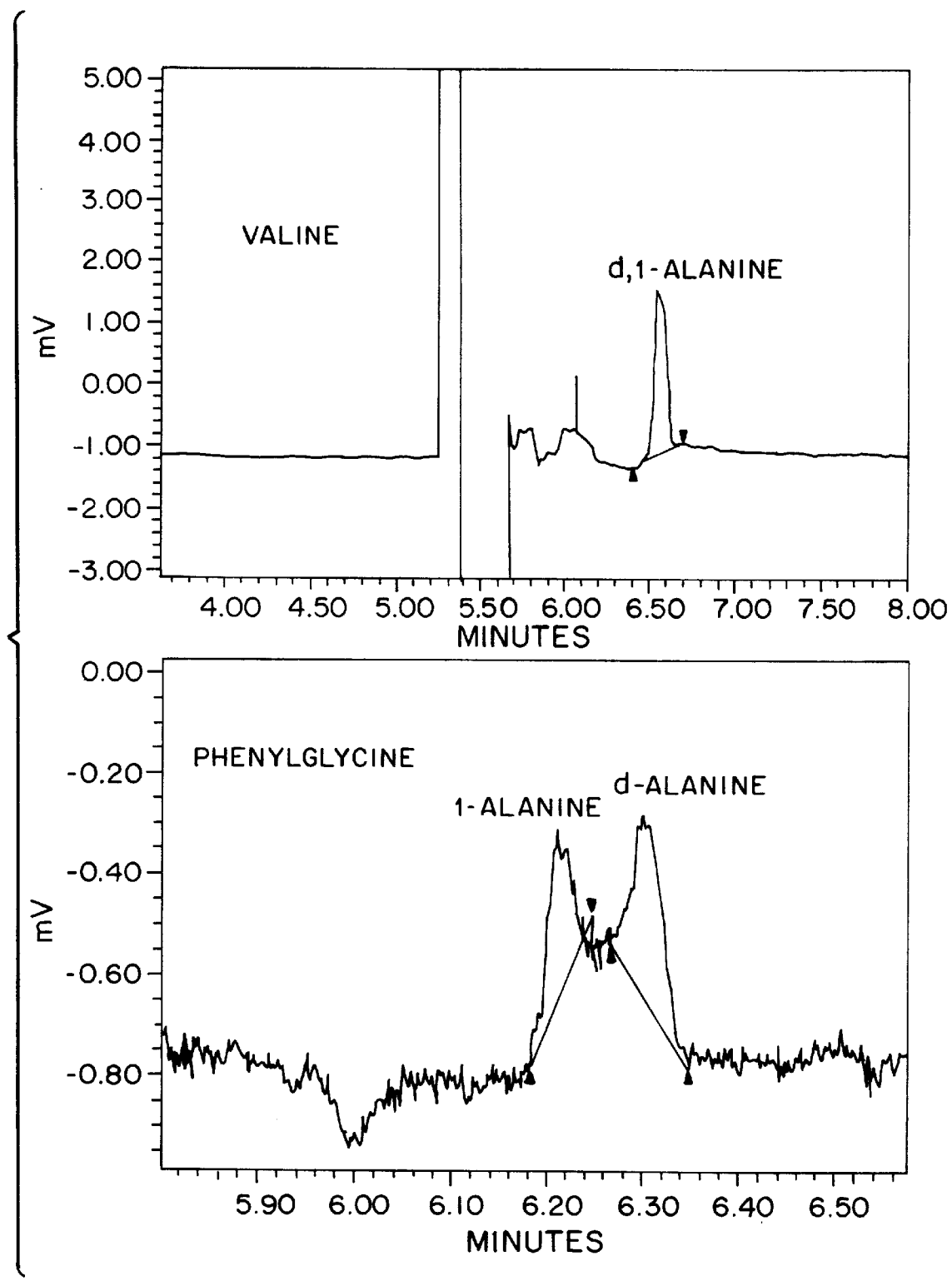
FIGS. 11(A & B) shows the separation of several PTH-amino acids using valine, phenylglycine, proline and serine based chiral surfactants.
Figure 11B:
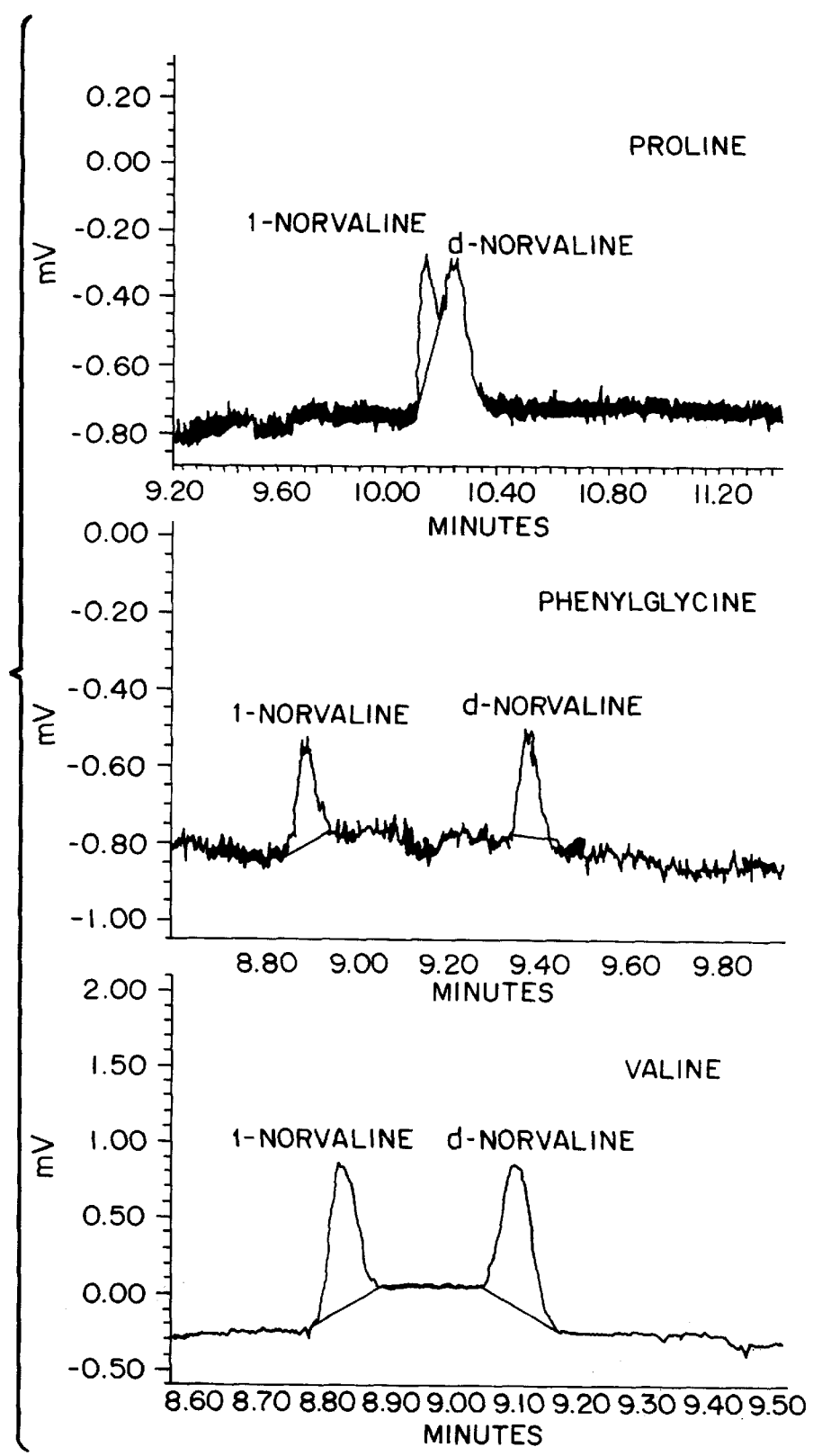
Figure 11C:
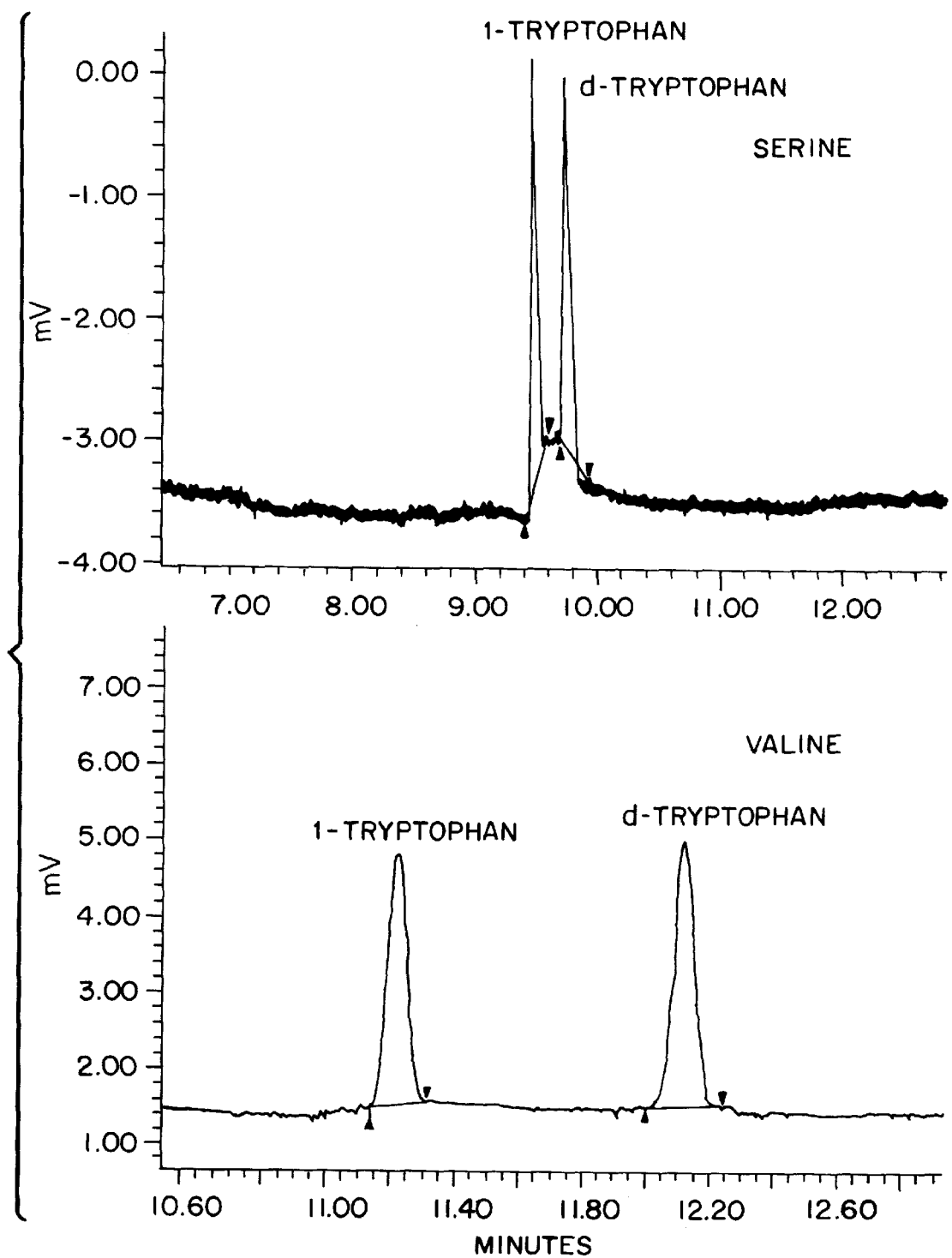
Figure 11D:
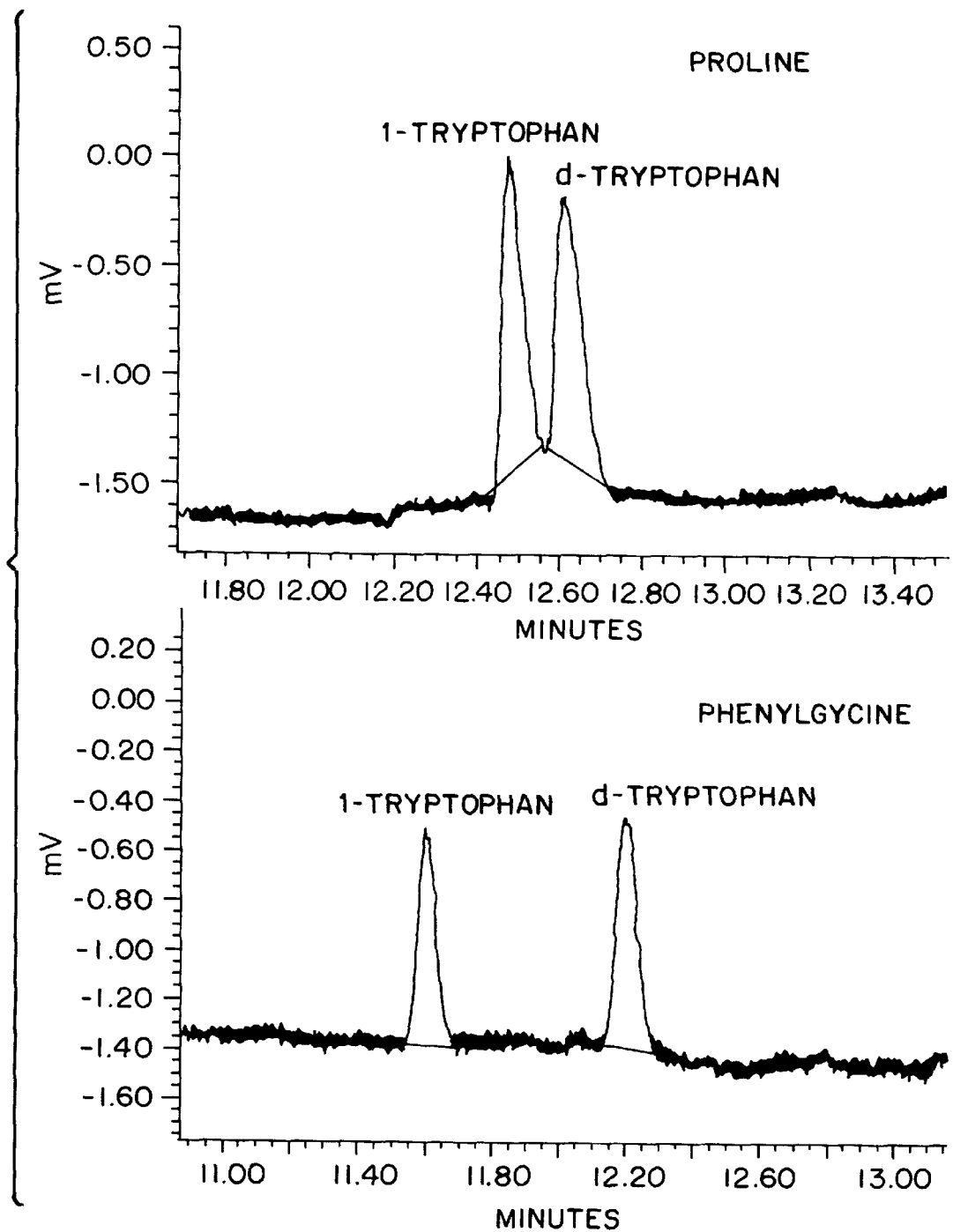

The selectivity of the chiral separation can be modulated by changing the chiral selector. A variety of amino acids may be employed. FIG. 11 shows the use of several amino acid-modified detergents at 25 mM concentration in the separation of some PTH-amino acids. FIG. 11A shows the separation of PTH-alanine with a valine-based surfactant (FIG. 3q) and a phenylglycine-based surfactant (FIG. 3s), with the phenylglycine surfactant showing resolution. FIG. 11B shows the separation of PTH-norvaline with proline- (FIG. 3u), phenylgycine- and valine-based surfactants. In this case, the phenylglycine surfactant shows the best resolution, although all three show some resolution. FIG. 11C and 11D show separation of PTH-tryptophan on serine- (FIG. 3t), valine-, proline- and phenylglycine-based surfactants, with the valine surfactant showing the best resolution. By using a screen of sample analytes it is clear that some amino acid selectors work better than others. These data are summarized in Table 2.

TABLE 2

Alpha Values for Several Enantiomeric Pairs Obtained with 6 Different Amino Acid-Modified Detergents

| Compound | Valine | Phenyl-glycine | Aspartic Acid | Serine | Pro-line | tertiary-Leucine |
|---|---|---|---|---|---|---|
| benzoin | 1.057 | 1.039 | 1.000 | 1.000 | 1.000 | 1.000 |
| PTH-alanine | 1.000 | 1.067 | 1.000 | — | 1.000 | 1.000 |
| PTH-norleucine | 1.122 | 1.213 | 1.000 | 1.096 | 1.000 | 1.000 |
| PTH-norvaline | 1.119 | 1.181 | 1.000 | 1.000 | 1.040 | 1.000 |
| PTH-serine | 1.000 | — | 1.000 | — | — | 1.000 |
| PTH-tryptophan | 1.266 | 1.196 | 1.000 | 1.108 | 1.036 | 1.000 |
| PTH-valine | 1.125 | 1.180 | 1.000 | 1.116 | 1.035 | 1.000 |

Non-amino acid chiral selectors may also be employed. Amino alcohols, organic acids including tartaric acids, cyclodextrins, sugar monomers, oligosaccharides, and other organic chiral molecules may be employed for this purpose. Examples using valinol (FIG. 3k)(12A), tartaric acid (FIG. 3A7) (12B) and (1S,2S)-N-2-amino-1-phenyl-1,3-propranedioldodecanamide (FIG. 3A5)(12C) are seen in FIG. 12.

Example 17
Effect of Linker on Selectivity

The immediate chemical environment of the chiral center may also lead to important changes in selectivity. An unexpectedly effective way to modulate the environment of the chiral center is by changing the chemical group that links the chiral center to the hydrophobic tail of the surfactant. As seen in FIG. 13, the use of sulfonamide (FIG. 3h)(13A), urea (FIG. 3g)(13B), and carbamate (FIG. 3a)(13C) linkers can change the selectivity of a particular separation dramatically. Table 3 shows a list of 14 compounds that have been screened under a single set of conditions using surfactants containing these three linkers.

TABLE 3

Alpha and Resolution Difference of 14 Test Racemates on Urea, Sulfonamide and Carbamate Linked Surfactants

| Analyte | Urea α | Carbamate α | Sulfonamid α | Urea Rs | Carbamate Rs | Sulfonamid Rs |
|---|---|---|---|---|---|---|
| atenolol | 1.03 | 1.04 | 1.02 | 0.30 | 0.80 | 0.50 |
| bupivacaine | 1.14 | 1.05 | 1.04 | 2.16 | 1.16 | 0.80 |
| ephedrine | 1.09 | 1.10 | 1.08 | 1.56 | 1.81 | 0.89 |
| homatotropine | 1.10 | 1.03 | 1.00 | 1.20 | 0 | 0 |
| ketamine | 1.04 | 1.01 | 1.00 | 1.03 | 0.24 | 0 |
| metoprolol | 1.03 | 1.06 | 1.00 | 0.20 | 1.00 | 0 |
| N-methyl-pseudoephedrine | 1.04 | 1.32 | 1.29 | 0.25 | 2.50 | 2.00 |
| nadolol (1) | 1.02 | 1.03 | 1.04 | 0.30 | 0.55 | 1.15 |
| nadolol (2) | 1.00 | 1.00 | 1.05 | 0 | 0 | 0.86 |
| norephedrine | 1.06 | 1.10 | 1.06 | 1.16 | 1.74 | 1.05 |
| norphenylephrine | 1.05 | 1.09 | 1.06 | 0.90 | 1.79 | 0.73 |
| octopamine | 1.02 | 1.05 | 1.02 | 0.60 | 0.54 | 0.23 |
| pindolol | 1.03 | 1.06 | 1.04 | 0.25 | 1.06 | 0.73 |
| terbutaline | 1.06 | 1.01 | 1.03 | 2.12 | 0.40 | 0.69 |

Clearly, optimum selectivity and resolution are dependent upon the specific interaction of the sample analyte and the surfactant. Although differences in alpha that are shown in Table 3 appear small, a difference of 0.01–0.03 can dramatically improve performance. FIG. 14 shows an example of a chiral separation with alphas of 1.01 (14A, carbamate linker) and 1.04(14B, urea linker). Given similar plates and partitioning, this represents a four-fold increase in resolution. The improvement in the quality of the separation in dramatic. The surfactants can also be used in mixtures that perform more separations than a given single surfactant. Table 4 shows data for a termolecular mixture of these surfactants which is effective in separating 13 of 14 compounds.

TABLE 4

Separation Data for 14 Racemates Separated with 15 mM each of Sulfonamide-, Urea- and Carbamate-Linked Surfactants

| Analyte | k | Rs | α measured |
|---|---|---|---|
| atenolol | 2.18 | 1.20 | 1.03 |
| bupivacaine | 10.9 | 2.22 | 1.06 |
| ephedrine | 5.18 | 3.06 | 1.07 |
| homatotropine | 4.74 | 2.07 | 1.04 |
| ketamine | 3.28 | 1.05 | 1.02 |
| metoprolol | 8.42 | 1.53 | 1.03 |
| N-methyl-pseudoephedrine | 2.80 | 6.17 | 1.19 |
| nadolol (1) | 4.49 | 1.60 | 1.04 |
| nadolol (2) | 4.72 | 1.12 | 1.05 |
| norephedrine | 4.39 | 2.67 | 1.06 |
| norphenyl-ephrine | 1.69 | 2.87 | 1.08 |
| octopamine | 0.97 | 1.16 | 1.03 |
| pindolol | 7.09 | 1.73 | 1.04 |
| terbutaline | 2.88 | 0 | 1.00 |

There is no one universal chiral center, linker, tail or head group that solves all problems. Flexibility to change the selectivity and partitioning is critical to the overall success in chiral separations. Unlike the circumstance of HPLC or GC where changing columns involves operator intervention, many CE instruments allow automated buffer selection. Thus, a set of surfactants as described herein can be automatically screened to identify the best separation.

Example 18
Effect of pH on Chiral Separations

Figure 3M:
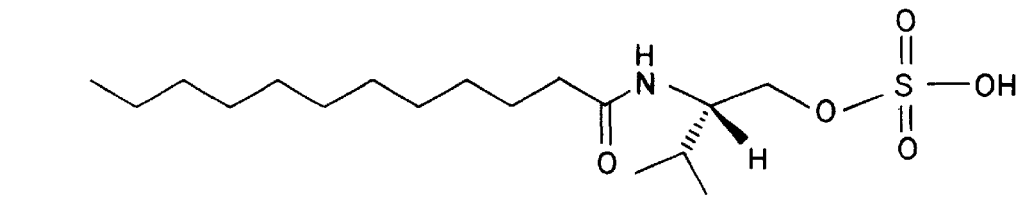

As mentioned above, in the normal operation of this invention, the analyte must partition within the micelle. In some cases this interaction can be modulated by changing the pH of the aqueous environment. For instance, negatively charged analytes typically do not partition into negatively charged micelles. Examples of two acids are shown in FIG. 15. However, if the pH is lowered so the carboxylic acid functionalities of the analyte are protonated, then the now-neutral analyte can more easily partition within the micelle. However, previously demonstrated embodiments of this invention also contain a carboxylate functionality that is essential to the solubility of the surfactant. When these surfactants are rendered neutral, they are no longer soluble. Therefore, a charged head group that will retain its charge throughout the usable pH range would allow the separation of acids. However, the addition of a different head group, such as sulfate dramatically changes this property. In one embodiment a sulfate group is substituted for a carboxylate functionality in a C12 amide-linked valinol detergent (FIG. 3m). Separations may now be conducted down to pH 2.0 using this surfactant. FIG. 16 shows chiral separations of the organic acids n FIG. 15 that were not possible at elevated pH of 6 or above (16A is proglumide, 16B CBZ-tryptophan). Other head groups such as sulfonic acids, sulfonates, alcohols, and diols are also possible.

Figure 17:
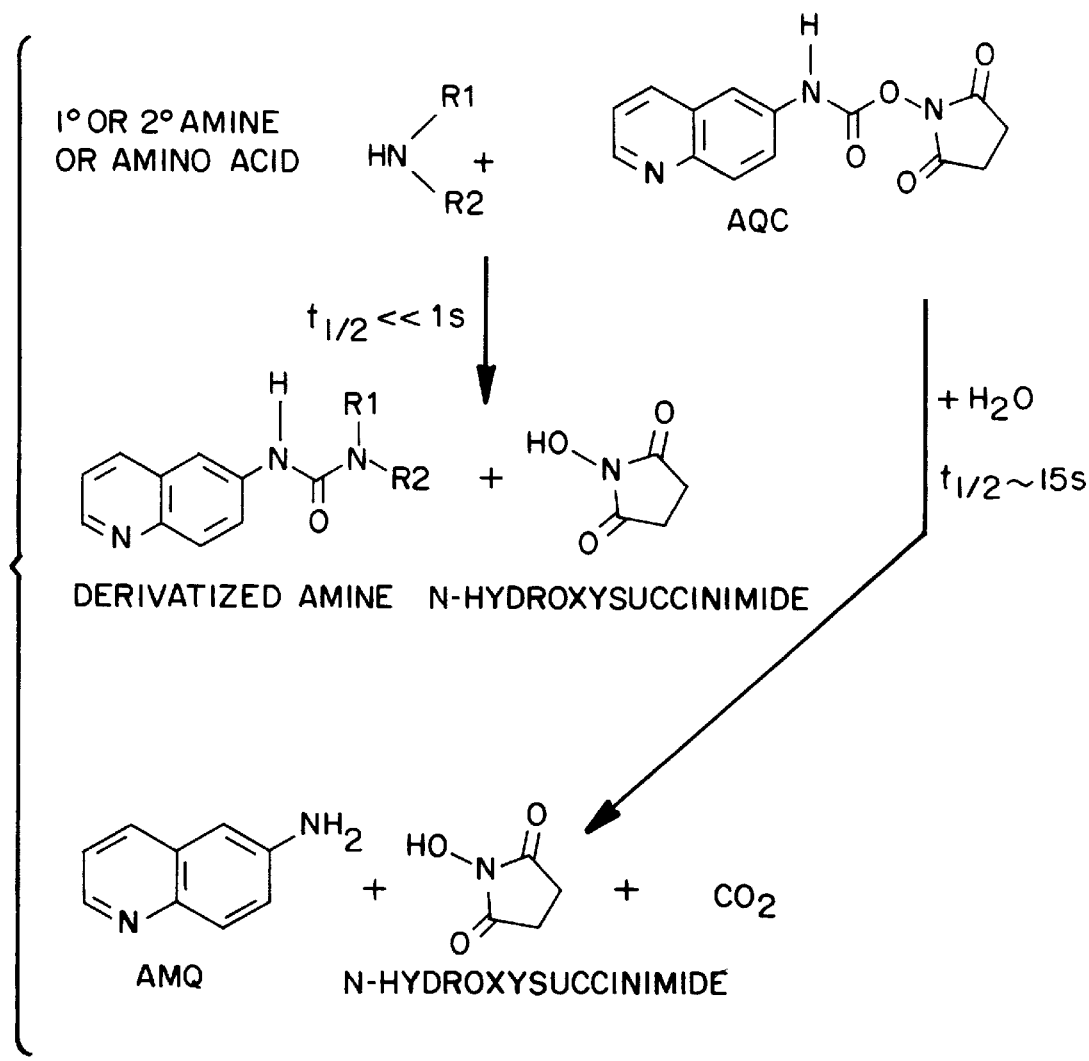
FIG. 17 provides the reaction sequence of a primary or secondary amine to provide N-6-quinolylaminocarbonyl-tagged derivatives.
Figure 18:
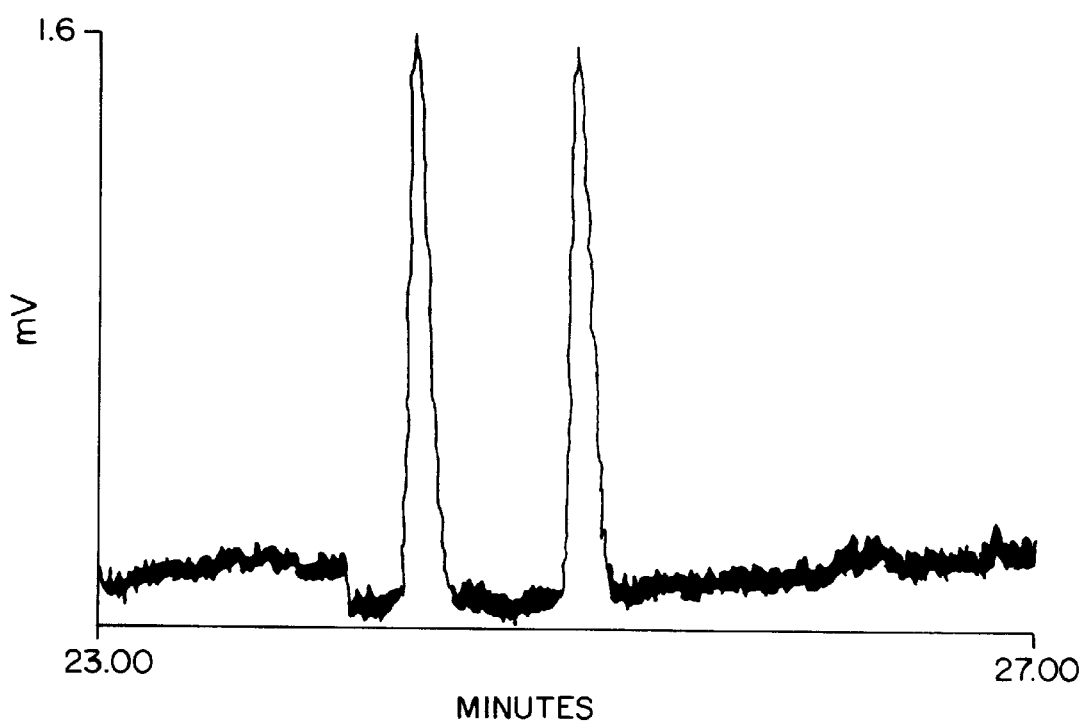
FIG. 18 shows the chiral separation of a racemic N-6-quinolylaminocarbonylarginine using 100 mM (S)-N-dodecoxycarbonylvaline.

Another type of molecule that was separated using the present invention are 6-quinolylaminocarbonyl-tagged amino containing compounds, as shown in FIG. 17. A typical separation is shown in FIG. 18.

Example 19
Effect of Electroosmotic Flow

Figure 20A:
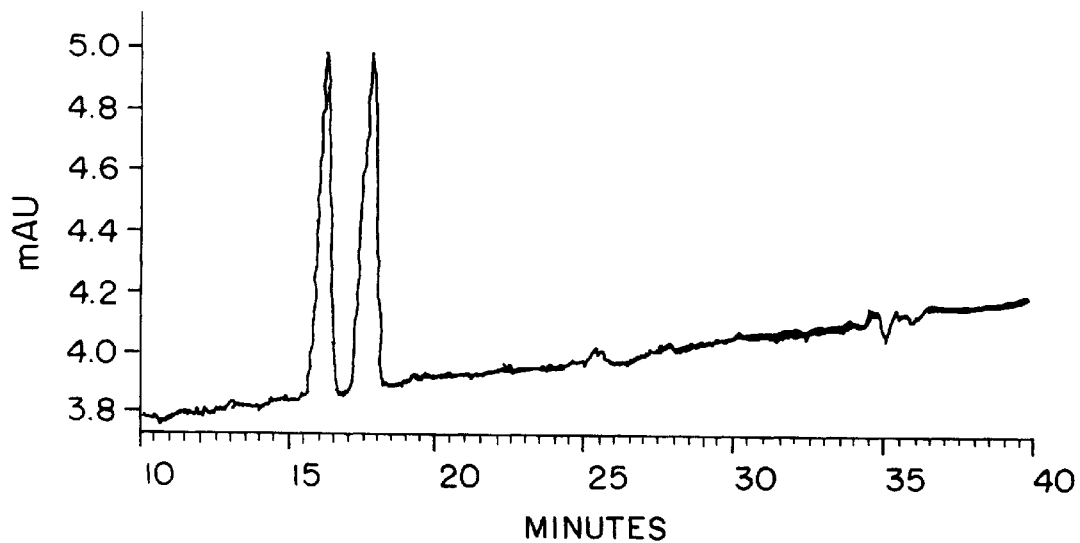
FIG. 20(A) shows chiral separation of ephedrine obtained in a coated capillary at pH 7 with an electroosmotic mobility of 0.7×10−4 cm2/Vs using 25 mM (S)-N-dedecoxycarbonylvaline.
Figure 20B:
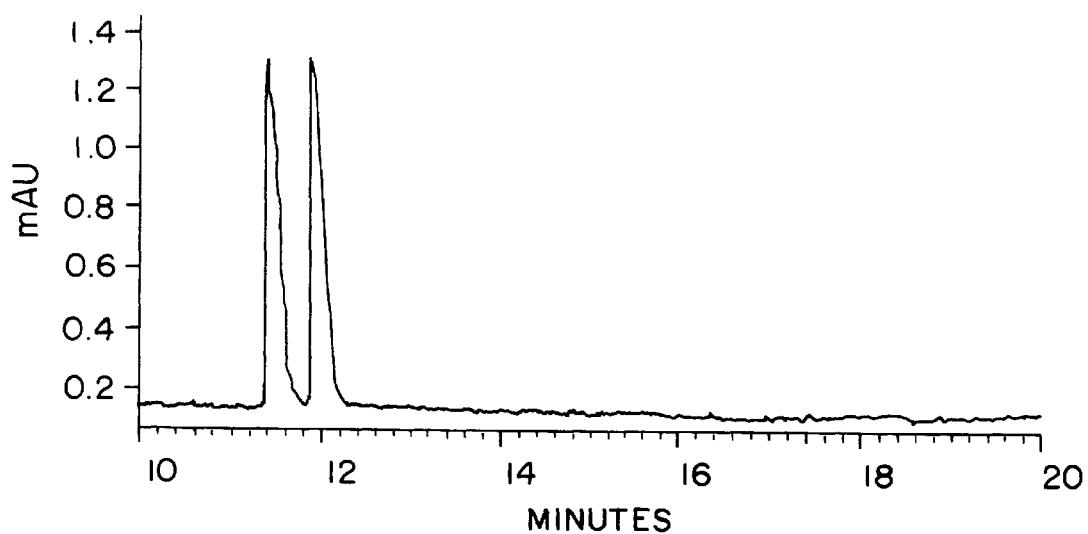
FIG. 20(B) shows chiral separation of ephedrine obtained in a uncoated capillary at pH 7 with an electroosmotic mobility of 5.7×10−4 cm2/Vs using 25 mM (S)-N-dodecoxycarbonylvaline.

One of the side effects of electrophoresis in a fused silica capillary tube can be a bulk fluid flow called electroosmotic flow. This fluid flow moves all components of the separation at the same velocity through the capillary, without contributing to the resolution of the chiral separation. This is demonstrated in FIG. 19. At pH 4.0 (19A), the mobility of the osmotic flow was $1.4 \times 10^{-4}$ cm$^2$/Vs, while the micelle mobility is $-4.4 \times 10^{-4}$ cm$^2$/Vs. When the pH was increased to 6.0 (19B) the micelle mobility remained the same, while the osmotic mobility increases 2.28×. This enhancement of the electroosmotic flow had no impact on the observed resolution, but resulted in an overall increase in the analysis time of several minutes. In a different embodiment of this invention, the electroosmotic flow was greatly reduced with the use of a fused silica capillary with a modified wall chemistry. An embodiment of this is shown in FIG. 20, using 25 mM (S)-N-dodecoxycarbonylvaline at pH 7 (coated capillary is 20A, $\mu$os=$0.7 \times 10^{-4}$ cm$^2$/Vs, uncoated capillary 20B, $\mu$os=$5.7 \times 10$–4 cm$^2$/Vs). In this case, the presence of the osmotic flow reduces the analysis time, but does not improve resolution.

Example 20
Detection of Ephedrine Enantiomers in Urine

MEKC s also useful for performing separations in physiological samples. FIG. 21 is a electropherogram showing the separation of ephedrine enantiomers in untreated urine. FIG. 21(A) is 100 ug/ml racemic ephedrine standard solution. Baseline separation occurs between 17 and 18 minutes. FIG. 21(B) is a sample of 100 ug/ml ephedrine-spiked urine run under the same conditions, with separation occurring at approximately the same time. FIG. 21(C) is a urine blank. Note the absence of any interfering peaks in the area between 17 and 18 minutes. The ability to separate both chiral and achiral compounds in the urine sample illustrates the broad applicability of this method.

Conditions: capillary 50 um i.d. by 60 cm length; + . kV applied voltage; detection at 214 nm, 0.1 second time constant; data aquisition at 10 points/sec.; injection over 5 secs. Buffer was 25 mM phosphate/borate, pH 8.8, with 50 mM N-dodecoxycarbonylvaline. Sample preparation consisted of filtration only.

Example 21
Tail potentiating enantioselectivity

To demonstrate that the tail potentiates enantioselectivity, alpha values obtained for ten analytes were compared using four novel chiral surfactants which have the same linker (carbamate), chiral selector (valine) and head (carboxylate), but different tails. The four novel chiral surfactants were (S)-N-dodecyloxyethylene-(4oxycarbonylvaline (FIG. 3f, Brij-30 tail), (S)-N-dodecoxycarbonylvaline (FIG. 3a, linear hydrocarbon tail), (S)-N-(2R)-octoxycarbonylvaline (FIG. 3av, chiral (R), branched hydrocarbon tail), and (S)-N-(2S)-octoxycarbonylvaline (FIG. 3au, chiral (S) branched hydrocarbon tail). All separations were performed at pH 8.8 with either 25 mM (straight hydrocarbon tail), 50 mM (Brij-30 tail) or 100 mM (R and S branched hydrocarbon tails) surfactant.

Alphas for the test compounds on each tail are given in Table 5 below. The linear hydrocarbon tail generally had the highest alpha, except in the cases of nadolol, octopamine and terbutaline. For terbutaline, (S)-N-(2R)-octoxycarbonylvaline (R tail) had the highest alpha, for nadolol (1)(S)-N)(2S)-octoxycarbonylvaline (S tail) had the highest alpha, for nadolol (2)(S)-N-dodecyloxyethylene-(4)oxycarbonylvaline had the highest alpha, and for octopamine (S)-N-(2S)-octoxycarbonylvaline (S tail) had the highest alpha. Note that for all compounds the alphas were different on at least one of the tails.

TABLE 5

| Analyte | Brij-30 Tail α | Hydrocarbon Tail α | Chiral R Tail α | Chiral S Tail α |
| --- | --- | --- | --- | --- |
| bupivacaine | 1.02 | 1.05 | 1.01 | 1.02 |
| ephedrine | 1.03 | 1.10 | 1.07 | 1.10 |
| homatropine | 1.01 | 1.03 | 1.03 | 1.02 |
| ketamine | 1.00 | 1.01 | 1.00 | 1.00 |
| nadolol (1) | 1.03 | 1.03 | 1.03 | 1.04 |
| nadolol (2) | 1.04 | 1.00 | 1.00 | 1.00 |
| norphenylephrine | 1.05 | 1.09 | 1.06 | 1.09 |
| octopamine | 1.03 | 1.05 | 1.04 | 1.07 |
| pindolol | 1.04 | 1.06 | 1.05 | 1.05 |
| terbutaline | 1.03 | 1.01 | 1.05 | 1.00 |

Other tail types also influence enantioselectivity. Table 6 compares enantioselectivity data obtained with (S)-N-perfluorooctanoyl-(L)-valine (perfluoro tail, amide linker, valine chiral selector, carboxylate head) to (S)-N-dodecanoylvaline (hydrocarbon tail, amide linker, valine chiral selector, carboxylate head). In all cases, the two tails showed different enantioselectivity values. Conditions were 25 mM surfactant at pH 8.8

TABLE 6

| Analyte | Perfluoro Tail α | Hydrocarbon Tail α |
| --- | --- | --- |
| bupivacaine | 1.07 | 1.06 |
| ephedrine | 1.04 | 1.05 |
| homatropine | 1.00 | 1.02 |
| metoprolol | 1.00 | 1.01 |
| nadolol (1) | 1.03 | 1.00 |
| nadolol (2) | 1.02 | 1.00 |
| terbutaline | 1.03 | 1.00 |

Example 22
Head Potentiating Enantioselectivity

Figure 3N:
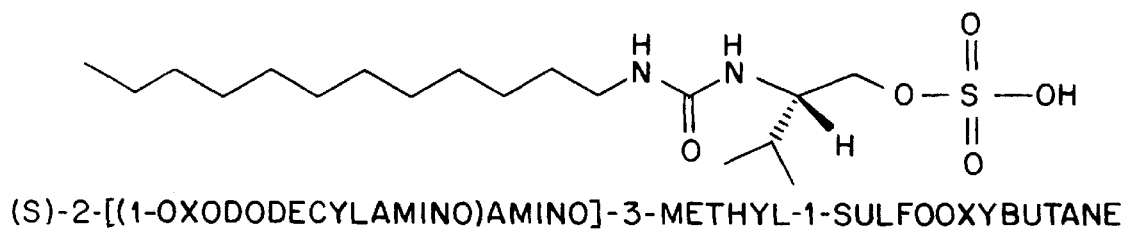
Figure 3O:
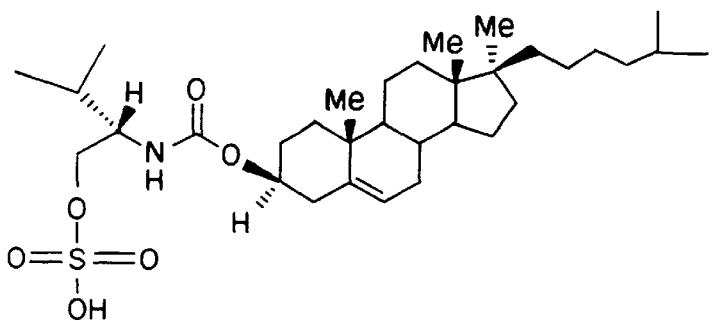
Figure 3P:
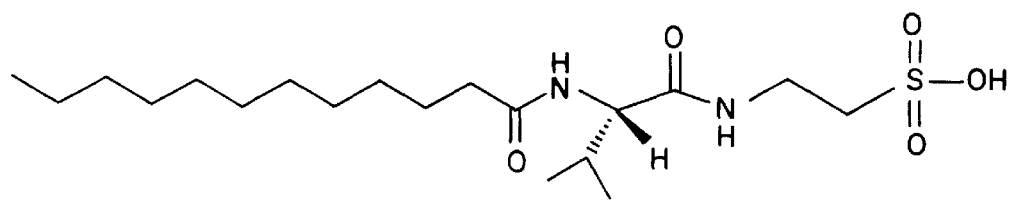
Figure 3Q:
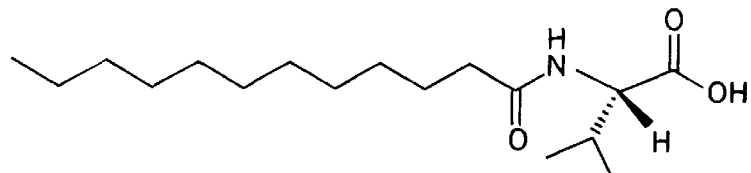
Figure 3R:
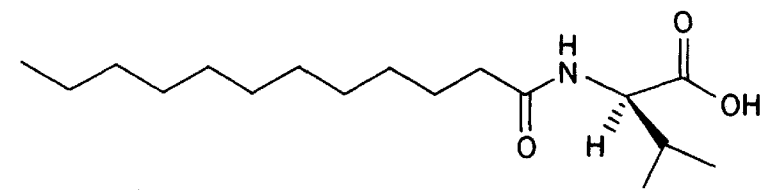
Figure 3S:
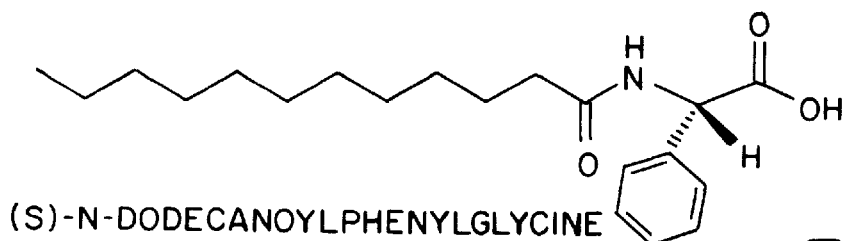
Figure 3T:
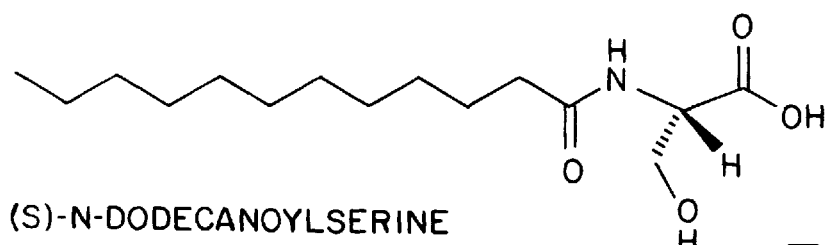
Figure 3U:
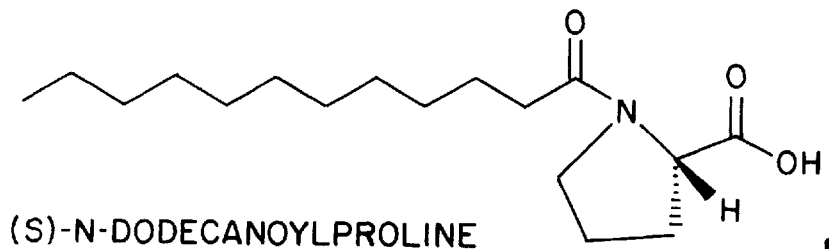
Figure 3V:
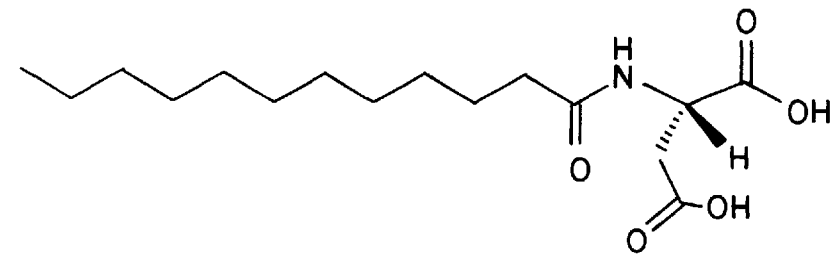

To demonstrate that the hydrophilic head potentiates enantioselectivity, alpha values obtained for eleven compounds on six novel chiral surfactants were compared. These six surfactants all have C12 tails and valine-based chiral selectors. Sulfate and carboxylate head groups were compared for three linkers (amide, carbamate and urea). The six novel surfactants are (S)-N-dodecanoylvaline (FIG. 3q, amide-valine-carboxylate), (S)-N-dodecoxycarbonylvaline (FIG. 3a, carbamate-valine-carboxylate), (S)-N-dodecylaminocarbonylvaline (FIG. 3g, urea-valine-carboxylate), (S)-2-[(1-oxododecyl)-amino]-3-methyl-1-sulfooxybutane (FIG. 3m, amide-valinol-sulfate), (S)-2-[(1-oxododecoxy)amino]3-methyl-1-sulfooxybutane (FIG. 3l, carbamate-valinol-sulfate) and (S)-2-[(1-oxododecylamino)amino]-3-methyl-1-sulfooxybutane (FIG. 3n, urea-valinol-sulfate). Conditions were 25 mM surfactant at pH 8.8.

Table 7 below gives the comparison data of sulfate vs. carboxylate for each linker. In most cases the alpha was different due to the two head groups. In general, the carboxylate head group was superior.

TABLE 7

| | Amide | | Carbamate | | Urea | |
|---|---|---|---|---|---|---|
| Analyte | Sulfate α | Carbox. α | Sulfate α | Carbox. α | Sulfate α | Carbox. α |
| atenolol | 1.01 | 1.00 | 1.05 | 1.04 | 1.00 | 1.03 |
| bupivacaine | 1.10 | 1.06 | 1.08 | 1.05 | 1.09 | 1.14 |
| homatropine | 1.00 | 1.02 | 1.01 | 1.03 | 1.06 | 1.10 |
| ketamine | 1.02 | 1.05 | 1.02 | 1.01 | 1.02 | 1.04 |
| metoprolol | 1.00 | 1.01 | 1.05 | 1.06 | 1.00 | 1.03 |
| nadolol (1) | 1.03 | 1.00 | 1.02 | 1.03 | 1.03 | 1.02 |
| nadolol (2) | 1.03 | 1.00 | 1.14 | 1.00 | 1.00 | 1.00 |
| norphenyl-ephrine | 1.02 | 1.09 | 1.03 | 1.09 | 1.02 | 1.05 |
| octopamine | 1.00 | 1.00 | 1.00 | 1.05 | 1.00 | 1.02 |
| pindolol | 1.00 | 1.02 | 1.04 | 1.06 | 1.00 | 1.03 |
| tetbutaline | 1.00 | 1.00 | 1.02 | 1.01 | 1.04 | 1.06 |

Figure 22A:
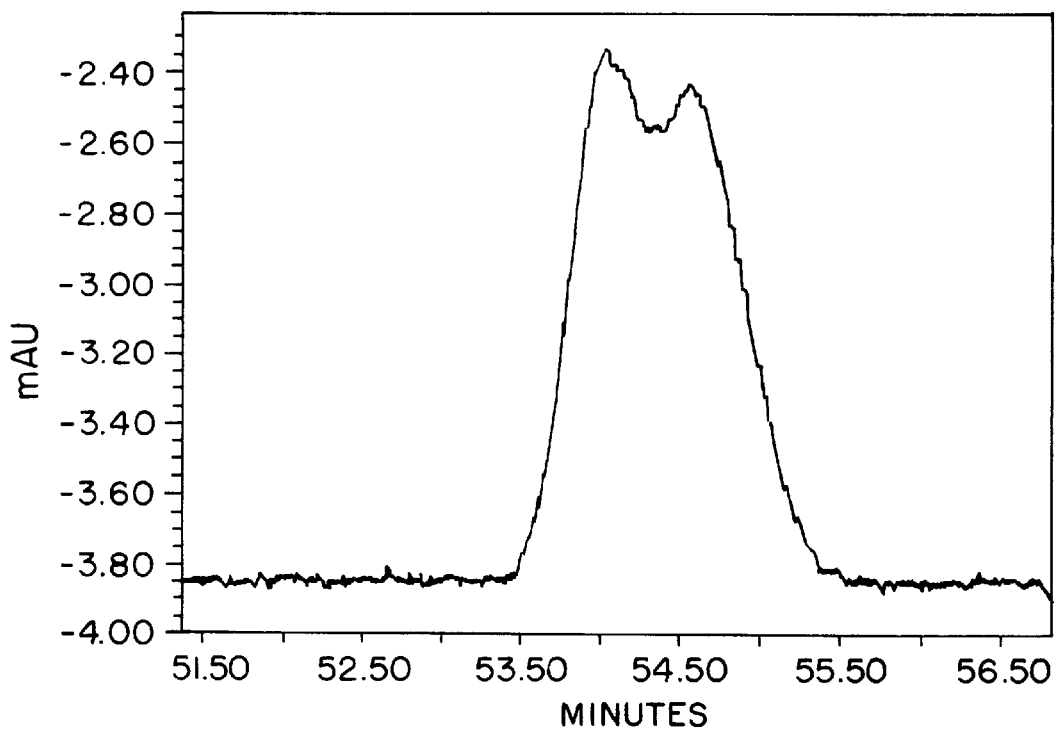
FIGS. 22(A)–(B) are chromatograms showing the separation of N-benzoyl-DL-alanine with (S)-2-[(1-oxododecyl)amino]-4-methyl-1-sulfooxypentane (FIG. 3bd, C12-amide-leucinol-sulfate)
Figure 22B:
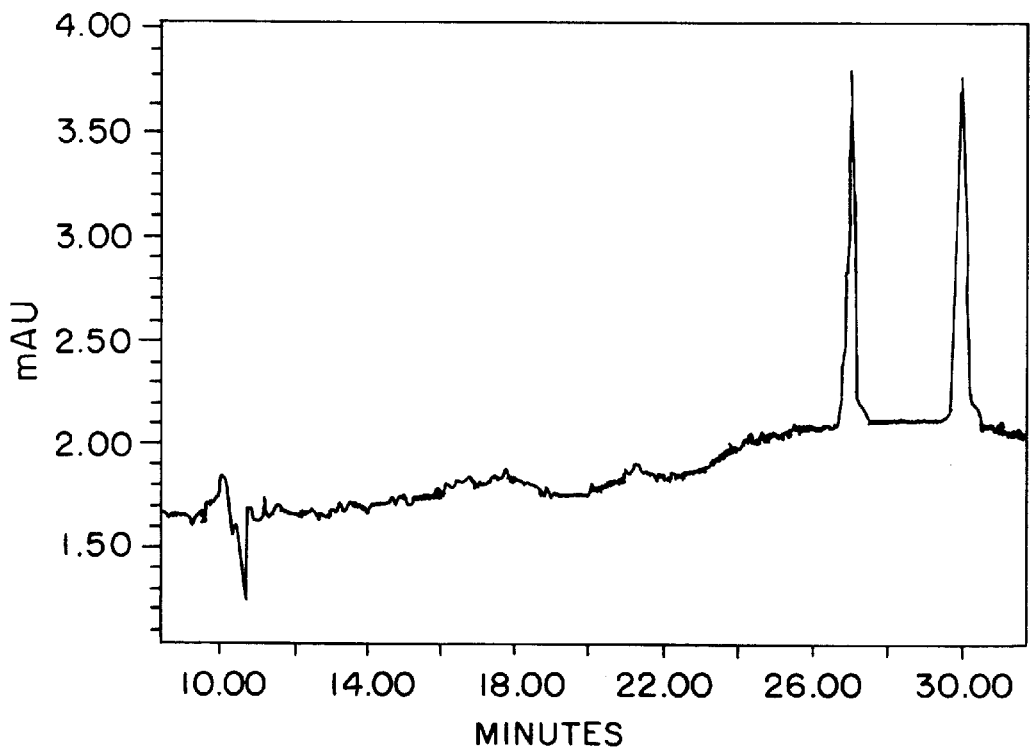

Changing the charge on the head group can also dramatically influence enantioselectivity, and hence resolution. FIG. 22A shows the separation of N-benzoyl-DL-alanine with (S)-2-[(1-oxododecyl)amino]-4-methyl-1-sulfooxypentane (FIG. 3bd, C12-amide-leucinol-sulfate), while FIG. 22B shows the separation of the same compound on N-dodecyl-(S)-leucinamide hydrochloride (FIG. 3B12, C12-amide-leucine-ammonium salt). Superior enantioselectivity and resolution is obtained with the positively charged ammonium head group. Conditions were 25 mM surfactant at pH 3.0.

Example 23
Chiral Selector Potentiating Enantioselectivity

Comparison data for several novel chiral surfactants which have carbamate linkers, C12 tails and carboxylate heads, but different amino acid chiral selectors, is shown below in Table 8. Ten chiral bases were examined with (S)-N-dodecoxycarbonylalanine (FIG. 3A10), (S)-N-decoxycarbonylasparagine (FIG. 3A18), (2S,3S)-N-dodecoxycarbonylisoleucine (FIG. 3al), (S)-N-decoxycarbonylleucine (FIG. 3A11), (S)-N-dodecoxycarbonyltertleucine (FIG. 3c), (2S,3S)-N-dodecoxycarbonylthreonine (FIG. 3A19) and (S)-N-dedocoxycarbonylvaline (FIG. 3a). Enantioselectivity values obtained for the ten compounds on each amino acid derivative are given below. Conditions were 25 mM surfactant at pH 8.8.

Figure 23:
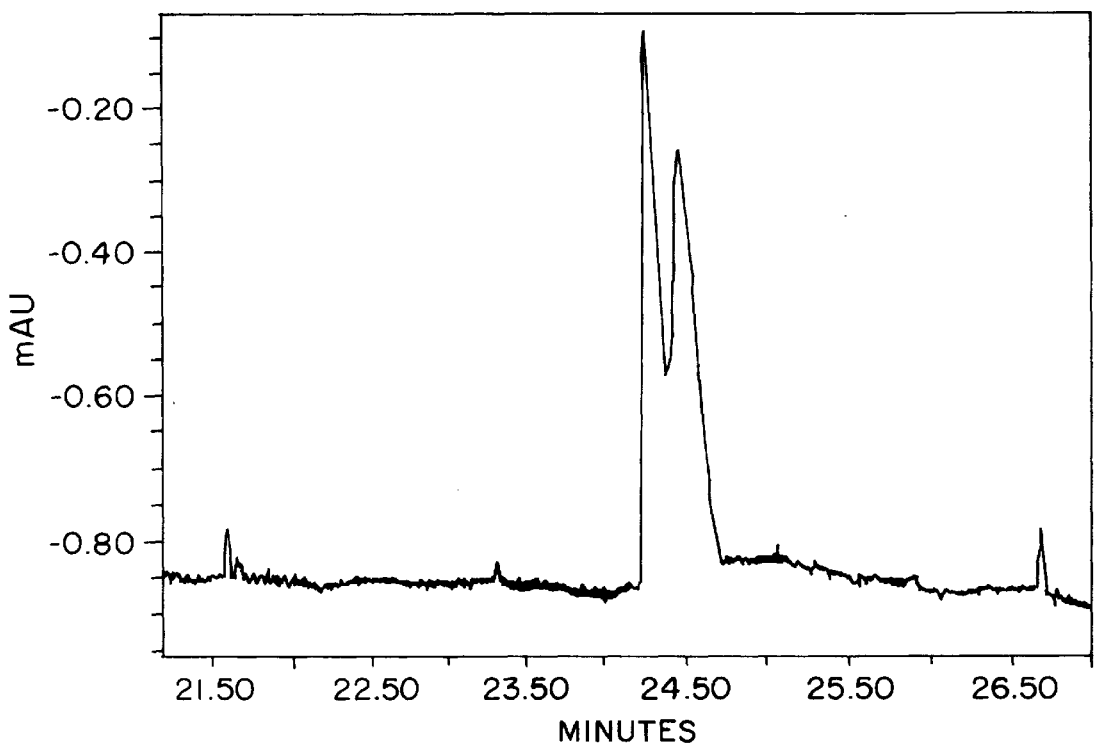
FIG. 23 is a chromatogram of the separation of amphetamine using the chiral surfactant (S)-N-dodecoxycarbonylleucine (FIG. 3ak).
Figure 24A:
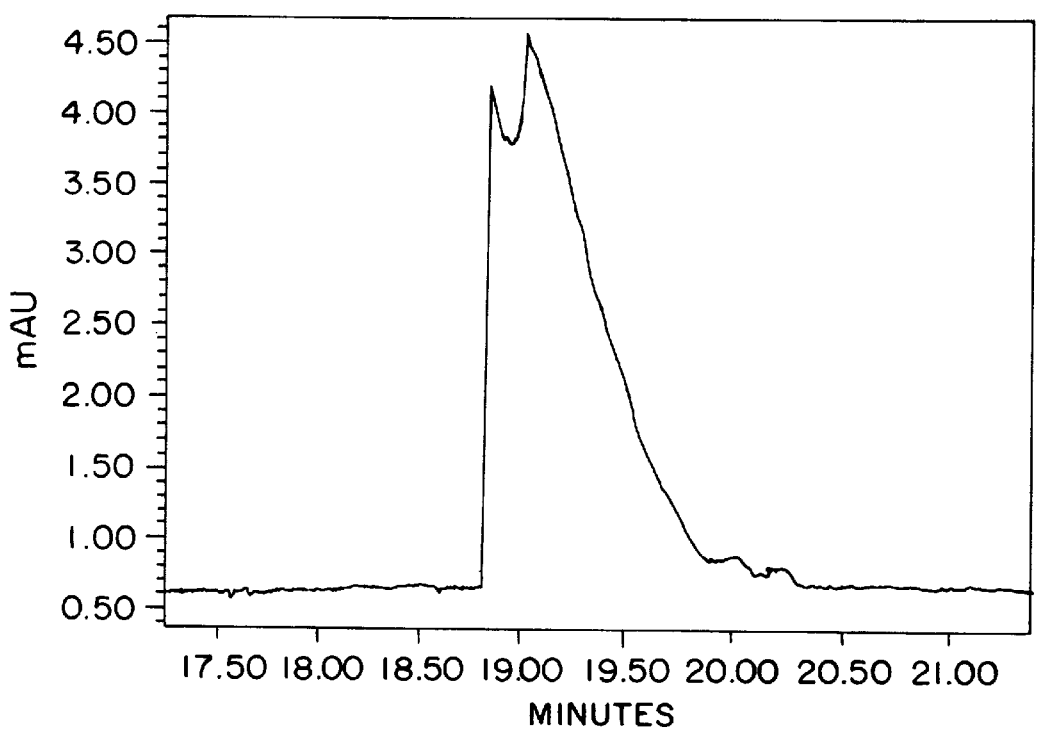
FIGS. 24(A)–(B) are chromatograms of the separation of amphetamine using the chiral surfactants (S)-N-dodecoxycarbonylcyclohexylalanine (FIG. 3ao, FIG. 24A), and (R,R)-N-decyltartaric acid monoamide, sodium salt (FIG. 3ag, FIG. 24B).
Figure 24B:
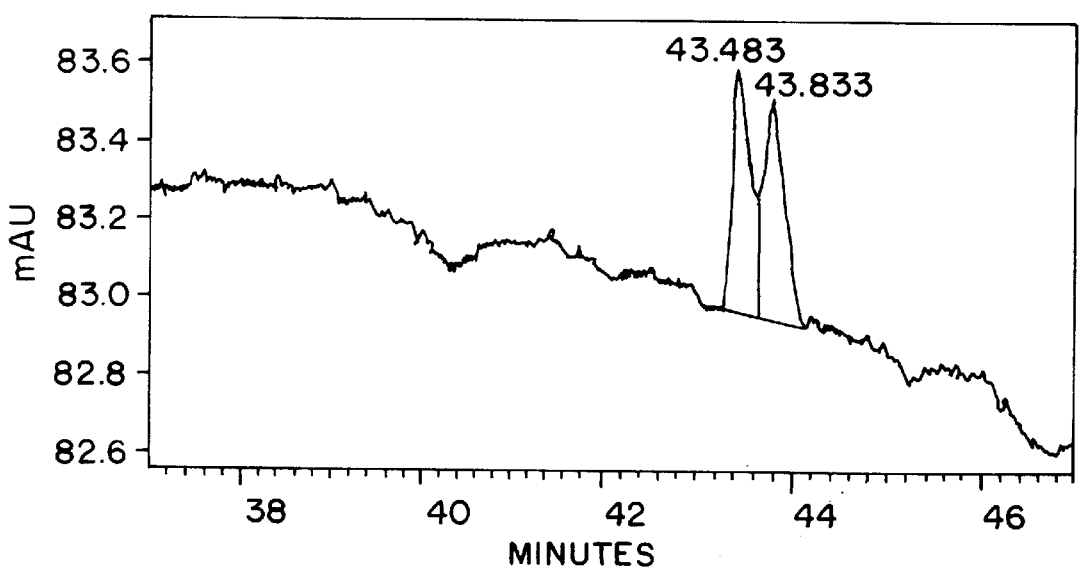

Overall, the leucine derivative showed superior enantioselectivity. Furthermore, it showed enantioselectivity for the chiral base amphetamine which contains only one hydrogen bonding site, see FIG. 23. Other chiral surfactants which have shown the ability to separate amphetamine are (S)-N-dodecoxycarbonylcyclohexylalanine (FIG. 3A15, FIG. 24A), and (R,R)-N-decyltartaric acid monoamide, sodium salt (FIG. 3A7, FIG. 24B).

TABLE 8

| Analyte | Ala | Asp | Ile | Leu | t-Leu | Thre | Val |
|---|---|---|---|---|---|---|---|
| amphetamine | 1.00 | 1.00 | 1.00 | 1.02 | 1.00 | 1.00 | 1.00 |
| bupivacaine | 1.03 | 1.00 | 1.13 | 1.03 | 1.06 | 1.09 | 1.05 |
| ephedrine | 1.08 | 1.04 | 1.11 | 1.14 | 1.09 | 1.07 | 1.10 |
| homatropine | 1.02 | 1.03 | 1.02 | 1.03 | 1.00 | 1.00 | 1.03 |
| ketamine | 1.01 | 1.00 | 1.01 | 1.02 | 1.02 | 1.00 | 1.01 |
| metoprolol | 1.04 | 1.03 | 1.06 | 1.08 | 1.04 | 1.05 | 1.06 |
| norephedrine | 1.07 | 1.04 | 1.10 | 1.11 | 1.09 | 1.07 | 1.10 |
| norphenylephrine | 1.10 | 1.04 | 1.08 | 1.10 | 1.06 | 1.07 | 1.09 |
| pindolol | 1.05 | 1.04 | 1.06 | 1.08 | 1.04 | 1.06 | 1.06 |
| terbutaline | 1.01 | 1.00 | 1.00 | 1.00 | 1.00 | 1.01 | 1.01 |

Example 24
Hydrophilic Head Groups Influence Partitioning

As previously demonstrated sulfate head groups have an advantage over carboxylate head groups in terms of their ability to be used at acidic pH. At acidic pH, separation of hydrophilic acids can be obtained since the charge on the acids is minimized and partitioning is higher than at neutral pH where they are fully anionic. The reason for the low partitioning at neutral pH is due to charge repulsion of the anionic analyte by the anionic micelle. A positively charged head group also leads to improved partitioning and resolution of anionic compounds, since charge attraction will increase partitioning. For example, FIG. 25 shows the separation of the anionic compound carboxybenzoyl-DL-alanine using 25 mM N-dodecyl-(S)-prolinamide hydrochloride (FIG. 3bn) at pH 3.0.

Example 25
pH Influencing Partitioning and Enantioselectivity

In this study, 25 mM (S)-N-dodecoxycarbonylvaline (FIG. 3a) was used to separate twelve basic analytes and one neutral one (benzoin) at pHs 7.0 and 8.8. Table 9 below gives free solution mobility data ($\mu$), capacity factor values (k) and alpha values for all thirteen compounds at the two pHs. For all the analytes except benzoin (neutral at both pHs), free solution mobility was higher at pH 7.0. These results were expected, since all the basic analytes contain amino groups with $pK_a$s in the pH 7–9 range. At lower pH, the compounds had more positive charge, leading to the increased mobility. For all the analytes except benzoin, capacity factor values were higher at pH 7.0, which is attributable to the increased ionic attraction between the anionic micelles and cationic analyte. Finally, alpha values were the same or higher for all the basic compounds at pH 7.0 vs. pH 8.8. Note especially the large increase in alpha for bupivacaine, ketamine and metoprolol. None of the bases showed lower enantioselectivity at pH 7.0

This data clearly indicates the importance of charge in determining partitioning and enantioselectivity for cationic analytes with anionic micelles. Similar trends should be expected with anionic analytes and cationic micelles.

TABLE 9

| | $\mu$ | | k | | α | |
|---|---|---|---|---|---|---|
| ANALYTE | pH 7.0 | pH 8.8 | pH 7.0 | pH 8.8 | pH 7.0 | pH 8.8 |
| atenolol | 1.44 | 1.29 | 1.94 | 1.56 | 1.05 | 1.04 |
| benzoin | 0 | 0 | 2.35 | 2.41 | 1.04 | 1.04 |
| bupivacaine | 1.54 | 0.41 | 40.5 | 7.62 | 1.26 | 1.05 |
| ephedrine | 2.16 | 1.79 | 6.60 | 3.77 | 1.14 | 1.10 |
| homatropine | 1.79 | 1.66 | 4.10 | 3.35 | 1.03 | 1.03 |

TABLE 9-continued

| ANALYTE | μ | | k | | α | |
|---|---|---|---|---|---|---|
| | pH 7.0 | pH 8.8 | pH 7.0 | pH 8.8 | pH 7.0 | pH 8.8 |
| ketamine | 1.58 | 0.13 | 12.5 | 2.20 | 1.06 | 1.01 |
| metoprolol | 1.58 | 1.30 | 26.5 | 7.44 | 1.19 | 1.06 |
| N-methyl-pseudo-ephedrine | 2.45 | 1.44 | 4.05 | 1.96 | 1.38 | 1.32 |
| nor-ephedrine | 2.18 | 1.42 | 6.10 | 3.44 | 1.12 | 1.10 |
| norphenyl-ephrin | 1.99 | 0.94 | 2.02 | 1.01 | 1.09 | 1.09 |
| octopamine | 1.97 | 1.03 | 1.09 | 0.64 | 1.05 | 1.05 |
| pindolol | 1.84 | 1.44 | 9.50 | 6.70 | 1.09 | 1.06 |
| terbutaline | 1.82 | 1.60 | 3.32 | 2.40 | 1.02 | 1.01 |

Example 26
Tail Length Enabling Solubility

In chiral surfactants containing carboxylate head groups, it was found that there is a minimum pH below which the surfactant is insoluble. This minimum pH value is a function of the length of the hydrocarbon tail. For instance, for surfactants containing a carbamate linker, valine chiral selector and carboxylate head group, the derivative with a C14 tail, (S)-N-tetradecoxycarbonylvaline, is insoluble below pH 7.5, the derivative with a C12 tail, (S)-N-dodecoxycarbonylvaline, is insoluble below pH 6.5, the derivative with a C10 tail, (S)-N-decoxycarbonylvaline, is insoluble below pH 5.5, the derivative with a C8 tail, (S)-N-octoxycarbonylvaline, is insoluble below pH 4.5. It is important to have a wide range of pH solubility, since enantioselectivity and partitioning is influenced by pH for ionizable compounds (see above). The tradeoff for the wider pH range of solubility is a higher critical micelle concentration (cmc).

Figure 26A:
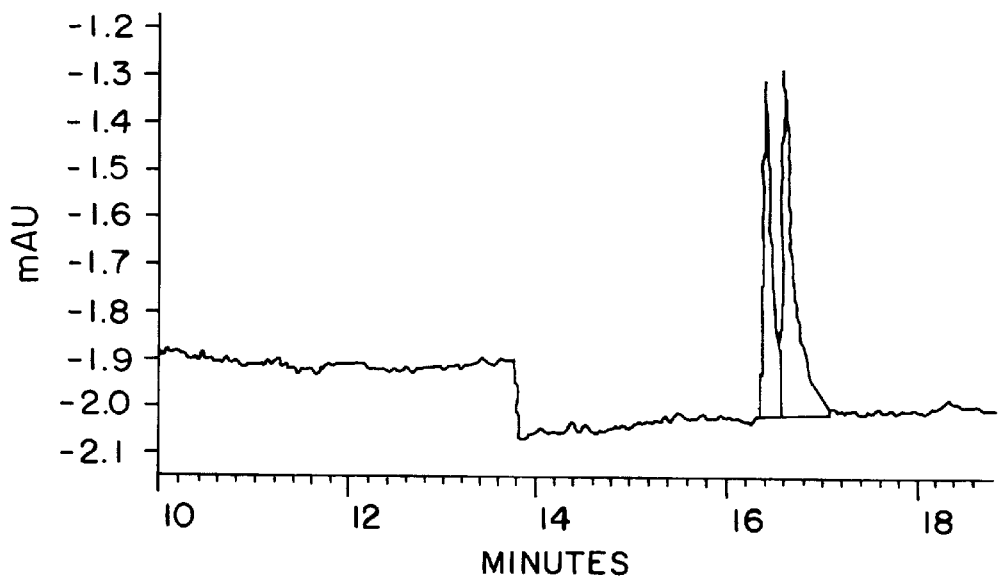
FIGS. 26(A)–(B) are chromatograms showing, in FIG. 26A, the separation of nicotine obtained with 100 mM (S)-dodecylaminocarbonylvaline (FIG. 3g, C12 tail) at pH 8.0, and in FIG. 26B, with 100 mM (S)-decylaminocarbonylvaline (FIG. 3ay, C10 tail) at pH 7.5.
Figure 26B:
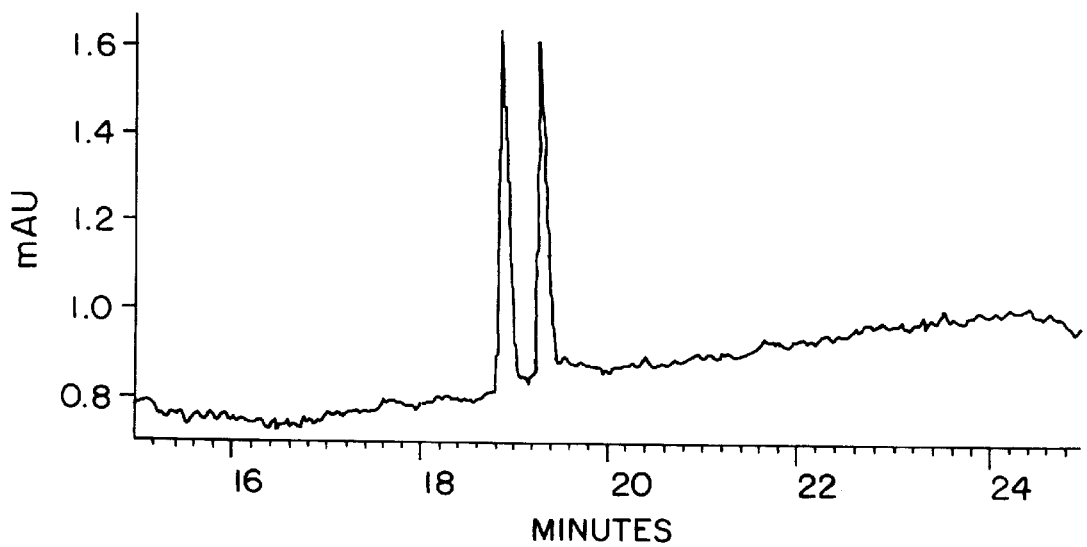

An example of how tail length can improve resolution through better pH solubility is shown in the separation of nicotine enantiomers, FIGS. 26A and 26B. The separation shown in FIG. 26A was obtained with 100 mM (S)-dodecylaminocarbonylvaline (FIG. 3g, C12 tail) at pH 8.0. Incomplete resolution and peak tailing were evident. The tailing was due to the fact that the surfactant was insoluble at pH 7.8, and at the analysis pH of 8.0 surfactant was binding to the wall. Resolution was incomplete because the enantioselectivity was too low. The separation in FIG. 26B was obtained with 100 mM (S)-decylaminocarbonylvaline (FIG. 3A25, C10 tail) at pH 7.5. Baseline resolution and symmetrical peaks were obtained, since at this pH the C10 derivative was well above its minimum pH of solubility (pH 6.7), and since higher enantioselectivity was obtained.

Example 27
Separation of Aspartame Stereoisomers

Aspartame, or Nutrasweet™ (GD Searle, Chicago, Ill.), is an artificial sweetener used in products ranging from diet soft drinks to pharmaceuticals. Aspartame is a dipeptide of aspartic acid and phenylalanine, with the C-terminus protected as the methyl ester. Since the dipeptide has two chiral centers, a total of four stereoisomers are possible; LL, DD, LD, DL. The LL isomer is marketed as the sweetener. However, it is important to monitor for the other stereoisomers as well, both in the raw material as well as in the finished product.

Figure 27:
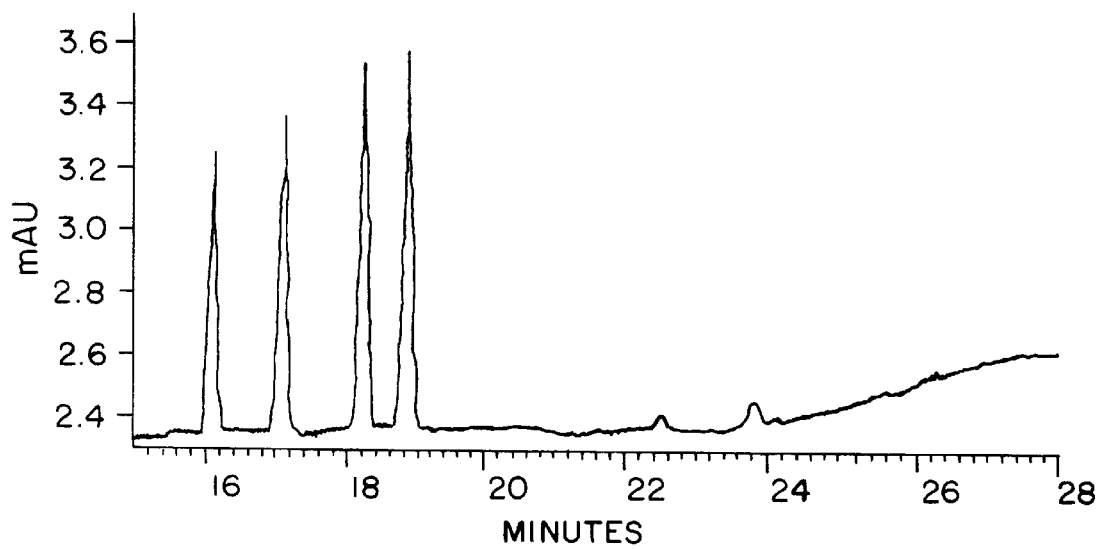
FIG. 27 is a chromatogram showing the separation of all four stereoisomers of aspartame suing 25 mM (S)-2-[(1-oxododecyl)-amino]-3-methyl-1-sulfooxybutane (FIG. 3m) at pH 3.5.

FIG. 27 shows separation of all four stereoisomers using 25 mM (S)-2-[(1-oxododecyl)-amino]-3-methyl-1-sulfooxybutane (FIG. 3m) at pH 3.5. The four stereoisomers were baseline resolved within 19 minutes. The later peaks at 22 and 24 minutes were probably due to breakdown products of the main isomers.

Example 28
Effect of Linker on UV Background

In order to show the influence of the linker on the resulting background UV absorbance of the chiral MECC buffer, the following experiment was conducted:

25 mM solutions of (S)-N-dodecanoylvaline (amide linker), (S)-N-dodecylaminocarbonylvaline (urea linker), and (S)-N-dodecoxycarbonylvaline (carbamate linker) were individually prepared in 25 mM $Na_2HPO_4$/25 mM $Na_2B_4O_7$ buffer. Using a 50 μm i.d. capillary and 214 nm UV detection, deionized water was drawn into the capillary with vacuum and the absorbance set to 0.000 absorbance units. The UV absorbance was then measured when blank buffer, 25 mM (S)-N-dodecanoylvaline in buffer, 25 mM (S)-N-dodecylaminocarbonylvaline in buffer, and 25 mM (S)-N-dodecoxycarbonylvaline in buffer were drawn into the capillary with vacuum. The absorbance of each solution is given in Table 10 below.

TABLE 10

| Solution | Absorbance (Absorbance units) |
|---|---|
| Blank Buffer | 0.000 |
| 25 mM amide linker in buffer | 0.037 |
| 25 mM urea linker in buffer | 0.026 |
| 25 mM carbamate linker in buffer | 0.007 |

As seen from the table, the amide linker led to the highest absorbance, 1.4 times the urea's absorbance and 5.3 times the carbamate's absorbance. High background absorbance is a large disadvantage in CE, since it will increase the noise level and decrease the linear range of detection. Note that a surfactant with two amide groups would show roughly 2 time the absorbance of one with only one amide group (assuming no other parts of the surfactant are UV active). This data should clearly show the disadvantage of amide linkers in chiral surfactants when employing UV absorbance detection, as well as highlight the advantage of the carbamate linker.

Although the foregoing invention has been described by way of illustration and example for purposes of clarity and understanding, it will be apparent that certain changes and modifications may be practiced within the scope of the invention, as limited only by the scope of the appended claims. For instance, the chiral selector may be one or more chiral carbons, arranged proximal to one another, or separated by some distance. The Tartanic Acid derivatives presented herein are but one example of a multiple chiral selector arrangement. The specific chiral selector is not limited, but rather may be selected from any class of chiral molecules imaginable, and still come within the scope of this invention. Similarly, the tail portion of the molecule, although primarily present to enhance hydrophobic interaction (partitioning) with the chiral analyte, may also contain a chiral carbon, as demonstrated herein. Chiral centers may be situated anywhere within the tail so that they may interact with the chiral center of the analyte. Head groups may be of any composition, so long as they fulfill the primary function of solubilizing the molecule in the solvent that the micelles are supported in, and potentiate enantioselectivity. Any linker molecules that potentiate the chiral selectivity of the chiral selector come within the scope of this invention.

We claim:

1. A method for separating a chiral compound into its constituent enantiomers, comprising the steps of:

(a) injecting said chiral compound into a channel that contains an electrolyte solution and a chiral surfactant that is present in the electrolyte solution in a concentration that is at or above its critical micelle concentration, said chiral surfactant having the general formula:

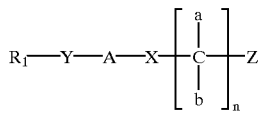

wherein
$R_1 = C_4-C_{18}$ linear alkyls, $C_4-C_{18}$ branched alkyls, $C_4-C_{18}$ halogen-substituted linear alkyls, $C_4-C_{18}$ polyether hydrocarbons, $C_4-C_{18}$ alkyls having a chiral center, all alkyls optionally being unsaturated, and cholesterolic hydrocarbons:
$Y = O$, $NH$ or $CH_2$;
$A = NH$, $CO$, $SO$ or $SO_2$;
$X = CO$, $O$ or $NH$;
$C$ = carbon;
$a \neq b$, and n may be from 1 to 5;
$Z = COO^-$, $SO_4^-$, $SO_3$, $PO_3^-$, $PO_4^-$, $NR'_3^-$, $PR'_3^-$, $OH$, polyethers, zwitterions, or polyalcohols;
$R' = H$ or $C_1-C_4$ linear or branched hydrocarbon, optionally halogenated, optionally unsaturated provided that the surfactant is not an N-alkanoyl amino acidate; and (b) applying a voltage that causes migration of the chiral compound, thereby separating the constituent enantiomers of the chiral compound.

2. A method of claim 1 wherein
$Y = O$;
$A = CO$;
$X = NH$;
a = an amino acid side chain and b=H, or vice versa; and
$Z = OH$, $SO_4^-$, or $COO^-$.

3. A method of claim 1 wherein
$Y = NH$;
$A = CO$;
$X = NH$;
a = an amino acid side chain and b=H, or vice versa; and
$Z = OH$, $SO_4^-$, or $COO^-$.

4. A method of claim 1 wherein
$Y = CH_2$;
$A = SO_2$;
$X = NH$;
a = an amino acid side chain and b=H, or vice versa; and
$Z = OH$, $SO_4^-$, or $COO^-$.

5. A method of claim 4 wherein
$Y = CH_2$;
$A = CO$;
$X = NH$;
a = an amino acid side chain and
b = H, or vice versa; and
$Z = OH$ or $SO_4^-$.

6. A method of claim 1 wherein
$Y = CH_2$;
$A = NH$;
$X = CO$;

a = an amino acid side chain and b=H, or vice versa; and
$Z = NR'_3^-$ wherein $R' = H$ or $C_1-C_8$ linear or branched hydrocarbons, optionally halogenated, optionally unsaturated.

7. The method of claim 1, wherein the chiral surfactant has the formula:

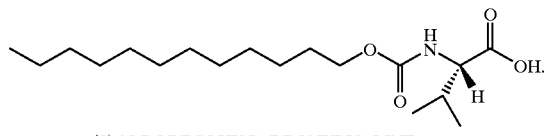

(S)-N-DODECOXYCARBONYLVALINE

8. The method of claim 1 wherein the chiral surfactant has the formula:

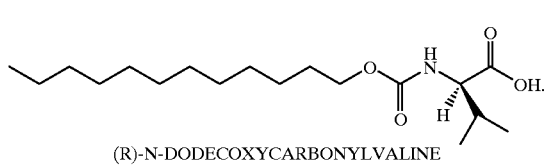

(R)-N-DODECOXYCARBONYLVALINE

9. The method of claim 1 wherein the chiral surfactant has the formula:

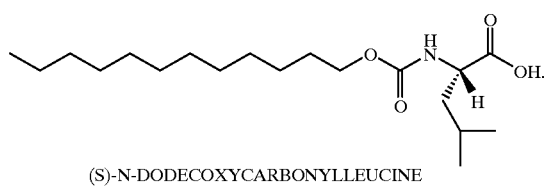

(S)-N-DODECOXYCARBONYLLEUCINE

10. The method of claim 1 wherein the chiral surfactant has the formula:

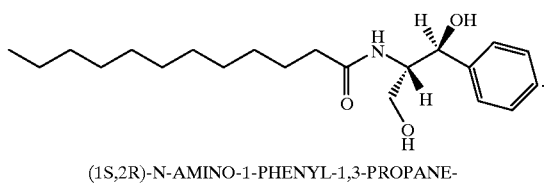

(1S,2R)-N-AMINO-1-PHENYL-1,3-PROPANE-DIOLDODECANAMIDE

11. The method of claim 1 wherein the chiral surfactant has the formula:

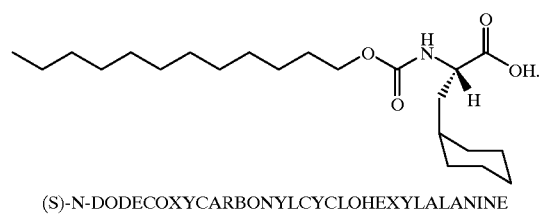

(S)-N-DODECOXYCARBONYLCYCLOHEXYLALANINE

12. The method of claim 1 wherein the chiral surfactant has the formula:

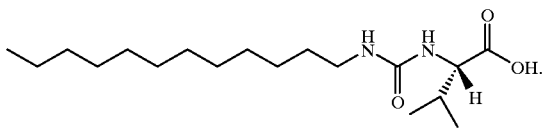

(S)-N-DODECYLAMINOCARBONYLVALINE

13. The method of claim 1 wherein the chiral surfactant has the formula:

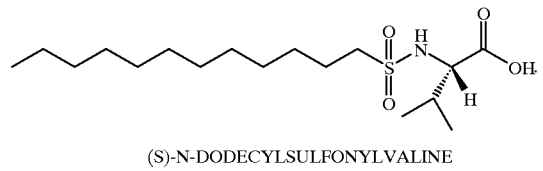

(S)-N-DODECYLSULFONYLVALINE

14. The method of claim 1 wherein the chiral surfactant has the formula:

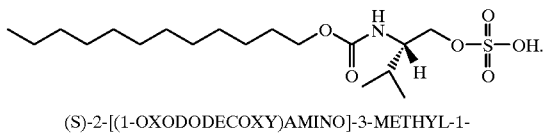

(S)-2-[(1-OXODODECOXY)AMINO]-3-METHYL-1-SULFOOXYBUTANE

15. The method of claim 1 wherein the chiral surfactant has the formula:

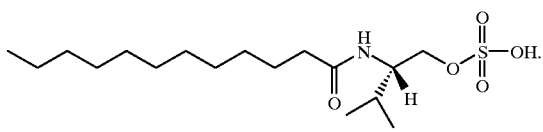

(S)-2-[(1-OXODODECYL)AMINO]-3-METHYL-1-SULFOOXYBUTANE

16. The method of claim 1 wherein the chiral surfactant has the formula:

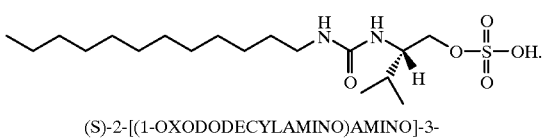

(S)-2-[(1-OXODODECYLAMINO)AMINO]-3-METHYL-1-SULFOOXYBUTANE

17. The method of claim 1 wherein the chiral surfactant has the formula:

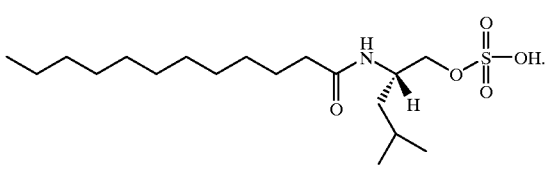

(S)-2-[(1-OXODODECYL)AMINO]-4-METHYL-1-SULFOOXYPENTANE

18. The method of claim 1 wherein the chiral surfactant has the formula:

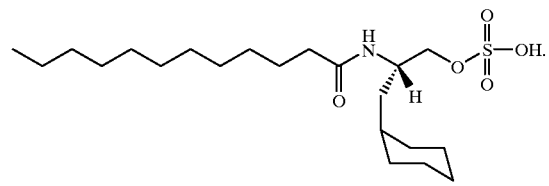

(S)-2-[(1-OXODODECYL)AMINO]-3-CYCLOHEXYL-1-SULFOOXYPROPANE

19. The method of claim 1 wherein the chiral surfactant has the formula:

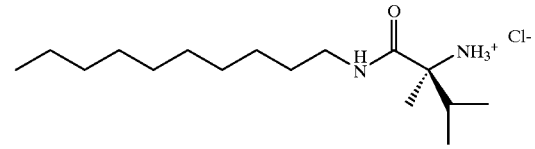

N-DECYL-(S)-VALINAMIDE HYDROCHLORIDE

20. The method of claim 1 wherein the chiral surfactant has the formula:

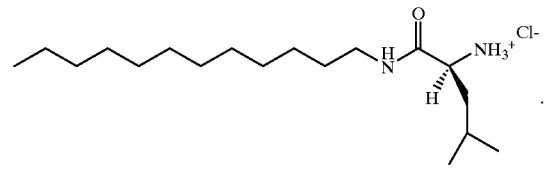

N-DODECYL-(S)-LEUCINAMIDE HYDROCHLORIDE

21. The method of claim 1, wherein the electrolyte solution contains two or more chiral surfactants.

22. A method for separating a chiral compound into its constituent enantiomers, comprising the steps of:
   (a) injecting said chiral compound into a channel that contains an electrolyte solution and a chiral surfactant that is present in the electrolyte solution in a concentration that is at or above its critical micelle concentration, said chiral surfactant having the general formula:

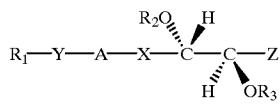

wherein $R_1 = C_4-C_{18}$ linear alkyls, $C_4-C_{18}$ branched alkyls, $C_4-C_{18}$ halogen-substituted linear alkyls, $C_4-C_{18}$ polyether hydrocarbons, $C_4-C_{18}$ alkyls having a chiral center, all alkyls optionally being unsaturated, and cholesterolic hydrocarbons;

$R_2$, $R_3$ = H or C1–C8 linear or branched alkyl or alkenyl hydrocarbons;

Y = $CH_2$;

A = NH;

X = CO;

C = carbon;

Z = $COO^-$, $SO_4^-$, $SO_3^-$, $PO_3^-$, $PO_4^-$, $NR'_3^-$, $PR'_3^-$, OH, polyethers, zwitterions, or polyalcohols; and R'=H or $C_1$–$C_4$ linear or branched hydrocarbon, optionally halogenated, optionally unsaturated; and (b) applying a voltage that causes migration of the chiral compound, thereby separating the constituent enantiomers of the chiral compound.

23. A method for separating a chiral compound into its constituent enantiomers, comprising the steps of:

(a) injecting said chiral compound into a channel that contains an electrolyte solution and a chiral surfactant that is present in the electrolyte solution in a concentration that is at or above its critical micelle concentration, said chiral surfactant having the general formula:

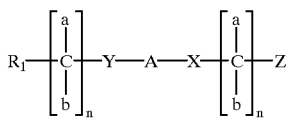

wherein $R_1$=$C_4$–$C_{18}$ linear alkyls, $C_4$–$C_{18}$ branched alkyls, $C_4$–$C_{18}$ halogen-substituted linear alkyls, $C_4$–$C_{18}$ polyether hydrocarbons, $C_4$–$C_{18}$ alkyls having from one to five chiral centers, all alkyls optionally being unsaturated, and cholesterolic hydrocarbons;

Y=O, NH or $CH_2$;

A=NH, CO, SO or $SO_2$;

X=O or NH;

C=a carbon atom;

a≠b, and n may be from 1 to 5;

Z=$COO^-$, $SO_4^-$, $SO_3^-$, $PO_3^-$, $PO_4^-$, $NR'_3^-$, $PR'_3^-$, OH, polyethers, zwitterions, or polyalcohols; and R'=H or $C_1$–$C_4$ linear or branched hydrocarbon, optionally halogenated, optionally unsaturated; and (b) applying a voltage that causes migration of the chiral compound, thereby separating the constituent enantiomers of the chiral compound.

24. A method for separating a chiral compound into its constituent enantiomers, comprising the steps of:

(a) injecting said chiral compound into a channel that contains an electrolyte solution and a chiral surfactant that is present in the electrolyte solution in a concentration that is at or above its critical micelle concentration, said chiral surfactant having the following components:

(1) a chiral selector, said chiral selector having at least one chiral center;

(2) a hydrophilic head group bonded to said chiral selector;

(3) a linker bonded to said chiral selector; and (4) a hydrophobic tail bonded to said linker, provided that said chiral surfactant is not an N-alkanoyl amino acidate; and (b) applying a voltage that causes migration of the chiral compound, thereby separating the constituent enantiomers of the chiral compound.

25. The method of claim 24 wherein said chiral selector is selected from the group consisting of amino acids, aminoalcohols, tartrates, and the respective salts thereof.

26. The method of claim 24 wherein said linker which in combination with the chiral selector functionality is selected from the group consisting of carbamates, sulphonamides, and ureas.

27. The method of claim 24 wherein said hydrophilic head group is selected from the group consisting of quaternary ammoniums, ammonium salts, carboxylates, alcohols, sulfates, sulfonic acids, polyalcohols, zwitterions, and the respective salts thereof.

28. The method of claim 24 wherein said hydrophobic tail is selected from the group consisting of linear alkyls, substituted linear alkyls, linear alkenyls, halogen substituted linear alkenyls, cholesterolic, and polyether hydrocarbons.

29. The method of claim 24 wherein said chiral selector is an amino acid.

30. The method of claim 24 wherein said chiral selector is an amino alcohol.

31. The method of claim 24 wherein said chiral selector is a tartaric acid or derivative thereof.

32. A method for separating a hydrophilic chiral compound into its constituent enantiomers, comprising the steps of:

(a) injecting said chiral compound into a channel that contains an electrolyte solution and a chiral surfactant that is present in the electrolyte solution in a concentration that is at or above its critical micelle concentration, said chiral surfactant having the general formula:

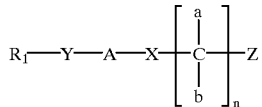

wherein, $R_1$=$C_4$–$C_{18}$ linear alkyls, $C_4$–$C_{18}$ branched alkyls, $C_4$–$C_{18}$ halogen-substituted linear alkyls, $C_4$–$C_{18}$ polyether hydrocarbons, $C_4$–$C_{18}$ alkyls having a chiral center, all alkyls optionally being unsaturated, and cholesterolic hydrocarbons;

Y=O, NH, or $CH_2$;

A=NH, CO, SO or $SO_2$;

X=CO, O or NH;

C=carbon;

a≠b, and n may be from 1 to 5;

Z=$COO^-$, $SO_4^-$, $SO_3^-$, $PO_3^-$, $PO_4^-$, $NR'_3^-$, $PR'_3^-$, OH, polyethers, zwitterions, or polyalcohols;

R'=H or $C_1$–$C_4$ linear or branched hydrocarbon, optionally halogenated, optionally unsaturated; and (b) applying a voltage that causes migration of the chiral compound, thereby separating the constituent enantiomers of the chiral compound.

33. A method for separating a chiral compound having one or more acidic functional groups into its constituent enantiomers, comprising the steps of:

(a) injecting said chiral compound into a channel that contains an electrolyte solution and a chiral surfactant that is present in the electrolyte solution in a concentration that is at or above its critical micelle concentration, said chiral surfactant having the general formula:

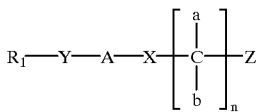

wherein, $R_1 =C_4–C_{18}$ linear alkyls, $C_4–C_{18}$ branched alkyls, $C_4–C_{18}$ halogen-substituted linear alkyls, $C_4–C_{18}$ polyether hydrocarbons, $C_4–C_{18}$ alkyls having a chiral center, all alkyls optionally being unsaturated, and cholesterolic hydrocarbons;

Y=O, NH or $CH_2$;

A=NH, CO, SO or $SO_2$;

X=CO, O or NH;

C=carbon;

a≠b, and n may be from 1 to 5;

Z=$NR'_3{}^-$, $PR'_3{}^-$, OH, polyethers, zwitterions, or polyalcohols;

R'=H or $C_1–C_4$ linear or branched hydrocarbon, optionally halogenated, optionally unsaturated; and (b) applying a voltage that causes migration of the chiral compound, thereby separating the constituent enantiomers of the chiral compound.

34. A method for separating a chiral compound having one or more basic functional groups into its constituent enantiomers, comprising the steps of:

(a) injecting said chiral compound into a channel that contains an electrolyte solution and a chiral surfactant that is present in the electrolyte solution in a concentration that is at or above its critical micelle concentration, said chiral surfactant having the general formula:

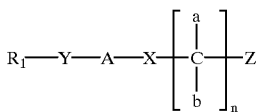

wherein, $R_1 =C_4–C_{18}$ linear alkyls, $C_4–C_{18}$ branched alkyls, $C_4–C_{18}$ halogen-substituted linear alkyls, $C_4–C_{18}$ polyether hydrocarbons, $C_4–C_{18}$ alkyls having a chiral center, all alkyls optionally being unsaturated, and cholesterolic hydrocarbons:

Y=O, NH or $CH_2$;

A=NH, CO, SO or $SO_2$;

X=CO, O or NH;

C=carbon;

a≠b, and n may be from 1 to 5;

Z=$COO^-$, $SO_4{}^-$, $SO_3{}^-$, $PO_3{}^-$, $PO_4{}^-$, OH, polyethers, zwitterions, or polyalcohols;

R'=H or $C_1–C_4$ linear or branched hydrocarbon, optionally halogenated, optionally unsaturated; and (b) applying a voltage that causes migration of the chiral compound, thereby separating the constituent enantiomers of the chiral compound.

35. A method for separating a zwitterionic chiral compound into its constituent enantiomers, comprising the steps of:

(a) injecting said chiral compound into a channel that contains an electrolyte solution and a chiral surfactant that is present in the electrolyte solution in a concentration that is at or above its critical micelle concentration, said chiral surfactant having the general formula:

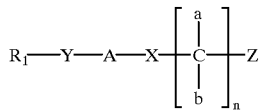

wherein, $R_1 =C_4–C_{18}$ linear alkyls, $C_4–C_{18}$ branched alkyls, $C_4–C_{18}$ halogen-substituted linear alkyls, $C_4–C_{18}$ polyether hydrocarbons, $C_4–C_{18}$ alkyls having a chiral center, all alkyls optionally being unsaturated, and cholesterolic hydrocarbons:

Y=O, NH or $CH_2$;

A=NH, CO, SO or $SO_2$;

X=CO, O or NH;

C=carbon;

a≠b, and n may be from 1 to 5;

Z=$COO^-$, $SO_4{}^-$, $SO_3$, $PO_3{}^-$, $PO_4{}^-$, $NR'_3{}^-$, $PR'_3{}^-$, OH, polyethers, zwitterions, or polyalcohols;

R'=H or $C_1–C_4$ linear or branched hydrocarbon, optionally halogenated, optionally unsaturated; and (b) applying a voltage that causes migration of the chiral compound, thereby separating the constituent enantiomers of the chiral compound.

36. A method for separating aspartame into its constituent enantiomers, comprising the steps of:

(a) injecting aspartame into a channel that contains an electrolyte solution and the chiral surfactant (S)-2-[(1-oxododecyl) amino]-3-methyl-1-sulfoxybutane that is present in the electrolyte solution in a concentration that is at or above its critical micelle concentration; and (b) applying a voltage that causes migration of the aspartame, thereby separating the constituent enantiomers of aspartame.

37. A chiral surfactant having the general formula:

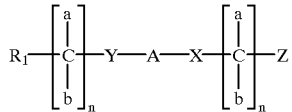

wherein, $R_1 =C_4–C_{18}$ linear alkyls, $C_4–C_{18}$ branched alkyls, $C_4–C_{18}$ halogen-substituted linear alkyls, $C_4–C_{18}$ polyether hydrocarbons, $C_4–C_{18}$ alkyls having from one to five chiral centers, all alkyls optionally being unsaturated, and cholesterolic hydrocarbons;

Y=O, NH or $CH_2$;

A=NH, CO, SO or $SO_2$;

X=O or NH;

C=a carbon atom;

a≠b, and n may be from 1 to 5;

Z=$COO^-$, $SO_4{}^-$, $SO_3{}^-$, $PO_3{}^-$, $PO_4$, $NR'_3{}^-$, $PR'_3{}^-$, OH, polyethers, zwitterions, or polyalcohols; and R'=H or $C_1–C_4$ linear or branched hydrocarbon, optionally halogenated, optionally unsaturated.

38. A chiral surfactant having the following structural formula:

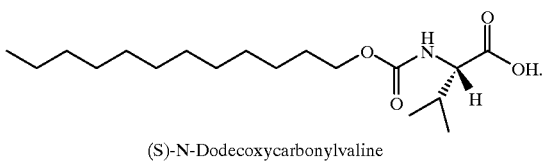

(S)-N-Dodecoxycarbonylvaline

39. A chiral surfactant having the following structural formula:

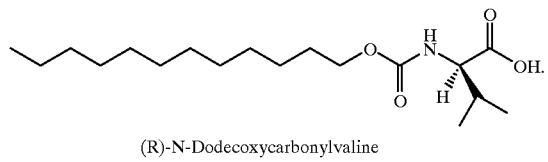

(R)-N-Dodecoxycarbonylvaline

40. A chiral surfactant having the following structural formula:

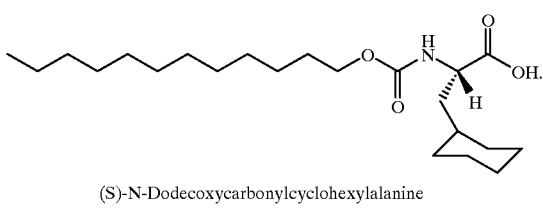

(S)-N-Dodecoxycarbonylcyclohexylalanine

41. A chiral surfactant having the following structural formula:

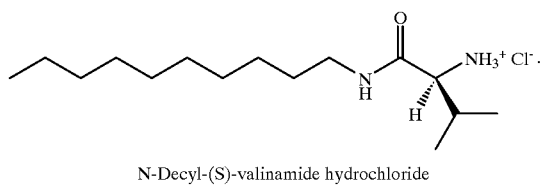

N-Decyl-(S)-valinamide hydrochloride

42. A chiral surfactant having the following structural formula:

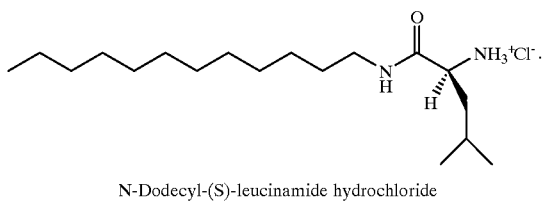

N-Dodecyl-(S)-leucinamide hydrochloride

43. A chiral surfactant having the general formula:

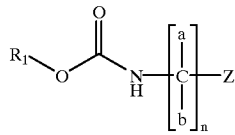

wherein, $R_1 = C_4 - C_{18}$ linear alkyls, $C_4 - C_{18}$ branched alkyls, $C_4 - C_{18}$ halogen-substituted linear alkyls, $C_4 - C_{18}$ polyether hydrocarbons, $C_4 - C_{18}$ alkyls having a chiral center, all alkyls optionally being unsaturated, and cholesterolic hydrocarbons:

C=carbon;

n is an integer from 1 to 5;

A=an amino acid side chain and b=H, or vice versa; and

Z=OH or $SO_4^-$.

44. The chiral surfactant of claim 43 wherein said surfactant has the formula:

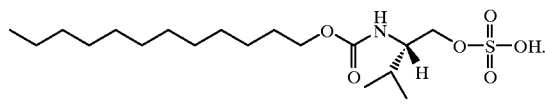

(S)-2-[(1-Oxododecoxy)amino]-3-methyl-1-sulfooxybutane

45. A chiral surfactant having the general formula:

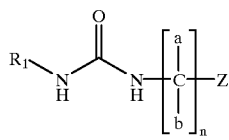

wherein, $R_1 = C_4 - C_{18}$ linear alkyls, $C_4 - C_{18}$ branched alkyls, $C_4 - C_{18}$ halogen-substituted linear alkyls, $C_4 - C_{18}$ polyether hydrocarbons, $C_4 - C_{18}$ alkyls having a chiral center, all alkyls optionally being unsaturated, and cholesterolic hydrocarbons:

C=carbon;

n is an integer from 1 to 5;

A=an amino acid side chain and B=H, or vice versa; and

Z=OH and $SO_4^-$.

46. The chiral surfactant of claim 45 wherein said surfactant has the formula:

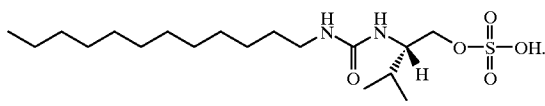

(S)-2-[(1-Oxododecylamino)amino]-3-methyl-1-sulfooxybutane

47. A chiral surfactant having the general formula:

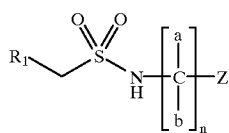

wherein, $R_1 = C_4 - C_{18}$ linear alkyls, $C_4 - C_{18}$ branched alkyls, $C_4 - C_{18}$ halogen-substituted linear alkyls, $C_4 - C_{18}$ polyether hydrocarbons, $C_4 - C_{18}$ alkyls having a chiral center, all alkyls optionally being unsaturated, and cholesterolic hydrocarbons:

C=carbon;

n is an integer from 1 to 5;

A=an amino acid side chain and B=H, or vice versa; and

Z=OH and $SO_4^-$, or $COO^-$.

48. The chiral surfactant of claim 47 wherein said surfactant has the formula:

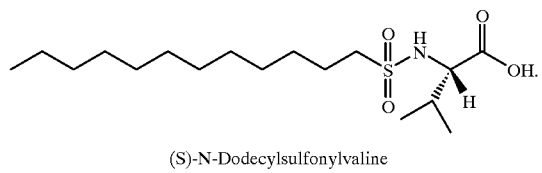

(S)-N-Dodecylsulfonylvaline

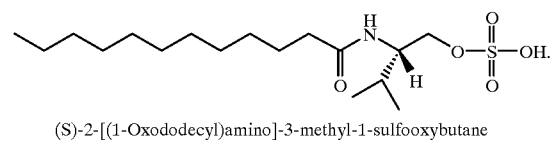

(S)-2-[(1-Oxododecyl)amino]-3-methyl-1-sulfooxybutane

49. A chiral surfactant having the general formula:

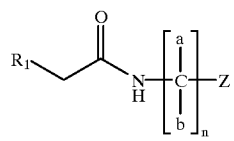

wherein, $R_1 = C_4-C_{18}$ linear alkyls, $C_4-C_{18}$ branched alkyls, $C_4-C_{18}$ halogen-substituted linear alkyls, $C_4-C_{18}$ polyether hydrocarbons, $C_4-C_{18}$ alkyls having a chiral center, all alkyls optionally being unsaturated, and cholesterolic hydrocarbons:

C=carbon;

n is an integer from 1 to 5;

A=an amino acid side chain and B=H, or vice versa; and

Z=OH and $SO_4^-$.

50. The chiral surfactant of claim 49 wherein said surfactant has the formula:

51. The chiral surfactant of claim 49 wherein said surfactant has the formula:

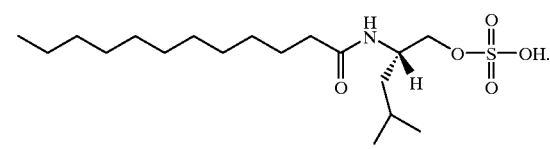

(S)-2-[(1-Oxododecyl)amino]-4-methyl-1-sulfooxypentane

52. The chiral surfactant of claim 49 wherein said surfactant has the formula:

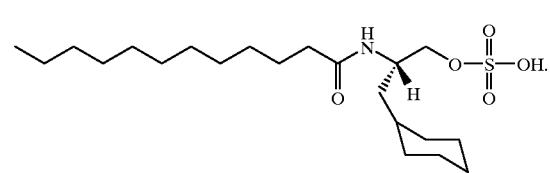

(S)-2-[(1-Oxododecyl)amino]-3-cyclohexyl-1-sulfooxypropane

* * * * *

UNITED STATES PATENT AND TRADEMARK OFFICE
CERTIFICATE OF CORRECTION

PATENT NO. : 6,090,250
DATED : July 18, 2000
INVENTOR(S) : Jeffrey R. Mazzeo, Edward R. Grover, Michael E. Swartz, Michael Merion and John S. Petersen It is certified that error appears in the above-identified patent and that said Letters Patent is hereby corrected as shown below:

At Claim 23, Col. 31, Line 34, delete "$NR'_3{}^-$, $PR'_3{}^-$" and insert ---$NR'_3{}^+$, $PR'_3{}^+$---.

At Claim 24, Col. 31, Line 44, delete "and a" and insert ---having---.

At Claim 32, Col. 32, Line 50, delete "$NR'_3{}^-$, $PR'_3{}^-$" and insert ---$NR'_3{}^+$, $PR'_3{}^+$---.

At Claim 33, Col. 33, Line 20, delete "$NR'_3{}^-$, $PR'_3{}^-$" and insert ---$NR'_3{}^+$, $PR'_3{}^+$---.

At Claim 35, Col. 34, Line 24, delete "$NR'_3{}^-$, $PR'_3{}^-$" and insert ---$NR'_3{}^+$, $PR'_3{}^+$---.

At Claim 37, Col. 34, Line 62, delete "$NR'_3{}^-$, $PR'_3{}^-$" and insert ---$NR'_3{}^+$, $PR'_3{}^+$---.

At Claim 45, Col. 36, Line 35, delete " B" and insert --- b---.

At Claim 47, Col. 36, Line 64, delete " B" and insert --- b---.

Signed and Sealed this

Seventeenth Day of April, 2001

Attest:

NICHOLAS P. GODICI

Attesting Officer    Acting Director of the United States Patent and Trademark Office